(12) United States Patent
Naniwa et al.

(10) Patent No.: US 6,589,984 B1
(45) Date of Patent: Jul. 8, 2003

(54) BENZOFURYLPYRONE DERIVATIVES

(75) Inventors: Yoshimitsu Naniwa, Hino (JP); Hiroshi Imai, Hino (JP); Tomohide Ida, Hino (JP); Emiko Muratani, Hino (JP); Kazuo Kitai, Hino (JP); Yoshinori Sugimoto, Hino (JP); Tomomi Kosugi, Hino (JP); Akiko Takeuchi, Hino (JP); Kunihito Watanabe, Hino (JP); Takami Tomiyama, Sakai (JP); Tomio Takeuchi, Tokyo (JP); Masa Hamada, Tokyo (JP)

(73) Assignees: Teijin Limited, Osaka (JP); Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 09/646,005
(22) PCT Filed: Mar. 12, 1999
(86) PCT No.: PCT/JP99/01225
§ 371 (c)(1),
(2), (4) Date: Sep. 11, 2000
(87) PCT Pub. No.: WO99/46262
PCT Pub. Date: Sep. 16, 1999

(30) Foreign Application Priority Data

Mar. 12, 1998 (JP) .......................................... 10-061356

(51) Int. Cl.[7] ............................................. C07D 309/32
(52) U.S. Cl. ...................... 514/460; 549/292; 549/293; 549/294
(58) Field of Search .................... 514/460; 549/292, 549/293, 294

(56) References Cited

U.S. PATENT DOCUMENTS 4,668,803 A    5/1987  Berman et al. ............. 549/291
5,393,729 A    2/1995  Fischer et al.
6,005,103 A   12/1999  Domagala et al.

FOREIGN PATENT DOCUMENTS

HU    212 103 B        7/1881
WO    WO 94/11361      5/1994

OTHER PUBLICATIONS

Ram, Vishnu Ji, et al., "Synthesis and reactions of 6–aryl–3–cyano–4–methylthio–2H–pyran–2–ones", Indian Journal of Chemistry, vol. 29B, Jul. 1990, pp. 624–627.

Primary Examiner—Taofiq Solola
(74) Attorney, Agent, or Firm—Sughrue Mion, PLLC

(57) ABSTRACT

There is provided benzofuryl-α-pyrone derivative represented by the following structural formula (I):

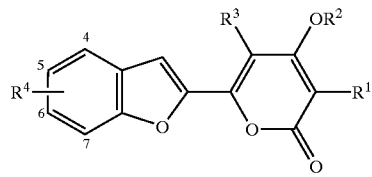

wherein $R^1$ represents a hydrogen atom or an alkyl group of 1 to 5 carbons;

$R^2$ represents hydrogen, —CO—$R^5$ or —SO$_2$R$^6$;

$R^3$ represents hydrogen, an alkyl group of 1 to 5 carbons, etc.; and $R^4$ is a substituent attached to the 4-carbon, 5-carbon, 6-carbon or 7 carbon of the benzofuran ring; and their salts. The compounds are useful as therapeutic agent for hypertriglyceridemia, lipid metabolism enhancers, or prophylactic and/or therapeutic agents for arteriosclerosis.

19 Claims, No Drawings

BENZOFURYLPYRONE DERIVATIVES

This application is a 371 of PCT/JP99/01225 filed Mar. 12, 1999.

TECHNICAL FIELD

The present invention relates to novel benzofuryl-α-pyrone derivatives and to medicines containing them as active ingredients. More specifically, the invention relates to novel benzofuryl-α-pyrone derivatives and to lipid metabolism enhancers, arteriosclerosis prophylactic agents, arteriosclerosis treatment agents, triglyceride biosynthesis inhibitors, blood triglyceride lowering agents or blood HDL elevating agents containing them as active ingredients.

BACKGROUND ART

Blood cholesterol and triglycerides (TG) themselves are generally insoluble in blood, and they exist as lipoproteins by binding with apolipoproteins. In the body, triglycerides are biosynthesized primarily in the liver from acetyl CoA as the starting substance which is produced from sugars, etc., by 6 different enzymes and one enzyme group (acetyl CoA carboxylase, the fatty acid synthase group, fatty acyl CoA synthase, glycerophosphoric acid acyl transferase, lysophosphatidic acid acyl transferase, phosphatidic acid phosphatase and diacylglycerol acyl transferase), and are secreted from the liver into the blood as lipoproteins.

The condition of a higher-than-normal cholesterol and/or triglyceride blood level is known as hyperlipidemia. The condition termed hyperlipidemia is classified into 6 types based on the lipoproteins in the blood, according to the Fredrickson classification (WHO classification). Types I, IV and V are characterized by increased triglycerides only, type IIa by increased cholesterol, and types IIb and III by increases in both ("Sogo Rinsho", 43, 871(1994)). This means that present hyperlipidemia drugs (that lower only cholesterol or that lower both cholesterol and triglycerides) cannot always be appropriately applied for all hyperlipidemia cases. In particular, type IV accounts for 40 to 50% of male hyperlipidemia patients ("Rinsho to Kenkyu", 69, 318(1992)). Most secondary onset forms accompanying diabetes are also type IV ("Sogo Rinsho", 43, 878(1994)).

Hypertriglyceridemia is a condition in which blood triglyceride levels are increased, and in the past few years it has been receiving attention among clinical physicians and pharmaceutical manufacturers as a risk factor in arteriosclerosis and ischemic diseases.

Because most attention in the field of hyperlipidemia, which includes hypertriglyceridemia, has been focused on cholesterol alone, which is directly implicated in arteriosclerosis, few drugs have been developed with the aim of lowering triglycerides, and treatment of hypertriglyceridemia has been limited to the use of clofibrate-based hypolipidemic drugs or nicotinic acid preparations as the existing hypolipidemic drugs. Because these must be used in high doses and many action sites have been reported, there are concerns about a number of related side-effects (The Lipid, 5, 65 to 72(1994)). It would therefore be highly desirable to find a new type of drug that has a triglyceride-lowering effect at low doses, exhibits few side-effects and has a clear action mechanism.

Hypertriglyceridemia occurs as a result of various causes, including genetic background and, as mentioned above, secondary onset accompanying diabetes, etc. ("Sogo Rinsho", 43, 878(1994)); more specifically, it is attributed to:

A. accelerated triglyceride synthesis (secretion) in the liver, and

B. delayed decomposition of synthesized triglycerides (present in the blood as lipoproteins) by lipoprotein lipase (LPL) ("Rinsho to Kenkyu", 69, 340(1992)). In particular, for hypertriglyceridemia accompanying diabetes, A. is said to be the cause of non-insulin-dependent diabetes mellitus (NIDDM), while B. is said to be the cause of insulin-dependent diabetes mellitus (IDDM) ("Rinsho to Kenkyu", 69, 379(1992)). Consequently, the action mechanism of therapeutic agents for hypertriglyceridemia is believed to be inhibition of triglyceride synthesis (secretion) in the liver and/or accelerated decomposition of synthesized triglycerides (present in the blood as lipoproteins) by lipoprotein lipase (LPL).

In the prior art there have been known α-pyrone derivatives with substitution of a heteroaromatic ring at the C-6 position, for example, in WO 9635664, WO 9514013, WO 9514014, EP 588137, U.S. Pat. No. 4,668,803, FR 2665445, Japanese Unexamined Patent Publication SHO No. 49-5976, Japanese Unexamined Patent Publication No. 8-503216, Japanese Unexamined Patent Publication No. 9-505291, Japanese Unexamined Patent Publication No. 9-505293, Japanese Unexamined Patent Publication No. 9-505294, Japanese, Unexamined Patent Publication No. 9-505295, or for example, in Tetrahedron Letters, 37, 6461 (1996), J. Chem. Research (S), 86 (1994), Chem. Pharm. Bull., 32, 1665 (1984), Chem. Ber., 100, 658 (1967) and J. Org. Chem., 54, 3985 (1989).

However, no explanation or suggestion has been published regarding a triglyceride biosynthesis inhibiting effect, blood triglyceride lowering effect or blood HDL elevating effect for any of these α-pyrone derivatives of the prior art.

Of the prior art publications, WO 9635664 and EP 588137 describe compounds with a structural feature wherein phenyl is a substituent at the C-3 position of the α-pyrone ring, but no description or suggestion is given regarding the use of an alkyl group instead of a phenyl group as the substituent at the C-3 position of the α-pyrone ring.

Similarly, U.S. Pat. No. 4,668,803 among the prior art publications describes α-pyrone derivatives wherein the substituent at the C-3 position is an acyl group of 2 to 11 carbons or a phenyl group, but no description or suggestion is given regarding the use of an alkyl group instead of an acyl group of 2 to 11 carbons or a phenyl group as the substituent at the C-3 position of the α-pyrone ring.

Also, FR 2665445 among the prior art publications describes α-pyrone derivatives with —S(O)$_n$—R$^1$ as a substituent at the C-4 position, wherein n is 1 or 2 and R$^1$ represents an alkyl group of 1 to 6 carbons, a benzyl group or a phenyl group. However, no description or suggestion is given regarding the use of OH, OCOR or OSO$_2$R instead of —S(O)$_n$—R$^1$ as the substituent at the C-4 position of the α-pyrone ring.

Likewise, Japanese Unexamined Patent Publication No. 49-5976 among the prior art publications describes α-pyrone derivatives with hydrogen, a lower alkyl group or phenyl as a substituent at the C-4 position, but no description or suggestion is given regarding the use of OH, OCOR or OSO$_2$R instead of hydrogen, a lower alkyl group or phenyl as the substituent at the C-4 position of the α-pyrone ring.

Likewise, Chem. Ber., 100, 658 (1967) among the prior art publications describes α-pyrone derivatives with hydrogen, methyl or ethyl as a substituent at the C-4 position, but no description or suggestion is given regarding the use of OH, OCOR or OSO$_2$R instead of hydrogen, methyl or ethyl as the substituent at the C-4 position of the α-pyrone ring.

Likewise, J. Chem. Research (S), 86(1994) among the prior art publications describes α-pyrone derivatives with an SMe group as a substituent at the C-4 position, but no description or suggestion is given regarding the use of OH, OCOR or OSO$_2$R instead of an SMe group as the substituent at the C-4 position of the α-pyrone ring.

In addition, Tetrahedron Letters, 37, 6461 (1996), Chem. Pharm. Bull., 32, 1665 (1984) and J. Org. Chem., 54, 3985 (1989) among the prior art publications describe α-pyrone derivatives with a pyridyl group substituent at the C-6 position, but no description or suggestion is given regarding the use of a benzofuryl group instead of a pyridyl group as the substituent at the C-6 position of the α-pyrone ring.

DISCLOSURE OF THE INVENTION

It is an object of the present invention to provide benzofuryl-α-pyrone derivatives, and especially novel benzofuryl-α-pyrone derivatives having a benzofuryl group as a substituent at the C-6 position of the α-pyrone ring.

It is another object of the invention to provide lipid metabolism enhancers, arteriosclerosis prophylactic agents or arteriosclerosis treatment agents, and especially to provide triglyceride biosynthesis inhibitors, blood triglyceride lowering agents or blood HDL elevating agents, that contain as active ingredients the novel benzofuryl-α-pyrone derivatives having a benzofuryl group as a substituent at the C-6 position of the α-pyrone ring.

The present inventors have conducted much research in light of the prior art cited above, and as a result the inventors have found that benzofuryl-α-pyrone derivatives, and especially benzofuryl-α-pyrone derivatives having a benzofuryl group as a substituent at the C-6 position of the α-pyrone ring, have a triglyceride biosynthesis inhibiting effect, a blood triglyceride lowering effect and a blood HDL elevating effect; the present invention have been achieved after still further research on the same.

Specifically, the present invention provides benzofuryl-α-pyrone derivatives (and salts thereof) represented by the following structural formula (I)

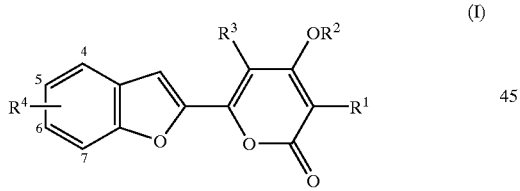

(I)

wherein
- $R^1$ represents hydrogen or an alkyl group of 1 to 5 carbons;
- $R^2$ represents hydrogen, —CO—$R^5$ (wherein $R^5$ represents hydrogen, an alkyl group of 1 to 5 carbons with optional substituents, a cycloalkyl group of 3 to 7 carbons, an aryl group of 6 to 10 carbons or a heterocycle), or —SO$_2$R$^6$ (wherein $R^6$ represents an optionally halogen-substituted alkyl group of 1 to 5 carbons or aryl group of 6 to 10 carbons);
- $R^3$ represents hydrogen, an alkyl group of 1 to 5 carbons, an alkenyl group of 2 to 5 carbons, an alkynyl group of 2 to 5 carbons, a cycloalkyl group of 3 to 7 carbons, a cycloalkyl group of 3 to 7 carbons-alkyl group of 1 to 5 carbons, an aryl group of 6 to 10 carbons, an aralkyl group of 7 to 20 carbons, an alkoxy group of 1 to 5 carbons or an aryloxy group of 6 to 10 carbons;
- $R^4$ is a substituent at the C-4 position, C-5 position, C-6 position or C-7 position of the benzofuran ring and represents:
  - $R^{4a}$ which represents hydrogen, a nitro group, a cyano group, a halogen atom, a heterocycle, an alkenyl group of 2 to 5 carbons, an alkynyl group of 2 to 5 carbons, an aryl group of 6 to 10 carbons, A=CH(CH$_2$)$_n$— (wherein A represents an alicyclic heterocycle, "=" represents a double bond and n represents 0, 1 or 2), A=CH(CH$_2$)$_m$O— (wherein A represents an alicyclic heterocycle, "=" represents a double bond and m represents 1, 2 or 3), A—SO$_2$—(CH$_2$)$_m$— (wherein A represents an alicyclic heterocycle and m represents 1, 2 or 3), —OR$^7$ (wherein R$^7$ represents hydrogen, a cycloalkyl group of 3 to 7 carbons, an aryl group of 6 to 10 carbons, a heterocycle, an optionally halogen-substituted alkylsulfonyl group of 1 to 4 carbons, or an arylsulfonyl group of 6 to 10 carbons), —O—CO—R$^8$ (wherein R$^8$ represents hydrogen, an alkyl group of 1 to 4 carbons, an aryl group of 6 to 10 carbons, an aralkyl group of 7 to 20 carbons or a heterocycle), —NR$^9$R$^{10}$ (wherein R$^9$ and R$^{10}$ each independently represents hydrogen, an alkyl group of 1 to 4 carbons, an aralkyl group of 7 to 20 carbons, a phenyl group, a heterocycle, —SO$_2$—R$^{11}$ (wherein R$^{11}$ represents an optionally halogen-substituted alkyl group of 1 to 12 carbons, a heterocycle-substituted alkyl group of 1 to 6 carbons, an aryl group of 6 to 10 carbons, a heterocycle or an aralkyl group of 7 to 20 carbons) or —CO—R$^{12}$ (wherein R$^{12}$ represents hydrogen, an alkyl group of 1 to 12 carbons, an aryl group of 6 to 10 carbons, an aralkyl group of 7 to 20 carbons, a heterocycle, an alkoxy group of 1 to 10 carbons, a heterocycle-substituted alkyl group of 1 to 6 carbons, an aryloxy group of 6 to 10 carbons, a heteroaryloxy group or an aralkyloxy group of 7 to 20 carbons)), —CO—R$^{13}$ (wherein R$^{13}$ represents hydrogen, —OH, an alkyl group of 1 to 4 carbons, an aryl group of 6 to 10 carbons, a heterocycle, an alkoxy group of 1 to 4 carbons, an aryloxy group of 6 to 10 carbons or an aralkyloxy group of 7 to 20 carbons), or —CO—NR$^{14}$R$^{15}$ (wherein R$^{14}$ and R$^{15}$ each independently represents hydrogen, an alkyl group of 1 to 4 carbons, a cycloalkyl group of 3 to 7 carbons, an aryl group of 6 to 10 carbons, an aralkyl group of 7 to 20 carbons, a heterocycle or a heterocycle-substituted alkyl group of 1 to 4 carbons);
  - $R^{4b}$ which represents a saturated or unsaturated alkoxy group of 1 to 6 carbons optionally substituted with 1 to 3 groups selected from the group consisting of halogens, cycloalkyl groups of 3 to 7 carbons, phenyl, naphthyl, heterocycles, —OR$^{16}$ (wherein R$^{16}$ represents hydrogen, an alkyl group of 1 to 4 carbons, a phenyl group, a naphthyl group, a benzyl group or a heterocycle), —O—CO—R$^{16}$ (wherein R$^{16}$ represents hydrogen, an alkyl group of 1 to 4 carbons, a phenyl group, a naphthyl group, a benzyl group or a heterocycle), —NR$^{17}$R$^{18}$ (wherein R$^{17}$ and R$^{18}$ each independently represents hydrogen, an alkyl group of 1 to 4 carbons, a heterocycle, an alkylsulfonyl group of 1 to 4 carbons, a phenylsulfonyl group, —SO$_2$-Het (wherein Het represents a heterocycle), an aminosulfonyl group, a methylaminosulfonyl group, a dimethylaminosulfonyl group, a diethylaminosulfonyl group, or an alkyl group of 1 to 4 carbons substituted with 1 or 2 groups selected from among phenyl, heterocycles, phenoxy, —O-Het (wherein Het represents a heterocycle) and hydroxyl, —NH—CO—$R^{19}$ (wherein $R^{19}$ represents hydrogen, an alkyl group of 1 to 4 carbons, a phenyl group, a naphthyl group, a benzyl group, a heterocycle, an alkoxy group of 1 to 4 carbons or a benzyloxy group), —CO—$R^{20}$ (wherein $R^{20}$ represents hydrogen, a heterocycle, an alkoxy group of 1 to 4 carbons, a phenoxy group, a benzyloxy group or —$OR^{21}$ (wherein $R^{21}$ represents hydrogen or a heterocycle)), and —CO—$NR^{22}R^{23}$ (wherein $R^{22}$ and $R^{23}$ each independently represents hydrogen, an alkyl group of 1 to 4 carbons, a benzyl group or a heterocycle); or $R^{4c}$ which represents an alkyl group of 1 to 4 carbons optionally substituted with 1 to 3 groups selected from the group consisting of halogens, cycloalkyl groups of 3 to 7 carbons, phenyl, naphthyl, heterocycles, —SH, —$OR^{16}$ (wherein $R^{16}$ represents hydrogen, an alkyl group of 1 to 4 carbons, a phenyl group, a naphthyl group, a benzyl group or a heterocycle), —O—CO—$R^{16}$ (wherein $R^{16}$ represents hydrogen, an alkyl group of 1 to 4 carbons, a phenyl group, a naphthyl group, a benzyl group or a heterocycle), —$NR^{17}R^{18}$ (wherein $R^{17}$ and $R^{18}$ each independently represents hydrogen, an alkyl group of 1 to 4 carbons, a heterocycle, an alkylsulfonyl group of 1 to 4 carbons, a phenylsulfonyl group, —$SO_2$-Het (wherein Het represents a heterocycle), an aminosulfonyl group, a methylaminosulfonyl group, a dimethylaminosulfonyl group, a diethylaminosulfonyl group, or an alkyl group of 1 to 4 carbons substituted with 1 or 2 groups selected from among phenyl, heterocycles, phenoxy, —O-Het (wherein Het represents a heterocycle) and hydroxyl, —NH—CO—$R^{19}$ (wherein $R^{19}$ represents hydrogen, an alkyl group of 1 to 4 carbons, a phenyl group, a naphthyl group, a benzyl group, a heterocycle, an alkoxy group of 1 to 4 carbons or a benzyloxy group), —CO—$R^{20}$ (wherein $R^{20}$ represents hydrogen, a heterocycle, an alkoxy group of 1 to 4 carbons, a phenoxy group, a benzyloxy group or —$OR^{21}$ (wherein $R^{21}$ represents hydrogen or a heterocycle)) and —CO—$NR^{22}R^{23}$ (wherein $R^{22}$ and $R^{23}$ each independently represents hydrogen, an alkyl group of 1 to 4 carbons, a benzyl group or a heterocycle); and the numbers in italics represents the positions on the benzofuran ring.

The present invention further provides pharmaceutical compositions comprising a therapeutically effective dose of the benzofuryl-α-pyrone derivatives represented by structural formula (I) above or their salts, with pharmaceutically acceptable carriers.

The invention still further provides lipid metabolism enhancers, triglyceride biosynthesis inhibitors, blood triglyceride lowering agents, blood HDL elevating agents, arteriosclerosis prophylactic agents and arteriosclerosis treatment agents containing as active ingredients the benzofuryl-α-pyrone derivatives represented by structural formula (I) above or their salts.

EMBODIMENT FOR CARRYING OUR THE INVENTION

The terms used alone or in conjunction with other terms throughout the present specification will now be explained. However, the invention is in no way restricted by the specific examples listed below.

"Alkyl" means a linear or branched alkyl group such as methyl, ethyl, n-propyl, isopropyl, n-butyl, isobutyl, sec-butyl, t-butyl, n-pentyl, isopentyl or 3-pentyl.

"Alkenyl" means a linear or branched alkenyl group such as vinyl, 1-propenyl, aryl, isopropenyl, 2-butenyl, 3-butenyl, 1-pentenyl or 2-pentenyl.

"Alkynyl" means a linear or branched alkynyl group such as ethynyl, 1-propynyl, 2-propynyl, 1-butynyl, 2-butynyl, 3-butynyl, 2-methyl-3-butynyl, 1-pentynyl, 2-pentynyl, 3-pentynyl or 4-pentynyl.

"Cycloalkyl" means a cycloalkyl group of 3 to 7 carbons such as cyclopropyl, cyclobutyl, cyclopentyl, cyclohexyl or cycloheptyl.

A "cycloalkyl group of 3 to 7 carbons-alkyl group of 1 to 5 carbons" is a group comprising the aforementioned cycloalkyl group of 3 to 7 carbons and alkyl group of 1 to 5 carbons, and for example, there may be mentioned cyclopropylmethyl, cyclopentylmethyl, cyclopentylethyl, cyclohexylmethyl, cyclohexylethyl and cycloheptylmethyl.

"Aryl" means an aromatic ring of 6 to 10 carbons such as phenyl or naphthyl.

A "heterocycle" is a heterocycle containing as constituents of the ring 1 to 4 hetero atoms selected from the group consisting of oxygen, nitrogen and sulfur, and it may be a 5- or 6-membered heteroaromatic group such as imidazolyl, thiazolyl, isothiazolyl, pyrazolyl, triazolyl, tetrazolyl, pyrrolyl, pyridyl, pyrimidinyl, pyrazinyl, pyridazinyl, triazinyl, furyl, thienyl, oxazolyl or isoxazolyl, or a 5- to 7-membered heteroalicyclic group such as thiazolidinyl, oxazolidinyl, imidazolidinyl, pyrrolidinyl, piperidyl, morpholinyl, piperazinyl, homopiperazinyl, tetrahydrofuryl, tetrahydropyranyl, dioxolanyl, dioxanyl, oxazinyl, thiazinyl, diazinyl or pyrazolidinyl; this also includes bicyclic groups condensed onto benzene, cycloalkyl groups of 3 to 7 carbons and other heteroaromatic rings or heteroalicyclic rings, the heteroaromatic ring or heteroalicyclic ring may also be optionally substituted, and when chemically possible, the nitrogen atom or sulfur atom may be in an oxidized form.

"Heteroaryl" means a heteroaromatic group of the heterocycles defined above.

"Aralkyl" represents a group of 7 to 20 carbons comprising the aforementioned alkyl group of 1 to 5 carbons and aryl group of 6 to 10 carbons, and for example, there may be mentioned benzyl, phenethyl, phenylpropyl, benzhydryl, trityl and naphthylmethyl.

"Alkoxy" means a linear or branched alkoxy group such as methoxy, ethoxy, n-propoxy, isopropoxy, n-butoxy, isobutoxy, sec-butoxy, t-butoxy, n-pentyloxy, isopentyloxy, 3-pentyloxy, 2,2-dimethylpropoxy, n-hexyloxy, 4-methylpentyloxy or 2-ethylbutoxy.

"Unsaturated alkoxy" means a linear or branched unsaturated alkoxy group such as vinyloxy, allyloxy, 2-propenyloxy, 2-propynyloxy, 2-methyl-2-propenyloxy, 1-butenyloxy, 2-butenyloxy, 3-butenyloxy, 2-butynyloxy, 2-pentenyloxy, 3-hexenyloxy, 5-hexenyloxy or 5-hexynyloxy.

"Aryloxy" means an aryloxy group of 6 to 10 carbons such as phenoxy or naphthyloxy.

"Aralkyloxy" represents a group comprising the aforementioned alkoxy group of 1 to 5 carbons and aryl group of 6 to 10 carbons, and for example, there may be mentioned benzyloxy, phenethyloxy, phenylpropoxy, trityloxy and naphthylmethyloxy.

"Cycloalkyloxy" means a cycloalkyloxy group of 3 to 7 carbons such as cyclopropyloxy, cyclobutyloxy, cyclopentyloxy, cyclohexyloxy or cycloheptyloxy.

"Acyl" means a linear or branched acyl group of 1 to 6 carbons such as formyl, acetyl, propionyl, n-butyryl, isobutyryl, n-valeryl, trimethylacetyl or 3,3,3-trimethylpropionyl.

"Arylcarbonyl" means an arylcarbonyl group of 7 to 11 carbons such as benzoyl or naphthylcarbonyl.

"Alkylsulfonyl" means an alkylsulfonyl group of 1 to 5 carbons such as methanesulfonyl, ethanesulfonyl or n-propanefulfonyl.

"Arylsulfonyl" means an arylsulfonyl group of 6 to 10 carbons such as phenylsulfonyl or naphthalenesulfonyl.

The rings of the "aryl", "phenyl", "naphthyl" and "heterocycle" may be substituted with 1 to 4 substituents selected from the group consisting of, for example, —OH, carboxyl, cyano, phenyl, heterocycles, —SO$_2$NH$_2$, —SO$_3$H, alkylsulfamoyl groups such as methylsulfamoyl, ethylsulfamoyl, dimethylsulfamoyl, etc., phenylsulfamoyl, benzylsulfamoyl, morpholinesulfonyl, alkylsulfonyl groups such as methanesulfonyl, ethanesulfonyl, n-propanesulfonyl, etc., arylsulfonyl groups such as phenylsulfonyl, naphthalenesulfonyl, etc., amino, methylenedioxy, alkoxy groups of 1 to 5 carbons such as methoxy, ethoxy, n-propoxy, isopropoxy, n-butoxy, isobutoxy, t-butoxy, n-pentyloxy, etc., alkylamino groups such as methylamino, dimethylamino, ethylamino, diethylamino, n-propylamino, isopropylamino, n-butylamino, isobutylamino, t-butylamino, etc., acylamino groups such as formamino, acetylamino, propionylamino, n-butyrylamino, etc., alkoxycarbonylamino groups such as methoxycarbonylamino, ethoxycarbonylamino, n-propoxycarbonylamino, n-butoxycarbonylamino, t-butoxycarbonylamino, etc., aralkyloxycarbonylamino groups such as benzyloxycarbonylamino, naphthylmethyloxycarbonylamino, etc., alkylsulfonylamino groups such as methanesulfonylamino, ethanesulfonylamino, n-propanesulfonylamino, etc., arylsulfonylamino groups such as phenylsulfonylamino, naphthalenesulfonylamino, etc., nitro, hydroxymethyl, alkyl groups of 1 to 5 carbons such as methyl, ethyl, n-propyl, isopropyl, n-butyl, isobutyl, t-butyl, n-pentyl, etc., aralkyl groups such as benzyl, phenethyl, trityl, naphthylmethyl, etc., aralkyloxy groups such as benzyloxy, phenethyloxy, phenylpropoxy, trityloxy, naphthylmethyloxy, etc., acyl groups such as formyl, acetyl, propionyl, n-butyryl, isobutyryl, n-valeryl, trimethylacetyl, 3,3,3-trimethylpropionyl, etc., alkoxycarbonyl groups such as methoxycarbonyl, ethoxycarbonyl, n-propoxycarbonyl, isopropoxycarbonyl, n-butoxycarbonyl, t-butoxycarbonyl, etc., aryloxycarbonyl groups such as phenoxycarbonyl, naphthyloxycarbonyl, etc., aralkyloxycarbonyl groups such as benzyloxycarbonyl, phenethyloxycarbonyl, trityloxycarbonyl, naphthylmethyloxycarbonyl, etc., carbamoyl, alkylcarbamoyl groups such as methylcarbamoyl, dimethylcarbamoyl, ethylcarbamoyl, diethylcarbamoyl, n-propylcarbamoyl, n-butylcarbamoyl, etc., halogenated methyl groups such as chloromethyl, bromomethyl, trifluoromethyl, etc., and halogen atoms, i.e. fluorine, chlorine, bromine and iodine; when chemically possible, these may be substituted with 1 to 3 oxo groups or thiooxo groups.

In formula (I) above, $R^1$ represents hydrogen or an alkyl group of 1 to 5 carbons. As alkyl groups of 1 to 5 carbons there may be mentioned, for example, methyl, ethyl, n-propyl, isopropyl, n-butyl, isobutyl, sec-butyl, t-butyl, n-pentyl, isopentyl and 3-pentyl.

As preferred groups for $R^1$ there may be mentioned hydrogen, methyl, ethyl and isopropyl, and methyl may be mentioned as a particularly preferred group for $R^1$.

In formula (I) above, $R^2$ represents hydrogen, —CO—$R^5$ (wherein $R^5$ represents hydrogen, an alkyl group of 1 to 5 carbons with optional substituents, a cycloalkyl group of 3 to 7 carbons, an aryl group of 6 to 10 carbons or a heterocycle), or —SO$_2$R$^6$ (wherein $R^6$ represents an optionally halogen-substituted alkyl group of 1 to 5 carbons, or an aryl group of 6 to 10 carbons).

When $R^2$ is —CO—$R^5$ and the $R^5$ group is an alkyl group of 1 to 5 carbons with an optional substituent, the alkyl group of 1 to 5 carbons for $R^5$ may be, for example, methyl, ethyl, n-propyl, isopropyl, n-butyl, isobutyl, sec-butyl, t-butyl, n-pentyl, isopentyl, 3-pentyl, etc., among which methyl, ethyl and isopropyl are preferred.

Optional substituents of the alkyl group of 1 to 5 carbons for $R^5$ include all alkyl group substituents known to those skilled in the art and, for example, they include halogen atoms, —OH, carboxyl groups, formyl groups, acyl groups, cyano groups, nitro groups, amino groups, mercapto groups, sulfonate groups, aryl groups of 6 to 10 carbons, heterocycles, cycloalkyl groups of 3 to 7 carbons and their protected forms; more specifically, there may be mentioned —OH; hydroxyl protected with an alkyl group of 1 to 4 carbons, an aryl group of 6 to 10 carbons, an aralkyl group of 7 to 20 carbons, a heterocycle, an acyl group of 1 to 5 carbons, an arylcarbonyl group of 7 to 11 carbons or an aralkylcarbonyl group of 8 to 21 carbons; —O—CO-Het (wherein Het represents a heterocycle); cycloalkyl groups of 3 to 7 carbons; aryl groups of 6 to 10 carbons; heterocycles; amino groups; amino groups protected with an alkyl group of 1 to 4 carbons, an aralkyl group of 7 to 20 carbons, an optionally halogen-substituted alkylsulfonyl group of 1 to 4 carbons, an arylsulfonyl group of 6 to 10 carbons, an acyl group of 1 to 5 carbons, an arylcarbonyl group of 7 to 11 carbons, an aralkylcarbonyl group of 8 to 21 carbons, an alkoxycarbonyl group of 2 to 5 carbons, an aralkyloxycarbonyl group of 8 to 21 carbons or a heterocycle; —NH—CO-Het (wherein Het represents a heterocycle); acyl groups of 1 to 5 carbons; carboxyl groups; alkoxycarbonyl groups of 2 to 5 carbons; aryloxycarbonyl groups of 7 to 11 carbons; aralkyloxycarbonyl groups of 8 to 21 carbons; —CO—O-Het (wherein Het represents a heterocycle); carbamoyl groups, alkylcarbamoyl groups of 2 to 5 carbons; aralkylcarbamoyl groups of 8 to 21 carbons; —CO—NH-Het (wherein Het represents a heterocycle); and —CO-Het (wherein Het represents a heterocycle). As preferred substituents among these there may be mentioned phenyl, aryloxy, amino, t-butoxycarbonylamino, benzyloxycarbonylamino, (benzyloxycarbonylamino) methylamino, acetylamino and morpholinylcarbonyl.

When $R^2$ is —COR$^5$ and the $R^5$ group is a cycloalkyl group of 3 to 7 carbons, the cycloalkyl group of 3 to 7 carbons for $R^5$ may be, for example, cyclopropyl, cyclobutyl, cyclopentyl, cyclohexyl, cycloheptyl, etc., among which cyclohexyl is preferred.

When $R^2$ is —COR$^5$ and the $R^5$ group is an aryl group of 6 to 10 carbons, the aryl group of 6 to 10 carbons for $R^5$ may be, for example, phenyl, naphthyl, etc., among which phenyl is preferred.

When $R^2$ is —COR$^5$ and the $R^5$ group is a heterocycle, the heterocycle for $R^5$ may be, for example, imidazolyl, thiazolyl, isothiazolyl, pyrazolyl, triazolyl, pyrrolyl, pyridyl, pyrimidinyl, pyrazinyl, furyl, thienyl, isoxazolyl, thiazolidinyl, oxazolidinyl, imidazolidinyl, pyrrolidinyl, piperidyl, morpholinyl, piperazinyl, tetrahydrofuryl, tetrahydropyranyl, etc., among which pyridyl, pyrrolidinyl and furyl are preferred.

As preferred groups for $R^5$ there may be mentioned alkyl groups of 1 to 5 carbons with optional substituents, among which there may be mentioned methyl, methyl or ethyl substituted with phenyl, aryloxy, amino, t-butoxycarbonylamino, benzyloxycarbonylamino, (benzyloxycarbonyl)-N-methylamino, acetylamino or morpholinylcarbonyl, and isopropyl; aryl groups of 6 to 10 carbons, among which there may be mentioned phenyl; and heterocycles, among which there may be mentioned pyridyl, pyrrolidinyl and furyl.

When $R^2$ is —$SO_2R^6$ and the $R^6$ group is an optionally halogen-substituted alkyl group of 1 to 5 carbons, the optionally halogen-substituted alkyl group of 1 to 5 carbons for $R^6$ may be, for example, methyl, ethyl, n-propyl, isopropyl, n-butyl, isobutyl, sec-butyl, t-butyl, n-pentyl, chloromethyl, bromomethyl, trifluoromethyl, etc., among which methyl and trifluoromethyl are preferred.

When $R^2$ is —$SO_2R^6$ and $R^6$ is an aryl group of 6 to 10 carbons, the aryl group of 6 to 10 carbons for $R^6$ may be, for example, phenyl, naphthyl, etc., among which phenyl is preferred.

As preferred groups for $R^6$ there may be mentioned optionally halogen-substituted alkyl groups of 1 to 5 carbons, and as particularly preferred groups for $R^6$ there may be mentioned methyl and trifluoromethyl.

As preferred groups for $R^2$ there may be mentioned hydrogen, —$COR^{70}$ (wherein $R^{70}$ represents an alkyl group of 1 to 5 carbons with an optional substituent, an aryl group of 6 to 10 carbons or a heterocycle) and optionally halogen-substituted alkylsulfonyl groups of 1 to 5 carbons, and as particularly preferred groups for $R^2$ there may be mentioned hydrogen, —$COR^{71}$ (wherein $R^{71}$ represents s methyl group; a methyl or ethyl group substituted with phenyl, aryloxy, amino, t-butoxycarbonylamino, benzyloxycarbonylamino, (benzyloxycarbonyl)-N-methylamino, acetylamino or morpholinylcarbonyl; an isopropyl group; a phenyl group; a pyridyl group; a pyrrolidinyl group; or a furyl group), methanesulfonyl and trifluoromethanesulfonyl.

In formula (I) above, $R^3$ represents hydrogen, an alkyl group of 1 to 5 carbons, an alkenyl group of 2 to 5 carbons, an alkynyl group of 2 to 5 carbons, a cycloalkyl group of 3 to 7 carbons, a cycloalkyl of 3 to 7 carbons-alkyl group of 1 to 5 carbons, an aryl group of 6 to 10 carbons, an aralkyl group of 7 to 20 carbons, an alkoxy group of 1 to 5 carbons or an aryloxy group of 6 to 10 carbons.

When $R^3$ is an alkyl group of 1 to 5 carbons, the alkyl group of 1 to 5 carbons may be, for example, methyl, ethyl, n-propyl, isopropyl, n-butyl, isobutyl, sec-butyl, t-butyl, n-pentyl, etc., among which methyl, ethyl, isopropyl and n-pentyl are preferred.

When $R^3$ is an alkenyl group of 2 to 5 carbons, the alkenyl group of 2 to 5 carbons may be vinyl, allyl, 1-propenyl, isopropenyl, 2-butenyl, 3-butenyl, 1-pentenyl, 2-pentenyl, etc., among which 2-butenyl is preferred.

When $R^3$ is an alkynyl group of 2 to 5 carbons, the alkylnyl group of 2 to 5 carbons may be ethynyl, 2-propynyl, 1-propynyl, isopropynyl, 2-butynyl, 3-butynyl, 1-pentynyl, 2-pentynyl, etc., among which 2-butynyl is preferred.

When $R^3$ is a cycloalkyl group of 3 to 7 carbons, the cycloalkyl group of 3 to 7 carbons may be, for example, cyclopropyl, cyclobutyl, cyclopentyl, cyclohexyl, cycloheptyl, etc., among which cyclohexyl is preferred.

When $R^3$ is a cycloalkyl of 3 to 7 carbons-alkyl group of 1 to 5 carbons, the cycloalkyl of 3 to 7 carbons-alkyl group of 1 to 5 carbons may be, for example, cyclopropylmethyl, cyclobutylmethyl, cyclopentylmethyl, cyclohexylmethyl, cycloheptylmethyl, etc., among which cyclopentylmethyl is preferred.

When $R^3$ is an aryl group of 6 to 10 carbons, the aryl group of 6 to 10 carbons may be, for example, phenyl, naphthyl, etc., among which phenyl is preferred.

When $R^3$ is an aralkyl group of 7 to 20 carbons, the aralkyl group of 7 to 20 carbons may be, for example, benzyl, phenethyl, phenylpropyl, benzhydryl, trityl, naphthylmethyl, etc., among which benzyl is preferred.

When $R^3$ is an alkoxy group of 1 to 5 carbons, the alkoxy group of 1 to 5 carbons may be, for example, methoxy, ethoxy, n-propoxy, isopropoxy, n-butoxy, isobutoxy, sec-butoxy, t-butoxy, etc., among which methoxy is preferred.

When $R^3$ is an aryloxy group of 6 to 10 carbons, the aryloxy group of 6 to 10 carbons may be, for example, phenoxy, naphthyloxy, etc., among which phenoxy is preferred.

As preferred groups for $R^3$ there may be mentioned alkyl groups of 1 to 5 carbons, alkenyl groups of 2 to 5 carbons, cycloalkyl groups of 3 to 7 carbons-alkyl groups of 1 to 5 carbons and aralkyl groups of 7 to 20 carbons, and as particularly preferred groups for $R^3$ there may be mentioned alkyl groups of 1 to 5 carbons, among which methyl, ethyl, isopropyl and n-pentyl are preferred; cycloalkyl groups of 3 to 7 carbons-alkyl groups of 1 to 5 carbons, among which cyclopentylmethyl is preferred; and benzyl.

In formula (I) above, $R^4$ is a substituent at the C-4 position, C-5 position, C-6 position or C-7 position of the benzofuran ring and represents:

$R^{4a}$ which represents hydrogen, a nitro group, a cyano group, a halogen atom, a heterocycle, an alkenyl group of 2 to 5 carbons, an alkynyl group of 2 to 5 carbons, an aryl group of 6 to 10 carbons, A=CH(CH$_2$)$_n$— (wherein A represents an alicyclic heterocycle, "=" represents a double bond and n represents 0, 1 or 2), A=CH(CH$_2$)$_m$O— (wherein A represents an alicyclic heterocycle, "=" represents a double bond and m represents 1, 2 or 3), A—SO$_2$—(CH$_2$)$_m$— (wherein A represents an alicyclic heterocycle and m represents 1, 2 or 3), —OR$^7$ (wherein R$^7$ represents hydrogen, a cycloalkyl group of 3 to 7 carbons, an aryl group of 6 to 10 carbons, a heterocycle or an optionally halogen-substituted alkylsulfonyl group of 1 to 4 carbons or arylsulfonyl group of 6 to 10 carbons), —O—CO—R$^8$ (wherein R$^8$ represents hydrogen, an alkyl group of 1 to 4 carbons, an aryl group of 6 to 10 carbons, an aralkyl group of 7 to 20 carbons or a heterocycle), —NR$^9$R$^{10}$ (wherein R$^9$ and R$^{10}$ each independently represents hydrogen, an alkyl group of 1 to 4 carbons, an aralkyl group of 7 to 20 carbons, a phenyl group, a heterocycle, —SO$_2$—R$^{11}$ (wherein R$^{11}$ represents an optionally halogen-substituted alkyl group of 1 to 12 carbons, a heterocycle-substituted alkyl group of 1 to 6 carbons, an aryl group of 6 to 10 carbons, a heterocycle or an aralkyl group of 7 to 20 carbons) or —CO—R$^{12}$ (wherein R$^{12}$ represents hydrogen, an alkyl group of 1 to 12 carbons, an, aryl group of 6 to 10 carbons, an aralkyl group of 7 to 20 carbons, a heterocycle, an alkoxy group of 1 to 10 carbons, a heterocycle-substituted alkyl group of 1 to 6 carbons, an aryloxy group of 6 to 10 carbons, a heteroaryloxy group or an aralkyloxy group of 7 to 20 carbons)), —CO—$R^{13}$ (wherein $R^{13}$ represents hydrogen, —OH, an alkyl group of 1 to 4 carbons, an aryl group of 6 to 10 carbons, a heterocycle, an alkoxy group of 1 to 4 carbons, an aryloxy group of 6 to 10 carbons or an aralkyloxy group of 7 to 20 carbons) or —CO—$NR^{14}R^{15}$ (wherein $R^{14}$ and $R^{15}$ each independently represents hydrogen, an alkyl group of 1 to 4 carbons, a cycloalkyl group of 3 to 7 carbons, an aryl group of 6 to 10 carbons, an aralkyl group of 7 to 20 carbons, a heterocycle or a heterocycle-substituted alkyl group of 1 to 4 carbons);

$R^{4b}$ which represents a saturated or unsaturated alkoxy group of 1 to 6 carbons optionally substituted with 1 to 3 groups selected from the group consisting of halogens, cycloalkyl groups of 3 to 7 carbons, phenyl, naphthyl, heterocycles, —$OR^{16}$ (wherein $R^{16}$ represents hydrogen, an alkyl group of 1 to 4 carbons, a phenyl group, a naphthyl group, a benzyl group or a heterocycle), —O—CO—$R^{16}$ (wherein $R^{16}$ represents hydrogen, an alkyl group of 1 to 4 carbons, a phenyl group, a naphthyl group, a benzyl group or a heterocycle), —$NR^{17}R^{18}$ (wherein $R^{17}$ and $R^{18}$ each independently represents hydrogen, an alkyl group of 1 to 4 carbons, a heterocycle, an alkylsulfonyl group of 1 to 4 carbons, a phenylsulfonyl group, —$SO_2$-Het (wherein Het represents a heterocycle), an aminosulfonyl group, a methylaminosulfonyl group, a dimethylaminosulfonyl group, a diethylaminosulfonyl group, or an alkyl group of 1 to 4 carbons substituted with 1 or 2 groups selected from among phenyl, heterocycles, phenoxy, —O-Het (wherein Het represents a heterocycle) and hydroxyl, —NH—CO—$R^{19}$ (wherein $R^{19}$ represents hydrogen, an alkyl group of 1 to 4 carbons, a phenyl group, a naphthyl group, a benzyl group, a heterocycle, an alkoxy group of 1 to 4 carbons or a benzyloxy group), —CO—$R^{20}$ (wherein $R^{20}$ represents hydrogen, a heterocycle, an alkoxy group of 1 to 4 carbons, a phenoxy group, a benzyloxy group or —$OR^{21}$ (wherein $R^{21}$ represents hydrogen or a heterocycle)) and —CO—$NR^{22}R^{23}$ (wherein $R^{22}$ and $R^{23}$ each independently represents hydrogen, an alkyl group of 1 to 4 carbons, a benzyl group or a heterocycle); or $R^{4c}$ which represents an alkyl group of 1 to 4 carbons optionally substituted with 1 to 3 groups selected from the group consisting of halogens, cycloalkyl groups of 3 to 7 carbons, phenyl, naphthyl, heterocycles, —SH, —$OR^{16}$ (wherein $R^{16}$ represents hydrogen, an alkyl group of 1 to 4 carbons, a phenyl group, a naphthyl group, a benzyl group or a heterocycle), —O—CO—$R^{16}$ (wherein $R^{16}$ represents hydrogen, an alkyl group of 1 to 4 carbons, a phenyl group, a naphthyl group, a benzyl group or a heterocycle), —$NR^{17}R^{18}$ (wherein $R^{17}$ and $R^{18}$ each independently represents hydrogen, an alkyl group of 1 to 4 carbons, a heterocycle, an alkylsulfonyl group of 1 to 4 carbons, a phenylsulfonyl group, —$SO_2$-Het (wherein Het represents a heterocycle), an aminosulfonyl group, a methylaminosulfonyl group, a dimethylaminosulfonyl group, a diethylaminosulfonyl group, or an alkyl group of 1 to 4 carbons substituted with 1 or 2 groups selected from among phenyl, heterocycles, phenoxy, —O-Het (wherein Het represents a heterocycle) and hydroxyl, —NH—CO—$R^{19}$ (wherein $R^{19}$ represents hydrogen, an alkyl group of 1 to 4 carbons, a phenyl group, a naphthyl group, a benzyl group, a heterocycle, an alkoxy group of 1 to 4 carbons or a benzyloxy group), —CO—$R^{20}$ (wherein $R^{20}$ represents hydrogen, a heterocycle, an alkoxy group of 1 to 4 carbons, a phenoxy group, a benzyloxy group or —$OR^{21}$ (wherein $R^{21}$ represents hydrogen or a heterocycle)) and —CO—$NR^{22}R^{23}$ (wherein $R^{22}$ and $R^{23}$ each independently represents hydrogen, an alkyl group of 1 to 4 carbons, a benzyl group or a heterocycle).

When $R^4$ is $R^{4a}$, there may be mentioned as specific examples of $R^{4a}$, hydrogen; nitro; cyano; halogen atoms such as fluorine, chlorine, bromine and iodine; heterocycles such as imidazolyl, thiazolyl, isothiazolyl, pyrazolyl, triazolyl, pyrrolyl, pyridyl, pyrimidinyl, pyrazinyl, furyl, thienyl, isoxazolyl, thiazolidinyl, oxazolidinyl, imidazolidinyl, 6-oxo-4,5-benzo-1,3-oxazin-2-yl, 1-oxoisoindolin-2-yl, pyrrolidinyl, 2,5-dioxopyrrolidinyl, piperidyl, 2,6-dioxopiperidyl, 1-(4-bromobenzoyl)piperidin-4-yl, morpholinyl, piperazinyl, 2,3-dioxopiperazinyl, homopiperazinyl, tetrahydrofuryl and tetrahydropyranyl; alkenyl groups such as vinyl, allyl, 1-propenyl, isopropenyl, 2-butenyl, 3-butenyl, 1-pentenyl and 2-pentenyl; alkynyl groups such as ethynyl, 1-propynyl, 2-propynyl, 1-butynyl, 2-butynyl, 3-butynyl, 2-methyl-3-butynyl, 1-pentynyl, 2-pentynyl, 3-pentynyl and 4-pentynyl; aryl groups such as phenyl and naphthyl; hydroxyl; cycloalkyloxy groups such as cyclopropyloxy, cyclobutyloxy, cyclopentyloxy, cyclohexyloxy and cycloheptyloxy; aryloxy groups such as phenoxy and naphthyloxy; groups represented by —O-Het (wherein Het represents a heterocycle), such as imidazolyloxy, thiazolyloxy, isothiazolyloxy, pyrazolyloxy, triazolyloxy, pyrrolyloxy, pyridyloxy, pyrimidinyloxy, pyrazinyloxy, furyloxy, thienyloxy, isoxazolyloxy, thiazolidinyloxy, oxazolidinyloxy, imidazolidinyloxy, pyrrolidinyloxy, piperidyloxy, morpholinyloxy, piperazinyloxy, tetrahydrofuryloxy and tetrahydropyranyloxy; optionally halogen-substituted alkylsulfonyloxy groups such as methanesulfonyloxy, ethanesulfonyloxy, n-propanesulfonyloxy and trifluoromethanesulfonyloxy; arylsulfonyloxy groups such as phenylsulfonyloxy and naphthalenesulfonyloxy; acyloxy groups such as formyloxy, acetyloxy, propionyloxy, butyryloxy, isobutyryloxy and trimethylacetyloxy; arylcarboxy groups such as benzoyloxy and naphthylcarboxy; aralkylcarboxy groups such as phenylacetyloxy, 2-phenylpropionyloxy, 3-phenylbutyryloxy, diphenylacetyloxy and naphthylacetyloxy; groups represented by —O—CO-Het (wherein Het represents a heterocycle), such as imidazolylcarboxy, thiazolylcarboxy, isothiazolylcarboxy, pyrazolylcarboxy, triazolylcarboxy, pyrrolylcarboxy, pyridylcarboxy, pyrimidinylcarboxy, pyrazinylcarboxy, furylcarboxy, thienylcarboxy, isoxazolylcarboxy, thiazolidinylcarboxy, oxazolidinylcarboxy, imidazolidinylcarboxy, pyrrolidinylcarboxy, piperidylcarboxy, morpholinylcarboxy, piperazinylcarboxy, tetrahydrofurylcarboxy and tetrahydropyranylcarboxy; amino; alkylamino groups such as methylamino, dimethylamino, ethylamino, diethylamino, propylamino, dipropylamino, isopropylamino, diisopropylamino and dibutylamino; aralkylamino groups such as benzylamino and dibenzylamino; heterocycle-substituted amino groups such as imidazolylamino, N-methyl-N-imidazolylamino, thiazolylamino, N-methyl-N-thiazolylamino, isothiazolylamino, pyrazolylamino, triazolylamino, N-methyl-N-triazolylamino, pyrrolylamino, pyridylamino, N-methyl-N-pyridylamino, dipyridylamino, pyrimidinylamino, pyrazinylamino, furylamino, thienylamino, isoxazolylamino, thiazolidinylamino, oxazolidinylamino, imidazolidinylamino, pyrrolidinylamino, N-methyl-N-pyrrolidinylamino, piperidylamino, morpholinylamino, N-methyl-N-morpholinylamino, tetrahydrofurylamino and tetrahydropyranylamino; optionally halogen-substituted alkylsulfonylamino groups such as methanesulfonylamino, N-methyl-N-methanesulfonylamino, ethanesulfonylamino, n-propanesulfonylamino and trifluoromethanesulfonylamino; arylsulfonylamino groups such as phenylsulfonylamino, N-methyl-N-phenylsulfonylamino, N-(4-chlorophenylsulfonyl)-N-methylamino and naphthalenesulfonylamino; acylamino groups such as formylamino, acetylamino, N-methyl-N-acetylamino, propionylamino, butyrylamino, isobutyrylamino, N-methyl-N-isobutyrylamino and trimethylacetylamino; arylcarbonylamino groups such as benzoylamino, N-methyl-N-benzoylamino and naphthylcarbonylamino; aralkylcarbonylamino groups such as phenylacetylamino, N-methyl-N-phenylacetylamino, 2-phenylpropionylamino, 3-phenylbutyrylamino, diphenylacetylamino and naphthylacetylamino; amino groups substituted with a group represented by —CO-Het (wherein Het represents a heterocycle), such as imidazolylcarbonylamino, N-methyl-N-imidazolylcarbonylamino, thiazolylcarbonylamino, N-methyl-N-thiazolylcarbonylamino, pyridylcarbonylamino, N-methyl-N-pyridylcarbonylamino, pyrimidinylcarbonylamino, N-methyl-N-pyrimidinylcarbonylamino, pyrazinylcarbonylamino, N-methyl-N-pyrazinylcarbonylamino, furylcarbonylamino, thienylcarbonylamino, N-methyl-N-thienylcarbonylamino, N-methyl-N-oxazolylcarbonylamino, N-methyl-N-tetrazolylcarbonylamino, thiazolidinylcarbonylamino, oxazolidinylcarbonylamino, imidazolidinylcarbonylamino, pyrrolidinylcarbonylamino and piperidylcarbonylamino; alkoxycarbonylamino groups such as methoxycarbonylamino, ethoxycarbonylamino, n-propoxycarbonylamino, isopropoxycarbonylamino, t-butoxycarbonylamino and N-methyl-N-(t-butoxycarbonyl) amino; aryloxycarbonylamino groups such as phenoxycarbonylamino and naphthyloxycarbonylamino; aralkyloxycarbonylamino groups such as benzyloxycarbonylamino, phenethyloxycarbonylamino, phenylpropoxycarbonylamino, benzhydryloxycarbonylamino and naphthylmethoxycarbonylamino; formyl; carboxyl; alkoxycarbonyl groups such as methoxycarbonyl, ethoxycarbonyl, n-propoxycarbonyl, isopropoxycarbonyl and t-butoxycarbonyl; aryloxycarbonyl groups such as phenoxycarbonyl and naphthyloxycarbonyl; aralkyloxycarbonyl groups such as benzyloxycarbonyl, phenethyloxycarbonyl, phenylpropoxycarbonyl, benzhydryloxycarbonyl and naphthylmethoxycarbonyl; acyl groups such as acetyl, propionyl, butyryl and isobutyryl; arylcarbonyl groups such as benzoyl and naphthylcarbonyl; groups represented by —CO-Het (wherein Het represents a heterocycle), such as imidazolylcarbonyl, thiazolylcarbonyl, isothiazolylcarbonyl, pyrazolylcarbonyl, triazolylcarbonyl, pyrrolylcarbonyl, pyridylcarbonyl, pyrimidinylcarbonyl, pyrazinylcarbonyl, furylcarbonyl, thienylcarbonyl, isoxazolylcarbonyl, thiazolidinylcarbonyl, oxazolidinylcarbonyl, imidazolidinylcarbonyl, pyrrolidinylcarbonyl, piperidylcarbonyl, morpholinylcarbonyl, piperazinylcarbonyl and 1,3,4-trihydroisoquinon-2-ylcarbonyl; carbamoyl groups such as carbamoyl, methylcarbamoyl, dimethylcarbamoyl, ethylcarbamoyl, diethylcarbamoyl, propylcarbamoyl, dipropylcarbamoyl, cyclopropylcarbamoyl, cyclopentylcarbamoyl, cyclohexylcarbamoyl, phenylcarbamoyl, 4-bromo-2-cyanophenylcarbamoyl, N-methyl-N-phenylcarbamoyl, benzylcarbamoyl, N-benzyl-N-methylcarbamoyl, N-methyl-N-phenethylcarbamoyl, dibenzylcarbamoyl, imidazolylcarbamoyl, N-imidazolyl-N-methylcarbamoyl, N-benzimidazolyl-N-methylcarbamoyl, thiazolylcarbamoyl, N-methyl-N-thiazolylcarbamoyl, benzothiazolylcarbamoyl, N-benzothiazolyl-N-methylcarbamoyl, isothiazolylcarbamoyl, oxazolylcarbamoyl, N-methyl-N-oxazolylcarbamoyl, benzoxazolylcarbamoyl, N-benzoxazolyl-N-methylcarbamoyl, pyrazolylcarbamoyl, triazolylcarbamoyl, pyrrolylcarbamoyl, pyridylcarbamoyl, N-methyl-N-pyridylcarbamoyl, N-methyl-N-(pyridylmethyl)carbamoyl, pyrimidinylcarbamoyl, pyrazinylcarbamoyl, furylcarbamoyl, thienylcarbamoyl, isoxazolylcarbamoyl, thiazolidinylcarbamoyl, oxazolidinylcarbamoyl, imidazolidinylcarbamoyl, pyrrolidinylcarbamoyl, piperidylcarbamoyl, tetrahydrofurylcarbamoyl and tetrahydropyranylcarbamoyl; groups represented by A=CH(CH$_2$)n— (wherein A represents an alicyclic heterocycle, "=" represents a double bond and n represents 0, 1, or 2), such as (3,5-dioxo-2,4-thiazolidinylidene)methyl, (3,5-dioxo-2,4-oxazolidinylidene)methyl, (2,5-dioxoimidazolidin-4-ylidene)methyl, (5-oxo-3-thioxo-2,4-thiazolidinylidene) methyl, (2,4,6-trioxo-3,5-diazaperhydroinylidene)methyl and (3,5-dimethyl-2,4,6-trioxo-3,5-diazaperhydroinylidene) methyl; groups represented by A=CH(CH$_2$)$_m$O— (wherein A represents an alicyclic heterocycle, "=" represents a double bond and m represents 1, 2, or 3), such as 2-(3,5-dioxo-2,4thiazolidinylidene)ethoxy, 2-(3,5-dioxo-2,4-oxazolidinylidene)ethoxy, 2-(2,5-dioxoimidazolidin-4-ylidene)ethoxy, 2-(5-oxo-3-thioxo-2,4-thiazolidinylidene)ethoxy, 2-(2,4,6-trioxo-3,5-diazaperhydroinylidene)ethoxy and 2-(3,5-dimethyl-2,4,6-trioxo-3,5-diazaperhydroinylidene)ethoxy; and groups represented by A—SO$_2$—(CH$_2$)$_m$— (wherein A represents an alicyclic heterocycle and m represents 1, 2, or 3), such as (3,5-dioxo-2,4-thiazolidinyl)sulfonylmethyl, (3,5-dioxo-2,4-oxazolidinyl)sulfonylmethyl, (2,5-dioxoimidazolidin-4-yl) sulfonylmethyl, and (5-oxo-3-thioxo-2,4-thiazolidinyl) sulfonylmethyl.

As preferred groups for $R^{4a}$ there may be specifically mentioned, for example, hydrogen, nitro, cyano, bromine, imidazolyl, thiazolyl, pyridyl, pyrimidinyl, furyl, thienyl, morpholinyl, piperazinyl, hydroxyl, pyrrolidinyloxy, piperidyloxy, methanesulfonyloxy, trifluoromethanesulfonyloxy, phenylsulfonyloxy, acetyloxy, benzoyloxy, imidazolylcarboxy, thiazolylcarboxy, pyridylcarboxy, pyrimidinylcarboxy, pyrazinylcarboxy, dimethylamino, ethylamino, diethylamino, dibenzylamino, imidazolylamino, thiazolylamino, pyridylamino, pyrimidinylamino, N-methyl-N-methanesulfonylamino, phenylsulfonylamino, N-methyl-N-phenylsulfonylamino, N-methyl-N-acetylamino, N-methyl-N-isobutyrylamino, N-methyl-N-benzoylamino, N-methyl-N-phenylacetylamino, N-methyl-N-imidazolylcarbonylamino, N-methyl-N-thiazolylcarbonylamino, N-methyl-N-thienylcarbonylamino, N-methyl-N-oxazolylcarbonylamino, N-methyl-N-tetrazolylcarbonylamino, N-methyl-N-pyridylcarbonylamino, N-methyl-N-pyrazinylcarbonylamino, N-methyl-N-pyrimidinylcarbonylamino, N-methyl-N-(t-butoxycarbonyl) amino, dimethylcarbamoyl, cyclohexylcarbamoyl, phenylcarbamoyl, N-methyl-N-phenylcarbamoyl, N-benzyl-N-methylcarbamoyl, imidazolylcarbamoyl, benzimidazolylcarbamoyl, thiazolylcarbamoyl, N-methyl-N-thiazolylcarbamoyl, benzothiazolylcarbamoyl, isothiazolylcarbamoyl, pyrazolylcarbamoyl, triazolylcarbamoyl, pyrrolylcarbamoyl, pyridylcarbamoyl, N-methyl-N-pyridylcarbamoyl, pyrimidinylcarbamoyl, pyrazinylcarbamoyl, isoxazolylcarbamoyl, piperidylcarbamoyl, 1,3,4-trihydroisoquinolin-2-ylcarbonyl, formyl, carboxyl, methoxycarbonyl, ethoxycarbonyl, n-propoxycarbonyl, isopropoxycarbonyl, t-butoxycarbonyl, acetyl, benzoyl, (3,5-dioxo-2,4-thiazolidinylidene)methyl, (3,5-dioxo-2,4-oxazolidinylidene)methyl, (2,5-dioxoimidazolidin-4-ylidene)methyl, (5-oxo-3-thioxo-2,4-thiazolidinylidene)methyl, 2-(3,5-dioxo-2,4-thiazolidinylidene)ethoxy, 2-(3,5-dioxo-2,4-oxazolidinylidene)ethoxy, 2-(2,5-dioxoimidazolidin-4-ylidene)ethoxy, 2-(5-oxo-3-thioxo-2,4-thiazolidinylidene)ethoxy, (3,5-dioxo-2,4-thiazolidinyl)sulfonylmethyl, (3,5-dioxo-2,4-oxazolidinyl)sulfonylmethyl, (2,5-dioxoimidazolidin-4-yl)sulfonylmethyl and (5-oxo-3-thioxo-2,4-thiazolidinyl)sulfonylmethyl.

As particularly preferred groups for $R^{4a}$ there may be specifically mentioned, for example, hydrogen, nitro, cyano, bromine, thienyl, piperazinyl, trifluoromethanesulfonyloxy, phenylsulfonyloxy, acetyloxy, dimethylamino, dibenzylamino, N-methyl-N-methanesulfonylamino, N-methyl-N-phenylsulfonylamino, N-methyl-N-acetylamino, N-methyl-N-isobutyrylamino, N-methyl-N-benzoylamino, N-methyl-N-phenylacetylamino, N-methyl-N-thienylcarbonylamino, N-methyl-N-oxazolylcarbonylamino, N-methyl-N-thiazolylcarbonylamino, N-methyl-N-pyridylcarbonylamino, thiazolylcarbamoyl, benzothiazolylcarbamoyl, benzimidazolylcarbamoyl, N-methyl-N-phenylcarbamoyl, 1,3,4-trihydroisoquinolin-2-ylcarbonyl, methoxycarbonyl, isopropoxycarbonyl, and (3,5-dioxo-2,4-thiazolidinylidene)methyl.

When $R^4$ is $R^{4b}$, there may be mentioned as specific examples of substituents on the alkoxy groups of 1 to 4 carbons for $R^{4a}$, for example, halogen atoms such as fluorine, chlorine, bromine and iodine; cycloalkyl groups of 3 to 7 carbons such as cyclopropyl, cyclobutyl, cyclopentyl, cyclohexyl and cycloheptyl; aryl groups of 6 to 10 carbons such as phenyl, aminophenyl and naphthyl; heterocycles such as imidazolyl, N-tosylimidazolyl, thiazolyl, 2-(morpholinesulfonyl)thiazolyl, isothiazolyl, pyrazolyl, triazolyl, tetrazolyl, pyrrolyl, pyridyl, 2-methoxypyridyl, 5-hydroxypyridyl, pyrimidinyl, pyrazinyl, pyridazinyl, triazinyl, furyl, thienyl, 2-(morpholinesulfonyl)thienyl, oxazolyl, 2-phenyloxazolyl, isoxazolyl, thiazolidinyl, oxazolidinyl, imidazolidinyl, pyrrolidinyl, piperidyl, morpholinyl, piperazinyl, tetrahydrofuryl, tetrahydropyranyl and dioxolanyl; —OH; alkoxy groups of 1 to 4 carbons such as methoxy, ethoxy, n-propoxy, isopropoxy, n-butoxy, isobutoxy, sec-butoxy, t-butoxy, n-pentyloxy, isopentyloxy, 3-pentyloxy, 2,2-dimethylpropoxy, n-hexyloxy, 4-methylpentyloxy and 2-ethylbutoxy; aryloxy groups of 6 to 10 carbons such as phenoxy and naphthyloxy; benzyloxy; groups represented by —O-Het (wherein Het represents a heterocycle), such as pyridyloxy and piperidyloxy; acyloxy groups of 1 to 5 carbons such as formyloxy, acetyloxy, propionyloxy, butyryloxy, isobutyryloxy and trimethylacetyloxy; arylcarboxy groups of 7 to 11 carbons such as benzoyloxy and naphthylcarboxy; phenylacetyloxy; groups represented by —O—CO-Het (wherein Het represents a heterocycle), such as imidazolylcarboxy, thiazolylcarboxy, isothiazolylcarboxy, pyrazolylcarboxy, triazolylcarboxy, pyrrolylcarboxy, pyridylcarboxy, pyrimidinylcarboxy, pyrazinylcarboxy, furylcarboxy, thienylcarboxy, isoxazolylcarboxy, thiazolidinylcarboxy, oxazolidinylcarboxy, imidazolidinylcarboxy, pyrrolidinylcarboxy, piperidylcarboxy, morpholinylcarboxy, piperazinylcarboxy, tetrahydrofurylcarboxy and tetrahydropyranylcarboxy; amino; monosubstituted or disubstituted amino groups such as methylamino, dimethylamino, ethylamino, diethylamino, propylamino, dipropylamino, isopropylamino, diisopropylamino, dibutylamino, benzylamino, dibenzylamino, 2-hydroxy-2-phenethylamino, 2-hydroxy-3-phenoxypropylamino, imidazolylamino, thiazolylamino, isothiazolylamino, pyrazolylamino, triazolylamino, pyrrolylamino, pyridylamino, dipyridylamino, pyrimidinylamino, pyrazinylamino, furylamino, thienylamino, isoxazolylamino, thiazolidinylamino, oxazolidinylamino, imidazolidinylamino, pyrrolidinylamino, piperidylamino, tetrahydrofurylamino and tetrahydropyranylamino; optionally halogen-substituted alkylsulfonylamino groups of 1 to 4 carbons such as methanesulfonylamino, ethanesulfonylamino, n-propanesulfonylamino and trifluoromethanesulfonylamino; phenylsulfonylamino; acylamino groups of 1 to 5 carbons such as dimethylaminosulfonylamino, methylaminosulfonylamino, formylamino, acetylamino, propionylamino, butyrylamino, isobutyrylamino and trimethylacetylamino; arylcarbonylamino groups of 7 to 11 carbons such as benzoylamino and naphthylcarbonylamino; phenylacetylamino; groups represented by —NH—CO-Het (wherein Het represents a heterocycle), such as imidazolylcarbonylamino, thiazolylcarbonylamino, isoxazolylcarbonylamino, pyridylcarbonylamino, pyrimidinylcarbonylamino, pyrazinylcarbonylamino, furylcarbonylamino, thienylcarbonylamino, pyrrolidinylcarbonylamino, piperidylcarbonylamino and morpholinylcarbonylamino; alkoxycarbonylamino groups of 2 to 5 carbons such as methoxycarbonylamino, ethoxycarbonylamino, n-propoxycarbonylamino, isopropoxycarbonylamino and t-butoxycarbonylamino; benzyloxycarbonylamino; formyl; carboxy; alkoxycarbonyl groups of 2 to 5 carbons such as methoxycarbonyl, ethoxycarbonyl, n-propoxycarbonyl, isopropoxycarbonyl and t-butoxycarbonyl; phenoxycarbonyl; benzyloxycarbonyl; acyl groups of 2 to 5 carbons such as acetyl, propionyl, butyryl and isobutyryl; groups represented by —CO-Het (wherein Het represents a heterocycle) such as imidazolylcarbonyl, thiazolylcarbonyl, isothiazolylcarbonyl, pyrazolylcarbonyl, triazolylcarbonyl, pyrrolylcarbonyl, pyridylcarbonyl, pyrimidinylcarbonyl, pyrazinylcarbonyl, furylcarbonyl, thienylcarbonyl, isoxazolylcarbonyl, thiazolidinylcarbonyl, oxazolidinylcarbonyl, imidazolidinylcarbonyl, pyrrolidinylcarbonyl, piperidylcarbonyl, morpholinylcarbonyl and piperazinylcarbonyl; groups represented by —CO—O-Het (wherein Het represents a heterocycle), such as pyridyloxycarbonyl and piperidyloxycarbonyl; and carbamoyl groups such as carbamoyl, methylcarbamoyl, dimethylcarbamoyl, ethylcarbamoyl, diethylcarbamoyl, propylcarbamoyl, dipropylcarbamoyl, benzylcarbamoyl, dibenzylcarbamoyl, imidazolylcarbamoyl, thiazolylcarbamoyl, isothiazolylcarbamoyl, pyrazolylcarbamoyl, triazolylcarbamoyl, pyrrolylcarbamoyl, pyridylcarbamoyl, pyrimidinylcarbamoyl, pyrazinylcarbamoyl, furylcarbamoyl, thienylcarbamoyl, isoxazolylcarbamoyl, thiazolidinylcarbamoyl, oxazolidinylcarbamoyl, imidazolidinylcarbamoyl, pyrrolidinylcarbamoyl, piperidylcarbamoyl, tetrahydrofurylcarbamoyl and tetrahydropyranylcarbamoyl.

As preferred groups for $R^{4b}$ there may be specifically mentioned, for example, saturated or unsaturated alkoxy groups such as methoxy, 2-propynyloxy, 2-butynyloxy, 3-hexenyloxy, 5-hexenyloxy and 2,2-dimethylpropoxy; halogen-substituted alkoxy groups such as 2-bromoethoxy and 2-chloroethoxy; cycloalkyl-alkoxy groups such as cyclopentylmethoxy and cyclohexylmethoxy; aryl-alkoxy groups such as benzyloxy, aminobenzyloxy, chlorobenzyloxy, fluorobenzyloxy, bromobenzyloxy, nitrobenzyloxy, (trifluoromethyl)benzyloxy, dichlorobenzyloxy, dimethylbenzyloxy, methoxybenzyloxy, sulfamoylbenzyloxy, (methylenedioxy)benzyloxy, carboxybenzyloxy, (methoxycarbonyl)benzyloxy, n-butoxybenzyloxy, 3-phenylpropoxy, di(methoxyphenyl)methoxy, 2,2-diphenylethoxy, 1-methyl-1-phenylethoxy and naphthylmethoxy; heterocycle-substituted alkoxy groups such as thienylmethoxy, 2-(morpholinesulfonyl)thienylmethoxy, pyridylmethoxy, (5-hydroxypyridyl)methoxy, (2-methoxypyridyl)methoxy, 2-(pyridyl)ethoxy, pyrazinylmethoxy, pyrimidinylmethoxy, N-tosylimidazolylmethoxy, oxazolylmethoxy, 2-phenyloxazolylmethoxy, thiazolylmethoxy, 2-(morpholinesulfonyl)thiazolylmethoxy, (3,5-dioxo-2,4-thiazolidinyl)methoxy, N-methylpiperidylmethoxy, N-t-butoxycarbonylpiperidylmethoxy, N-acetylpiperidylmethoxy, N-methanesulfonylpiperidylmethoxy, (4-oxachroman-2-yl)methoxy, (3,3-dimethyl-2,4-dioxolanyl)methoxy, (1-methyl-3-oxetanyl)methoxy and 2-(morpholin-4-yl)ethoxy; alkoxy-alkoxy groups such as methoxymethyl and 2-ethoxyethoxy; benzyloxy-alkoxy groups such as 2-(benzyloxy)ethoxy; acyloxy-alkoxy groups such as 2-(acetyloxy)ethoxy; alkylamino-alkoxy groups such as bis(dimethylaminomethyl)methoxy; alkoxycarbonylamino-alkoxy groups such as 4-(t-butoxycarbonylamino)butoxy; and alkoxycarbonyl-alkoxy groups such as ethoxycarbonylmethoxy, 2-(methoxycarbonyl)ethoxy and 5-(ethoxycarbonyl)pentyloxy.

As particularly preferred groups for $R^{4b}$ there may be specifically mentioned, for example, methoxy, 2-propynyloxy, benzyloxy, aminobenzyloxy, chlorobenzyloxy, fluorobenzyloxy, (trifluoromethyl)benzyloxy, dichlorobenzyloxy, dimethylbenzyloxy, methoxybenzyloxy, sulfamoylbenzyloxy, (methylenedioxy)benzyloxy, carboxybenzyloxy, (methoxycarbonyl)benzyloxy, n-butoxybenzyloxy, thienylmethoxy, 2-(morpholinesulfonyl)thienylmethoxy, pyridylmethoxy, (2-methoxypyridyl)methoxy, (5-hydroxypyridyl)methoxy, 2-(pyridyl)ethoxy, pyrazinylmethoxy, pyrimidinylmethoxy, N-tosylimidazolylmethoxy, oxazolylmethoxy, 2-phenyloxazolylmethoxy, thiazolylmethoxy, 2-(morpholinesulfonyl)thiazolylmethoxy, (3,5-dioxo-2,4-thiazolidinyl)methoxy, N-methylpiperidylmethoxy and methoxymethyl.

When $R^4$ is $R^{4c}$, there may be mentioned as specific examples of substituents on the alkoxy groups of 1 to 4 carbons for $R^{4c}$, for example, halogen atoms such as fluorine, chlorine, bromine, iodine; cycloalkyl groups of 3 to 7 carbons such as cyclopropyl, cyclobutyl, cyclopentyl, cyclohexyl and cycloheptyl; aryl groups of 6 to 10 carbons such as phenyl and naphthyl; heterocycles such as imidazolyl, thiazolyl, isothiazolyl, pyrazolyl, triazolyl, tetrazolyl, pyrrolyl, pyridyl, pyrimidinyl, pyrazinyl, pyridazinyl, triazinyl, furyl, thienyl, oxazolyl, isoxazolyl, thiazolidinyl, oxazolidinyl, 3,5-dioxooxazolidinyl, imidazolidinyl, 2-oxoimidazolidinyl, pyrrolidinyl, piperidyl, morpholinyl, pyrazolidinyl, 3,5-dioxopyrazolidinyl, piperazinyl, 2,5-dioxopiperazinyl, tetrahydrofuryl, tetrahydropyranyl and dioxolanyl; —SH; —OH; alkoxy groups of 1 to 4 carbons such as methoxy, ethoxy, n-propoxy, isopropoxy, n-butoxy, isobutoxy, sec-butoxy, t-butoxy, n-pentyloxy, isopentyloxy, 3-pentyloxy, 2,2-dimethylpropoxy, n-hexyloxy, 4-methylpentyloxy and 2-ethylbutoxy; aryloxy groups of 6 to 10 carbons such as phenoxy and naphthyloxy; benzyloxy; groups represented by —O-Het (wherein Het represents a heterocycle), such as pyridyloxy and piperidyloxy; acyloxy groups of 1 to 5 carbons such as formyloxy, acetyloxy, propionyloxy, butyryloxy, isobutyryloxy and trimethylacetyloxy; arylcarboxy groups of 7 to 11 carbons such as benzoyloxy and naphthylcarboxy; phenylacetyloxy; groups represented by —O—CO-Het (wherein Het represents a heterocycle), such as imidazolylcarboxy, thiazolylcarboxy, isothiazolylcarboxy, pyrazolylcarboxy, triazolylcarboxy, pyrrolylcarboxy, pyridylcarboxy, pyrimidinylcarboxy, pyrazinylcarboxy, furylcarboxy, thienylcarboxy, isoxazolylcarboxy, thiazolidinylcarboxy, oxazolidinylcarboxy, imidazolidinylcarboxy, pyrrolidinylcarboxy, piperidylcarboxy, morpholinylcarboxy, piperazinylcarboxy, tetrahydrofurylcarboxy and tetrahydropyranylcarboxy; amino; monosubstituted or disubstituted amino groups such as methylamino, dimethylamino, ethylamino, 2-hydroxy-2-phenethylamino, 2-hydroxy-3-phenoxypropylamino, diethylamino, propylamino, dipropylamino, isopropylamino, diisopropylamino, dibutylamino, benzylamino, dibenzylamino, imidazolylamino, thiazolylamino, isothiazolylamino, pyrazolylamino, triazolylamino, pyrrolylamino, pyridylamino, dipyridylamino, pyrimidinylamino, pyrazinylamino, furylamino, thienylamino, isoxazolylamino, thiazolidinylamino, oxazolidinylamino, imidazolidinylamino, pyrrolidinylamino, piperidylamino, tetrahydrofurylamino and tetrahydropyranylamino; optionally halogen-substituted alkylsulfonylamino groups of 1 to 4 carbons such as methanesulfonylamino, ethanesulfonylamino, n-propanesulfonylamino and trifluoromethanesulfonylamino; phenylsulfonylamino; acylamino groups of 1 to 5 carbons such as formylamino, acetylamino, propionylamino, butyrylamino, isobutyrylamino and trimethylacetylamino; arylcarbonylamino groups of 7 to 11 carbons such as benzoylamino, 4-chlorobenzoylamino and naphthylcarbonylamino; phenylacetylamino; groups represented by —NH—CO-Het (wherein Het represents a heterocycle), such as imidazolylcarbonylamino, thiazolylcarbonylamino, pyridylcarbonylamino, pyrimidinylcarbonylamino, pyrazinylcarbonylamino, furylcarbonylamino, thienylcarbonylamino, thiazolidinylcarbonylamino, oxazolidinylcarbonylamino, imidazolidinylcarbonylamino, pyrrolidinylcarbonylamino and piperidylcarbonylamino; alkoxycarbonylamino groups of 2 to 5 carbons such as methoxycarbonylamino, ethoxycarbonylamino, n-propoxycarbonylamino, isopropoxycarbonylamino and t-butoxycarbonylamino; benzyloxycarbonylamino; formyl; carboxyl; alkoxycarbonyl groups of 2 to 5 carbons such as methoxycarbonyl, ethoxycarbonyl, n-propoxycarbonyl, isopropoxycarbonyl and t-butoxycarbonyl; phenoxycarbonyl; benzyloxycarbonyl; acyl groups of 2 to 5 carbons such as acetyl, propionyl, butyryl and isobutyryl; groups represented by —CO-Het (wherein Het represents a heterocycle), such as imidazolylcarbonyl, thiazolylcarbonyl, isothiazolylcarbonyl, pyrazolylcarbonyl, triazolylcarbonyl, pyrrolylcarbonyl, pyridylcarbonyl, pyrimidinylcarbonyl, pyrazinylcarbonyl, furylcarbonyl, thienylcarbonyl, isoxazolylcarbonyl, thiazolidinylcarbonyl, oxazolidinylcarbonyl, imidazolidinylcarbonyl, pyrrolidinylcarbonyl, piperidylcarbonyl, morpholinylcarbonyl and piperazinylcarbonyl; groups represented by —CO—O-Het (wherein Het represents a heterocycle), such as pyridyloxycarbonyl and piperidyloxycarbonyl; and carbamoyl groups such as carbamoyl, methylcarbamoyl, dimethylcarbamoyl, ethylcarbamoyl, diethylcarbamoyl, propylcarbamoyl, dipropylcarbamoyl, benzylcarbamoyl, dibenzylcarbamoyl, imidazolylcarbamoyl, thiazolylcarbamoyl, isothiazolylcarbamoyl, pyrazolylcarbamoyl, triazolylcarbamoyl, pyrrolylcarbamoyl, pyridylcarbamoyl, pyrimidinylcarbamoyl, pyrazinylcarbamoyl, furylcarbamoyl, thienylcarbamoyl, isoxazolylcarbamoyl, thiazolidinylcarbamoyl, oxazolidinylcarbamoyl, imidazolidinylcarbamoyl, pyrrolidinylcarbamoyl, piperidylcarbamoyl, tetrahydrofurylcarbamoyl and tetrahydropyranylcarbamoyl.

As preferred groups for $R^{4c}$ there may be specifically mentioned, for example, phenethyl, α-hydroxybenzyl, 1-(acetyloxy)ethyl and (3,5-dioxo-2,4-thiazolidinyl)methyl.

Thus, as specific preferred combinations for $R^1$, $R^2$, $R^3$, and $R^4$ there may be mentioned those in which, for example, $R^1$ is methyl, ethyl, or isopropyl, $R^2$ is an acetyl or propionyl group substituted with a substituent selected from the group consisting of phenyl, phenoxy, amino, t-butoxycarbonylamino, benzyloxycarbonylamino, (benzyloxycarbonyl)-N-methylamino, acetylamino, and morpholinylcarbonyl; or hydrogen, acetyl, propionyl, isobutyryl, benzoyl, pyridylcarbonyl, pyrrolidinylcarbonyl, furylcarbonyl, methanesulfonyl, or trifluoromethanesulfonyl, $R^3$ is methyl, ethyl, isopropyl, n-pentyl, cyclopentylmethyl or benzyl, and $R^4$ is hydrogen, nitro, cyano, bromine, thienyl, piperazinyl, trifluoromethanesulfonyloxy, phenylsulfonyloxy, acetyloxy, dimethylamino, dibenzylamino, N-methyl-N-methanesulfonylamino, N-methyl-N-phenylsulfonylamino, N-methyl-N-acetylamino, N-methyl-N-isobutyrylamino, N-methyl-N-benzoylamino, N-methyl-N-phenylacetylamino, N-methyl-N-imidazolylcarbonylamino, N-methyl-N-thiazolylcarbonylamino, N-methyl-N-pyridylcarbonylamino, N-methyl-N-pyrimidinylcarbonylamino, N-methyl-N-pyrazinylcarbonylamino, N-methyl-N-thienylcarbonylamino, N-methyl-N-oxazolylcarbonylamino, N-methyl-N-(t-butoxycarbonyl)amino, thiazolylcarbamoyl, methoxycarbonyl, isopropoxycarbonyl, (3,5-dioxo-2,4-thiazolidinylidene)methyl, methoxy, 2-propynyloxy, benzyloxy, aminobenzyloxy, chlorobenzyloxy, fluorobenzyloxy, (trifluoromethyl)benzyloxy, dichlorobenzyloxy, dimethylbenzyloxy, methoxybenzyloxy, sulfamoylbenzyloxy, (methylenedioxy)benzyloxy, carboxybenzyloxy, (methoxycarbonyl)benzyloxy, n-butoxybenzyloxy, thienylmethoxy, 2-(morpholinesulfonyl)thienylmethoxy, pyridylmethoxy, (2-methoxypyridyl)methoxy, 2-(pyridyl)ethoxy, pyrazinylmethoxy, pyrimidinylmethoxy, N-tosylimidazolylmethoxy, oxazolylmethoxy, 2-phenyloxazolylmethoxy, thiazolylmethoxy, 2-(morpholinesulfonyl)thiazolylmethoxy, (3,5-dioxo-2,4-thiazolidinyl)methoxy, N-methylpiperidylmethoxy, methoxymethyl, phenethyl, α-hydroxybenzyl, 1-(acetyloxy)ethyl or (3,5-dioxo-2,4-thiazolidinyl)methyl.

As specific compounds represented by structural formula (I) above there may be mentioned those compounds mentioned in the examples of the present specification, but additional compounds that may be mentioned included the following:

6-(benzofuran-2-yl)-3-ethyl-4-hydroxy-5-methyl-2H-pyran-2-one;

6-(benzofuran-2-yl)-4-hydroxy-5-methyl-3-n-propyl-2H-pyran-2-one;

4-acetyloxy-6-(benzofuran-2-yl)-5-ethyl-3-methyl-2H-pyran-2-one;

4-acetyloxy-6-(benzofuran-2-yl)-5-isopropyl-3-methyl-2H-pyran-2-one;

6-(benzofuran-2-yl)-4-(2-(t-butoxycarbonylamino)acetyloxy)-5-ethyl-3-methyl-2H-pyran-2-one;

6-(benzofuran-2-yl)-5-ethyl-3-methyl-4-(2-pyrrolidon-5-ylcarboxy)-2H-pyran-2-one;

4-(2-aminoacetyloxy)-6-(benzofuran-2-yl)-5-ethyl-3-methyl-2H-pyran-2-one;

4-(3-acetylamino-4-morpholinyl-4-oxobutyryloxy)-6-(benzofuran-2-yl)-5-ethyl-3-methyl-2H-pyran-2-one;

6-(benzofuran-2-yl)-3,5-dimethyl-4-propionyloxy-2H-pyran-2-one;

6-(benzofuran-2-yl)-5-ethyl-4-isobutyryloxy-3-methyl-2H-pyran-2-one;

6-(benzofuran-2-yl)-3,5-dimethyl-4-isovaleryloxy-2H-pyran-2-one;

6-(benzofuran-2-yl)-3,5-dimethyl-4-(2,2,2-trimethylacetyloxy)-2H-pyran-2-one;

6-(benzofuran-2-yl)-4-cyclohexylcarboxy-3,5-dimethyl-2H-pyran-2-one;

6-(benzofuran-2-yl)-4-(2-cyclopropylacetyloxy)-3,5-dimethyl-2H-pyran-2-one;

6-(benzofuran-2-yl)-4-(2-cyclopentylacetyloxy)-3,5-dimethyl-2H-pyran-2-one;

6-(benzofuran-2-yl)-4-benzoyloxy-5-ethyl-3-methyl-2H-pyran-2-one;

6-(benzofuran-2-yl)-4-benzoyloxy-5-isopropyl-3-methyl-2H-pyran-2-one;

6-(benzofuran-2-yl)-3,5-dimethyl-4-naphthylcarboxy-2H-pyran-2-one;

6-(benzofuran-2-yl)-3,5-dimethyl-4-imidazolylcarboxy-2H-pyran-2-one;

6-(benzofuran-2-yl)-3,5-dimethyl-4-thiazolylcarboxy-2H-pyran-2-one;

6-(benzofuran-2-yl)-3,5-dimethyl-4-triazolylcarboxy-2H-pyran-2-one;

6-(benzofuran-2-yl)-5-ethyl-3-methyl-4-pyridylcarboxy-2H-pyran-2-one;

6-(benzofuran-2-yl)-3,5-dimethyl-4-pyrimidinylcarboxy-2H-pyran-2-one;

6-(benzofuran-2-yl)-3,5-dimethyl-4-pyrazinylcarboxy-2H-pyran-2-one;

6-(benzofuran-2-yl)-3,5-dimethyl-4-thienylcarboxy-2H-pyran-2-one;

6-(benzofuran-2-yl)-3,5-dimethyl-4-isoxazolylcarboxy-2H-pyran-2-one;

6-(benzofuran-2-yl)-3,5-dimethyl-4-(2-imidazolylacetyloxy)-2H-pyran-2-one;

6-(benzofuran-2-yl)-3,5-dimethyl-4-(2-pyridylacetyloxy)-2H-pyran-2-one;

6-(benzofuran-2-yl)-3,5-dimethyl-4-(2-methoxyacetyloxy)-2H-pyran-2-one;

6-(benzofuran-2-yl)-3,5-dimethyl-4-(2-t-butoxyacetyloxy)-2H-pyran-2-one;

6-(benzofuran-2-yl)-4-hydroxy-3-methyl-5-n-propyl-2H-pyran-2-one;

6-(benzofuran-2-yl)-5-cyclopentyl-4-hydroxy-3-methyl-2H-pyran-2-one;
6-(benzofuran-2-yl)-5-cyclopropylmethyl-4-hydroxy-3-methyl-2H-pyran-2-one;
6-(benzofuran-2-yl)-5-cyclohexylmethyl-4-hydroxy-3-methyl-2H-pyran-2-one;
6-(benzofuran-2-yl)-4-hydroxy-3-methyl-5-naphthylmethyl-2H-pyran-2-one;
6-(benzofuran-2-yl)-5-ethoxy-4-hydroxy-3-methyl-2H-pyran-2-one;
6-(benzofuran-2-yl)-4-hydroxy-5-isopropoxy-3-methyl-2H-pyran-2-one;
4-acetyloxy-3,5-dimethyl-6-(5-(2-thienyl)benzofuran-2-yl)-2H-pyran-2-one;
3,5-dimethyl-6-(5-((3,5-dioxo-2,4-oxazolidinylidene)methyl)benzofuran-2-yl)-4-hydroxy-2H-pyran-2-one;
3,5-dimethyl-6-(5-((2,5-dioxoimidazolidin-4-ylidene)methyl)benzofuran-2-yl)-4-hydroxy-2H-pyran-2-one;
3,5-dimethyl-4-hydroxy-6-(5-((5-oxo-3-thioxo-2,4-thiazolidinylidene)methyl)benzofuran-2-yl)-2H-pyran-2-one;
3,5-dimethyl-4-hydroxy-6-(5-((2,4,6-trioxo-3,5-diazaperhydroinylidene)methyl)benzofuran-2-yl)-2H-pyran-2-one;
3,5-dimethyl-6-(5-((3,5-dimethyl-2,4,6-trioxo-3,5-diazaperhydroinylidene)methyl)benzofuran-2-yl)-4-hydroxy-2H-pyran-2-one;
3,5-dimethyl-6-(5-(2-(3,5-dioxo-2,4-thiazolidinylidene)ethoxy)benzofuran-2-yl)-4-hydroxy-2H-pyran-2-one;
3,5-dimethyl-6-(5-(2-(3,5-dioxo-2,4-oxazolidinylidene)ethoxy)benzofuran-2-yl)-4-hydroxy-2H-pyran-2-one;
3,5-dimethyl-6-(5-(2-(2,5-dioxoimidazolidin-4-ylidene)ethoxy)benzofuran-2-yl)-4-hydroxy-2H-pyran-2-one;
3,5-dimethyl-4-hydroxy-6-(5-(2-(5-oxo-3-thioxo-2,4-thiazolidinylidene)ethoxy)benzofuran-2-yl)-2H-pyran-2-one;
3,5-dimethyl-4-hydroxy-6-(5-(2-(2,4,6-trioxo-3,5-diazaperhydroinylidene)ethoxy)benzofuran-2-yl)-2H-pyran-2-one;
3,5-dimethyl-6-(5-(2-(3,5-dimethyl-2,4,6-trioxo-3,5-diazaperhydroinylidene)ethoxy)benzofuran-2-yl)-4-hydroxy-2H-pyran-2-one;
3,5-dimethyl-6-(5-((3,5-dioxo-2,4-thiazolidinyl)sulfonylmethyl)benzofuran-2-yl)-4-hydroxy-2H-pyran-2-one;
3,5-dimethyl-6-(5-((3,5-dioxo-2,4-oxazolidinyl)sulfonylmethyl)benzofuran-2-yl)-4-hydroxy-2H-pyran-2-one;
3,5-dimethyl-6-(5-((2,5-dioxoimidazolidin-4-yl)sulfonylmethyl)benzofuran-2-yl)-4-hydroxy-2H-pyran-2-one;
3,5-dimethyl-4-hydroxy-6-(5-((5-oxo-3-thioxo-2,4-thiazolidinyl)sulfonylmethyl)benzofuran-2-yl)-2H-pyran-2-one;
3,5-dimethyl-6-(5-((3,5-dioxo-2,4-thiazolidinyl)methoxy)benzofuran-2-yl)-4-hydroxy-2H-pyran-2-one;
3,5-dimethyl-6-(5-((3,5-dioxo-2,4-oxazolidinyl)methoxy)benzofuran-2-yl)-4-hydroxy-2H-pyran-2-one;
3,5-dimethyl-6-(5-((2,5-dioxoimidazolidin-4-yl)methoxy)benzofuran-2-yl)-4-hydroxy-2H-pyran-2-one;
3,5-dimethyl-4-hydroxy-6-(5-((5-oxo-3-thioxo-2,4-thiazolidinyl)methoxy)benzofuran-2-yl)-2H-pyran-2-one;
3,5-dimethyl-6-(5-((2,4,6-trioxo-3,5-diazaperhydroinyl)methoxy)benzofuran-2-yl)-4-hydroxy-2H-pyran-2-one;
3,5-dimethyl-6-(5-((3,5-dimethyl-2,4,6-trioxo-3,5-diazaperhydroinyl)methoxy)benzofuran-2-yl)-4-hydroxy-2H-pyran-2-one;
3,5-dimethyl-4-hydroxy-6-(5-(N-methyl-N-phenylcarbamoyl)benzofuran-2-yl)-2H-pyran-2-one;
6-(5-(N-benzyl-N-methylcarbamoyl)benzofuran-2-yl)-3,5-dimethyl-4-hydroxy-2H-pyran-2-one;
3,5-dimethyl-4-hydroxy-6-(5-(N-methyl-N-pyridylcarbamoyl)benzofuran-2-yl)-2H-pyran-2-one;
3,5-dimethyl-4-hydroxy-6-(5-(N-methyl-N-thiazolylcarbamoyl)benzofuran-2-yl)-2H-pyran-2-one;
3,5-dimethyl-4-hydroxy-6-(5-(N-methyl-N-(pyridylmethyl)carbamoyl)benzofuran-2-yl)-2H-pyran-2-one;
3,5-dimethyl-4-hydroxy-6-(5-(2-(2-hydroxy-2-phenethylamino)ethoxy)benzofuran-2-yl)-2H-pyran-2-one;
3,5-dimethyl-4-hydroxy-6-(5-(2-(2-hydroxy-3-phenoxypropylamino)ethoxy)benzofuran-2-yl)-2H-pyran-2-one;
3,5-dimethyl-4-hydroxy-6-(5-(2-hydroxy-3-aminopropoxy)benzofuran-2-yl)-2H-pyran-2-one;
3,5-dimethyl-4-hydroxy-6-(5-(2-hydroxy-3-phenylaminopropoxy)benzofuran-2-yl)-2H-pyran-2-one;
3,5-dimethyl-4-hydroxy-6-(5-(3-(2-hydroxy-2-phenethylamino)propyl)benzofuran-2-yl)-2H-pyran-2-one;
3,5-dimethyl-4-hydroxy-6-(5-(3-(2-hydroxy-3-phenoxypropylamino)propyl)benzofuran-2-yl)-2H-pyran-2-one;
3,5-dimethyl-4-hydroxy-6-(5-(2-(2-hydroxy-2-phenethylamino)ethyl)benzofuran-2-yl)-2H-pyran-2-one;
3,5-dimethyl-4-hydroxy-6-(5-(2-(2-hydroxy-3-phenoxypropylamino)ethyl)benzofuran-2-yl)-2H-pyran-2-one;
3,5-dimethyl-6-(5-(3,5-dioxopyrazolidin-4-ylmethyl)benzofuran-2-yl)-4-hydroxy-2H-pyran-2-one;
3,5-dimethyl-6-(5-(3,5-dioxooxazolidin-4-ylmethyl)benzofuran-2-yl)-4-hydroxy-2H-pyran-2-one;
3,5-dimethyl-4-hydroxy-6-(5-(2-oxoimidazolidinylmethyl)benzofuran-2-yl)-2H-pyran-2-one;
3,5-dimethyl-6-(5-(2,5-dioxopiperazinylmethyl)benzofuran-2-yl)-4-hydroxy-2H-pyran-2-one;
3,5-dimethyl-4-hydroxy-6-(5-(imidazolylmethyl)benzofuran-2-yl)-2H-pyran-2-one;
6-(5-(N-benzothiazolyl-N-methylcarbamoyl)benzofuran-2-yl)-3,5-dimethyl-4-hydroxy-2H-pyran-2-one;
3,5-dimethyl-4-hydroxy-6-(5-(6-oxo-4,5-benzoxazin-2-yl)benzofuran-2-yl)-2H-pyran-2-one;
3,5-dimethyl-4-hydroxy-6-(5-(3-pyridylaminomethyl)benzofuran-2-yl)-2H-pyran-2-one;
6-(5-(4-bromo-2-cyanophenylcarbamoyl)benzofuran-2-yl)-3,5-dimethyl-4-hydroxy-2H-pyran-2-one;
3,5-dimethyl-4-hydroxy-6-(5-(N-methyl-N-(3-pyridyl)aminomethyl)benzofuran-2-yl)-2H-pyran-2-one;
3,5-dimethyl-4-hydroxy-6-(5-(N-methyl-N-(3-pyridyl)carbamoyl)benzofuran-2-yl)-2H-pyran-2-one;
3,5-dimethyl-4-hydroxy-6-(5-(4-(2-pyridyl)piperazinylcarbonyl)benzofuran-2-yl)-2H-pyran-2-one;
3,5-dimethyl-4-hydroxy-6-(5-(4-(2-pyrimidinyl)piperazinylcarbonyl)benzofuran-2-yl)-2H-pyran-2-one;
3,5-dimethyl-4-hydroxy-6-(5-(N-methyl-N-(2-pyridyl)carbamoyl)benzofuran-2-yl)-2H-pyran-2-one;
3,5-dimethyl-4-hydroxy-6-(5-(N-(2-pyrimidinyl)carbamoyl)benzofuran-2-yl)-2H-pyran-2-one;
3,5-dimethyl-4-hydroxy-6-(5-((2-pyridylmethyl)carbamoyl)benzofuran-2-yl)-2H-pyran-2-one;
3,5-dimethyl-4-hydroxy-6-(5-(triazolylcarbamoyl)benzofuran-2-yl)-2H-pyran-2-one;
3,5-dimethyl-6-(5-(2,5-dioxopyrrolidinyl)benzofuran-2-yl)-4-hydroxy-2H-pyran-2-one;

3,5-dimethyl-6-(5-(2,6-dioxopiperidinyl)benzofuran-2-yl)-4-hydroxy-2H-pyran-2-one;

3,5-dimethyl-6-(5-(2,3-dioxopiperazinyl)benzofuran-2-yl)-4-hydroxy-2H-pyran-2-one;

6-(5-(2-(4-chlorobenzoylamino)ethyl)benzofuran-2-yl)-3,5-dimethyl-4-hydroxy-2H-pyran-2-one;

6-(5-(3-(acetylamino)propoxy)benzofuran-2-yl)-3,5-dimethyl-4-hydroxy-2H-pyran-2-one;

3,5-dimethyl-4-hydroxy-6-(5-(3-(2-pyrazinylcarbonylamino)propoxy)benzofuran-2-yl)-2H-pyran-2-one;

3,5-dimethyl-4-hydroxy-6-(5-(3-(2-pyridylcarbonylamino)propoxy)benzofuran-2-yl)-2H-pyran-2-one;

3,5-dimethyl-4-hydroxy-6-(5-(3-(5-isoxazolylcarbonylamino)propoxy)benzofuran-2-yl)-2H-pyran-2-one;

3,5-dimethyl-4-hydroxy-6-(5-(3-(morpholinylcarbonylamino)propoxy)benzofuran-2-yl)-2H-pyran-2-one;

3,5-dimethyl-4-hydroxy-6-(5-(3-(methanesulfonylamino)propoxy)benzofuran-2-yl)-2H-pyran-2-one;

3,5-dimethyl-6-(5-(3-(dimethylaminosulfonylamino)propoxy)benzofuran-2-yl)-4-hydroxy-2H-pyran-2-one;

3,5-dimethyl-4-hydroxy-6-(5-(3-(isoxazolylsulfonylamino)propoxy)benzofuran-2-yl)-2H-pyran-2-one;

6-(5-(N-acetylpiperidin-3-ylmethoxy)benzofuran-2-yl)-3,5-dimethyl-4-hydroxy-2H-pyran-2-one;

3,5-dimethyl-4-hydroxy-6-(5-(N-(2-pyridylcarbonyl)piperidin-3-ylmethoxy)benzofuran-2-yl)-2H-pyran-2-one;

3,5-dimethyl-4-hydroxy-6-(5-(N-(2-pyrazinylcarbonyl)piperidin-3-ylmethoxy)benzofuran-2-yl)-2H-pyran-2-one;

3,5-dimethyl-4-hydroxy-6-(5-(N-(5-isoxazolylcarbonyl)piperidin-3-ylmethoxy)benzofuran-2-yl)-2H-pyran-2-one;

3,5-dimethyl-4-hydroxy-6-(5-(N-(morpholinylcarbonyl)piperidin-3-ylmethoxy)benzofuran-2-yl)-2H-pyran-2-one;

3,5-dimethyl-4-hydroxy-6-(5-(N-methanesulfonylpiperidin-3-ylmethoxy)benzofuran-2-yl)-2H-pyran-2-one;

3,5-dimethyl-6-(5-(N-(dimethylaminosulfonyl)piperidin-3-ylmethoxy)benzofuran-2-yl)-4-hydroxy-2H-pyran-2-one;

3,5-dimethyl-4-hydroxy-6-(5-(N-(5-thiazolylsulfonyl)piperidin-3-ylmethoxy)benzofuran-2-yl)-2H-pyran-2-one; and 3,5-dimethyl-4-hydroxy-6-(5-(N-(5-isoxazolylsulfonyl)piperidin-3-ylmethoxy)benzofuran-2-yl)-2H-pyran-2-one.

As preferred specific compounds represented by structural formula (I) above there may be mentioned, for example, the following:

4-acetyloxy-6-(benzofuran-2-yl)-3,5-dimethyl-2H-pyran-2-one;

6-(benzofuran-2-yl)-3,5-dimethyl-4-hydroxy-2H-pyran-2-one;

6-(benzofuran-2-yl)-4-benzoyloxy-3,5-dimethyl-2H-pyran-2-one;

6-(benzofuran-2-yl)-3,5-dimethyl-4-methanesulfonyloxy-2H-pyran-2-one;

6-(benzofuran-2-yl)-3,5-dimethyl-4-(2-pyridylcarboxy)-2H-pyran-2-one;

3,5-dimethyl-6-(5-((3,5-dioxo-2,4-thiazolidinylidene)methyl)benzofuran-2-yl)-4-hydroxy-2H-pyran-2-one;

3,5-dimethyl-6-(5-((3,5-dioxo-2,4-thiazolidinyl)methyl)benzofuran-2-yl)-4-hydroxy-2H-pyran-2-one;

6-(benzofuran-2-yl)-4-hydroxy-3-methyl-5-n-pentyl-2H-pyran-2-one;

3,5-dimethyl-4-hydroxy-6-(5-methoxybenzofuran-2-yl)-2H-pyran-2-one;

3,5-dimethyl-4-hydroxy-6-(7-methoxybenzofuran-2-yl)-2H-pyran-2-one;

4-acetyloxy-3,5-dimethyl-6-(6-(trifluoromethanesulfonyloxy)benzofuran-2-yl)-2H-pyran-2-one;

4-acetyloxy-3,5-dimethyl-6-(6-(2-thienyl)benzofuran-2-yl)-2H-pyran-2-one;

3,5-dimethyl-4-hydroxy-6-(6-methoxybenzofuran-2-yl)-2H-pyran-2-one;

3,5-dimethyl-4-hydroxy-6-(5-(5-pyrimidinylmethoxy)benzofuran-2-yl)-2H-pyran-2-one;

6-(benzofuran-2-yl)-3,5-dimethyl-4-(4-hydroxymethylbenzoyloxy)-2H-pyran-2-one;

6-(benzofuran-2-yl)-4-(2-(N-carbobenzyloxy-N-methylamino)acetyloxy)-3,5-dimethyl-2H-pyran-2-one;

6-(benzofuran-2-yl)-3,5-dimethyl-4-(4-methoxybenzoyloxy)-2H-pyran-2-one;

6-(benzofuran-2-yl)-3,5-dimethyl-4-(2-phenylacetyloxy)-2H-pyran-2-one;

6-(benzofuran-2-yl)-5-ethyl-4-hydroxy-3-methyl-2H-pyran-2-one;

6-(benzofuran-2-yl)-4-hydroxy-5-isopropyl-3-methyl-2H-pyran-2-one;

6-(benzofuran-2-yl)-5-benzyl-4-hydroxy-3-methyl-2H-pyran-2-one;

6-(benzofuran-2-yl)-3,5-dimethyl-4-isobutyryloxy-2H-pyran-2-one;

4-acetyloxy-3,5-dimethyl-6-(5-nitrobenzofuran-2-yl)-2H-pyran-2-one;

6-(benzofuran-2-yl)-3,5-dimethyl-4-(2-phenoxyacetyloxy)-2H-pyran-2-one;

3,5-dimethyl-4-hydroxy-6-(5-nitrobenzofuran-2-yl)-2H-pyran-2-one;

3,5-dimethyl-6-(5-(dimethylamino)benzofuran-2-yl)-4-hydroxy-2H-pyran-2-one;

6-(5-(dibenzylamino)benzofuran-2-yl)-3,5-dimethyl-4-hydroxy-2H-pyran-2-one;

3,5-dimethyl-4-hydroxy-6-(5-(N-methyl-N-(2-thienylcarbonyl)amino)benzofuran-2-yl)-2H-pyran-2-one;

3,5-dimethyl-4-hydroxy-6-(5-(N-methyl-N-(3-pyridylcarbonyl)amino)benzofuran-2-yl)-2H-pyran-2-one;

3,5-dimethyl-4-hydroxy-6-(5-(N-isobutyryl-N-methylamino)benzofuran-2-yl)-2H-pyran-2-one;

3,5-dimethyl-4-hydroxy-6-(5-(N-methyl-N-(phenylacetyl)amino)benzofuran-2-yl)-2H-pyran-2-one;

6-(5-(N-benzoyl-N-methylamino)benzofuran-2-yl)-3,5-dimethyl-4-hydroxy-2H-pyran-2-one;

6-(5-(N-t-butoxycarbonyl-N-methylamino)benzofuran-2-yl)-3,5-dimethyl-4-hydroxy-2H-pyran-2-one;

6-(5-(benzothiazolylcarbamoyl)benzofuran-2-yl)-3,5-dimethyl-4-hydroxy-2H-pyran-2-one;

6-(5-(benzimidazolylcarbamoyl)benzofuran-2-yl)-3,5-dimethyl-4-hydroxy-2H-pyran-2-one;

3,5-dimethyl-4-hydroxy-6-(5-(N-methyl-N-phenylcarbamoyl)benzofuran-2-yl)-2H-pyran-2-one;

6-(5-(N-(4-chlorophenylsulfonyl)-N-methylamino)benzofuran-2-yl)-3,5-dimethyl-4-hydroxy-2H-pyran-2-one;

3,5-dimethyl-4-hydroxy-6-(5-(1,3,4-trihydroisoquinolin-2-ylcarbonyl)benzofuran-2-yl)-2H-pyran-2-one;

3,5-dimethyl-4-hydroxy-6-(5-morpholinylbenzofuran-2-yl)-2H-pyran-2-one;

6-(benzofuran-2-yl)-3,5-dimethyl-4-isonicotinoyloxy-2H-pyran-2-one;

4-(2-aminoacetyloxy)-6-(benzofuran-2-yl)-3,5-dimethyl-2H-pyran-2-one;
6-(5-benzyloxybenzofuran-2-yl)-4-(2-(t-butoxycarbonylamino)acetyloxy)-3,5-dimethyl-2H-pyran-2-one;
4-(2-aminoacetyloxy)-6-(5-benzyloxybenzofuran-2-yl)-3,5-dimethyl-2H-pyran-2-one;
4-(4-(acetylamino)benzoyloxy)-6-(5-benzyloxybenzofuran-2-yl)-3,5-dimethyl-2H-pyran-2-one;
6-(5-benzyloxybenzofuran-2-yl)-3,5-dimethyl-4-nicotinoyloxy-2H-pyran-2-one;
6-(5-benzyloxybenzofuran-2-yl)-3,5-dimethyl-4-isonicotinoyloxy-2H-pyran-2-one;
6-(5-benzyloxybenzofuran-2-yl)-5-ethyl-4-hydroxy-3-methyl-2H-pyran-2-one;
5-ethyl-4-hydroxy-3-methyl-6-(5-(3-pyridylmethoxy)benzofuran-2-yl)-2H-pyran-2-one;
4-acetyloxy-3,5-dimethyl-6-(5-(2-thiazolylmethoxy)benzofuran-2-yl)-2H-pyran-2-one;
3,5-dimethyl-4-hydroxy-6-(5-(5-thiazolylmethoxy)benzofuran-2-yl)-2H-pyran-2-one;
4-acetyloxy-6-(5-(2,4-dichloro-5-thiazolylmethoxy)benzofuran-2-yl)-3,5-dimethyl-2H-pyran-2-one;
3,5-dimethyl-4-hydroxy-6-(5-(2-(4-methyl-5-thiazolyl)ethoxy)benzofuran-2-yl)-2H-pyran-2-one;
4-acetyloxy-3,5-dimethyl-6-(5-(2-(4-methyl-5-thiazolyl)ethoxy)benzofuran-2-yl)-2H-pyran-2-one;
3,5-dimethyl-4-hydroxy-6-(5-(4-methyl-5-thiazolylmethoxy)benzofuran-2-yl)-2H-pyran-2-one;
3,5-dimethyl-4-hydroxy-6-(5-(2-(morpholinesulfonyl)-5-thiazolylmethoxy)benzofuran-2-yl)-2H-pyran-2-one;
4-acetyloxy-3,5-dimethyl-6-(5-(4-methyl-1-tosyl-5-imidazolylmethoxy)benzofuran-2-yl)-2H-pyran-2-one;
6-(benzofuran-2-yl)-3,5-dimethyl-4-(3-phenylpropionyloxy)-2H-pyran-2-one;
6-(benzofuran-2-yl)-3,5-dimethyl-4-(2-furoyloxy)-2H-pyran-2-one;
6-(benzofuran-2-yl)-3,5-dimethyl-4-nicotinoyloxy-2H-pyran-2-one;
6-(benzofuran-2-yl)-3,5-dimethyl-4-(2-acetylamino-4-(morpholin-4-yl)-4-oxobutyryloxy)-2H-pyran-2-one;
4-acetyloxy-6-(5-bromobenzofuran-2-yl)-3,5-dimethyl-2H-pyran-2-one;
6-(benzofuran-2-yl)-5-cyclopentylmethyl-4-hydroxy-3-methyl-2H-pyran-2-one;
6-(benzofuran-2-yl)-4-(1-carbobenzyloxy-2-pyrrolidon-5-ylcarboxy)-3,5-dimethyl-2H-pyran-2-one;
6-(benzofuran-2-yl)-3,5-dimethyl-4-(2-pyrrolidon-5-ylcarboxy)-2H-pyran-2-one;
6-(benzofuran-2-yl)-4-(2-(t-butoxycarbonylamino)acetyloxy)-3,5-dimethyl-2H-pyran-2-one;
6-(benzofuran-2-yl)-4-(2,4-dimethoxybenzoyloxy)-3,5-dimethyl-2H-pyran-2-one;
6-(benzofuran-2-yl)-3,5-dimethyl-4-(3-dimethylaminobenzoyloxy)-2H-pyran-2-one;
4-(4-(acetylamino)benzoyloxy)-6-(benzofuran-2-yl)-3,5-dimethyl-2H-pyran-2-one;
3,5-dimethyl-6-(5-(2-fluorobenzyloxy)benzofuran-2-yl)-4-hydroxy-2H-pyran-2-one;
3,5-dimethyl-4-hydroxy-6-(5-(3,4-(methylenedioxy)benzyloxy)benzofuran-2-yl)-2H-pyran-2-one;
3,5-dimethyl-4-hydroxy-6-(5-(3-pyridylmethoxy)benzofuran-2-yl)-2H-pyran-2-one;
3,5-dimethyl-4-hydroxy-6-(5-(5-hydroxy-3-pyridylmethoxy)benzofuran-2-yl)-2H-pyran-2-one;
4-acetyloxy-3,5-dimethyl-6-(5-(2-methoxy-5-pyridylmethoxy)benzofuran-2-yl)-2H-pyran-2-one;
3,5-dimethyl-4-hydroxy-6-(5-(1-methylpiperidin-3-ylmethoxy)benzofuran-2-yl)-2H-pyran-2-one;
6-(5-(4-carboxybenzyloxy)benzofuran-2-yl)-3,5-dimethyl-4-hydroxy-2H-pyran-2-one;
3,5-dimethyl-4-hydroxy-6-(5-(2-(trifluoromethyl)benzyloxy)benzofuran-2-yl)-2H-pyran-2-one;
3,5-dimethyl-4-hydroxy-6-(5-(3-(trifluoromethyl)benzyloxy)benzofuran-2-yl)-2H-pyran-2-one;
6-(5-(3,4-dimethylbenzyloxy)benzofuran-2-yl)-3,5dimethyl-4-hydroxy-2H-pyran-2-one;
3,5-dimethyl-4-hydroxy-6-(5-(2-thienylmethoxy)benzofuran-2-yl)-2H-pyran-2-one;
4-acetyloxy-3,5-dimethyl-6-(5-(2-thienylmethoxy)benzofuran-2-yl)-2H-pyran-2-one;
3,5-dimethyl-4-hydroxy-6-(5-(3-thienylmethoxy)benzofuran-2-yl)-2H-pyran-2-one;
3,5-dimethyl-4-hydroxy-6-(5-(2-(morpholinesulfonyl)-5-thienylmethoxy)benzofuran-2-yl)-2H-pyran-2-one;
4-acetyloxy-3,5-dimethyl-6-(5-(2-(morpholinesulfonyl)-5-thienylmethoxy)benzofuran-2-yl)-2H-pyran-2-one;
3,5-dimethyl-4-hydroxy-6-(5-(4-oxazolylmethoxy)benzofuran-2-yl)-2H-pyran-2-one;
3,5-dimethyl-4-hydroxy-6-(5-(2-phenyl-4-oxazolylmethoxy)benzofuran-2-yl)-2H-pyran-2-one;
6-(5-(2,4-dichlorobenzyloxy)benzofuran-2-yl)-3,5-dimethyl-4-hydroxy-2H-pyran-2-one;
6-(5-(3,4-dichlorobenzyloxy)benzofuran-2-yl)-3,5-dimethyl-4-hydroxy-2H-pyran-2-one;
6-(5-(4-n-butoxybenzyloxy)benzofuran-2-yl)-3,5-dimethyl-4-hydroxy-2H-pyran-2-one;
3,5-dimethyl-4-hydroxy-6-(6-(1,2,3,4-tetrahydronaphthalen-1-yloxy)benzofuran-2-yl)-2H-pyran-2-one;
3,5-dimethyl-4-hydroxy-6-(5-(2-propyn-1-yloxy)benzofuran-2-yl)-2H-pyran-2-one;
3,5-dimethyl-6-(5-(3-fluorobenzyloxy)benzofuran-2-yl)-4-hydroxy-2H-pyran-2-one;
3,5-dimethyl-6-(5-(4-fluorobenzyloxy)benzofuran-2-yl)-4-hydroxy-2H-pyran-2-one;
3,5-dimethyl-4-hydroxy-6-(5-(3-methoxybenzyloxy)benzofuran-2-yl)-2H-pyran-2-one;
6-(5-(3-chlorobenzyloxy)benzofuran-2-yl)-3,5-dimethyl-4-hydroxy-2H-pyran-2-one;
6-(5-(3-aminobenzyloxy)benzofuran-2-yl)-3,5-dimethyl-4-hydroxy-2H-pyran-2-one;
6-(5-(3-(t-butoxycarbonylamino)benzyloxy)benzofuran-2-yl)-3,5-dimethyl-4-hydroxy-2H-pyran-2-one;
4-acetyloxy-6-(5-(3-(t-butoxycarbonylamino)benzyloxy)benzofuran-2-yl)-3,5-dimethyl-2H-pyran-2-one;
4-acetyloxy-3,5-dimethyl-6-(5-trifluoromethanesulfonyloxy-benzofuran-2-yl)-2H-pyran-2-one;
4-acetyloxy-3,5-dimethyl-6-(5-(methoxycarbonyl)benzofuran-2-yl)-2H-pyran-2-one;
4-acetyloxy-6-(4-benzyloxybenzofuran-2-yl)-3,5-dimethyl-2H-pyran-2-one;
4-acetyloxy-6-(4-acetyloxybenzofuran-2-yl)-3,5-dimethyl-2H-pyran-2-one;
4-acetyloxy-3,5-dimethyl-6-(5-methoxybenzofuran-2-yl)-2H-pyran-2-one;
4-acetyloxy-6-(5-benzyloxybenzofuran-2-yl)-3,5-dimethyl-2H-pyran-2-one;
6-(5-benzyloxybenzofuran-2-yl)-3,5-dimethyl-4-hydroxy-2H-pyran-2-one;
4-acetyloxy-3,5-dimethyl-6-(5-p-toluenesulfonyloxy-benzofuran-2-yl)-2H-pyran-2-one;
4-acetyloxy-6-(7-benzyloxybenzofuran-2-yl)-3,5-dimethyl-2H-pyran-2-one;
3,5-dimethyl-4-hydroxy-6-(5-(methoxycarbonyl)benzofuran-2-yl)-2H-pyran-2-one;
3,5-dimethyl-4-hydroxy-6-(6-methoxymethoxybenzofuran-2-yl)-2H-pyran-2-one.

The compounds represented by structural formula (I) above will sometimes form acid addition salts or base addition salts. As specific examples of acid addition salts there may be mentioned addition salts of mineral acids such as hydrochloric acid, hydrobromic acid, sulfuric acid, nitric acid and phosphoric acid; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid and ethanesulfonic acid; and acidic amino acids such as aspartic acid and glutamic acid; as specific examples of base addition salts there may be mentioned salts of metals such as lithium, sodium and potassium; salts of divalent or trivalent metals such as magnesium, calcium, zinc and aluminum; addition salts of basic amino acids such as lysine and arginine; as well as salts of ammonium and organic ammonium such as methylammonium, dimethylammonium, trimethylammonium, benzylammonium and monoethanolammonium. The present invention also encompasses hydrates of the compounds represented by structural formula (I), as well as their various solvates and crystal polymorphs.

The compounds of the invention may generally be produced by the processes outlined below in Production Processes 1 to 5, with modifications if necessary, using readily available starting substances, reagents and common synthesis methods.

Production Process 1

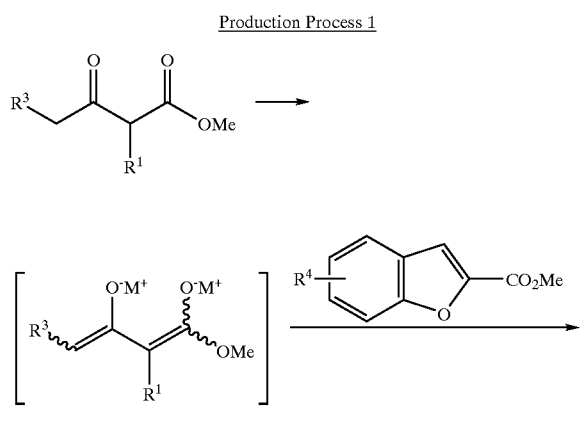

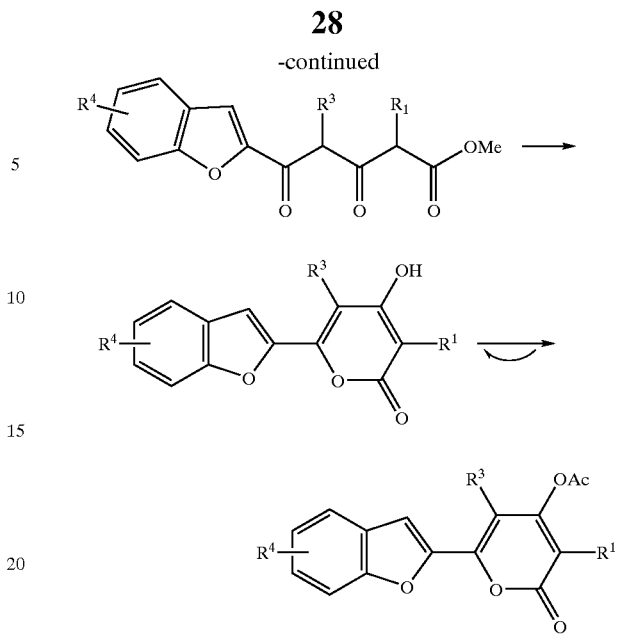

Specifically, for example, a benzofuryl-α-pyrone derivative of the invention may be produced by the method shown as Production Process 1. A solution, such as a THF solution, of a 2,4-disubstituted-β-keto ester is treated with 2 equivalents of a base, for example, 1 equivalent of NaH and 1 equivalent of n-BuLi, or 2 equivalents of LDA, to prepare a dienolate, and then a benzofurancarboxylic acid ester derivative is allowed to act thereon for Claisen condensation to obtain a diketo ester intermediate. The diketo ester intermediate is subjected to alkali hydrolysis and then acid treatment to obtain an α-pyrone. The diketo ester intermediate can be subjected to alkali hydrolysis followed by acid treatment and then treatment with acetic anhydride and pyridine to obtain 4-acetyloxy-α-pyrone, and this may be again subjected to alkali hydrolysis to yield 4-hydroxy-α-pyrone. Alternatively, the diketo ester intermediate may be treated with an acid such as sulfuric acid, polyphosphoric acid or p-TsOH or heat treated under reduced pressure, to obtain 4-hydroxy-α-pyrone.

Production Process 2

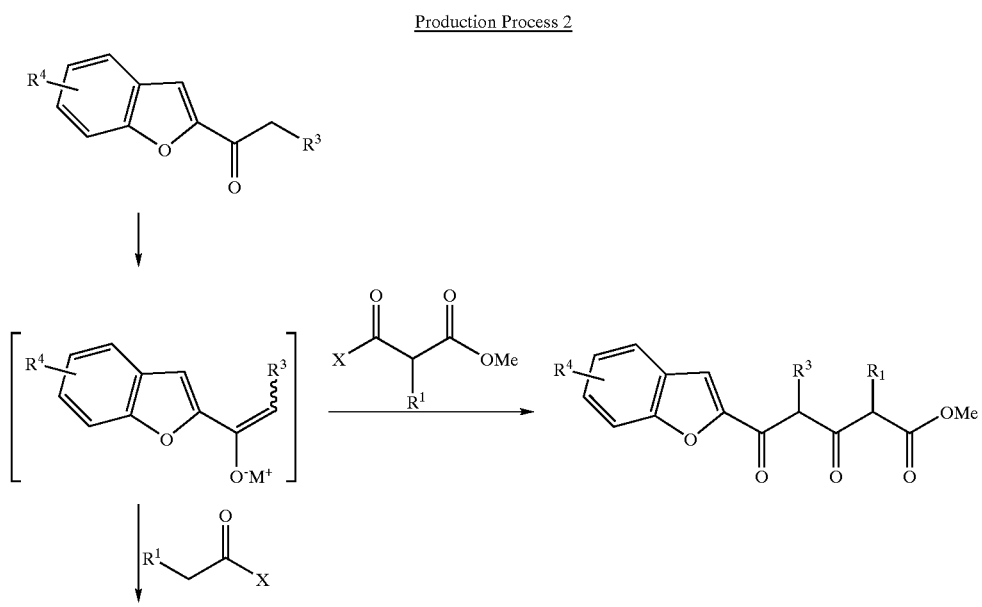

-continued

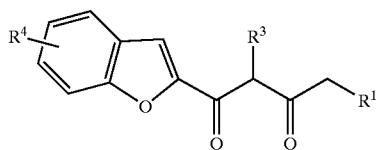 → 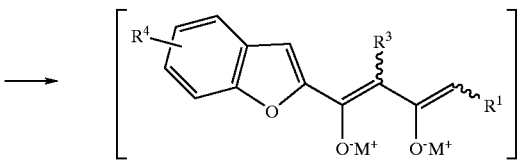

The diketo ester intermediate of Production Process 1 can also be produced by another method outlined as Production Process 2. A benzofurylketone is treated with a base such as LDA to prepare an enolate, and this is reacted with a malonic acid ester, such as malonic monomethyl ester-monochloride, to obtain a diketo ester intermediate. Alternatively, a diketo ester intermediate may be obtained by a process wherein a diketone obtained by reacting an acid chloride or ester with a benzofurylketone enolate is treated with 2 equivalents of a base such as LDA to prepare a dienolate, which is then reacted with a $CO_2$-related compound such as carbon dioxide gas or dimethyl carbonate.

Production Process 3

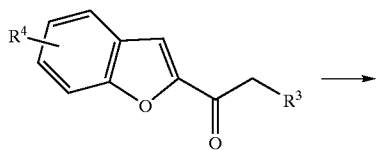

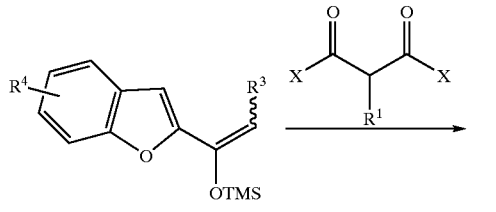

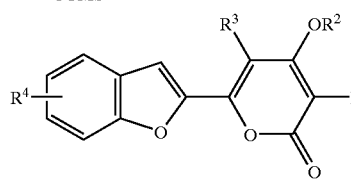

A benzofuryl-α-pyrone derivative of the invention may also be produced by the method shown as Production Process 3. A benzofuryl-α-pyrone derivative can be obtained by a method in which a benzofurylketone is converted to a silylenol ether with TMSCl-$Et_3$ or TMSOTf-$Et_3$, for example, and this is reacted with malonic dichloride or a malonic diester.

Production Process 4

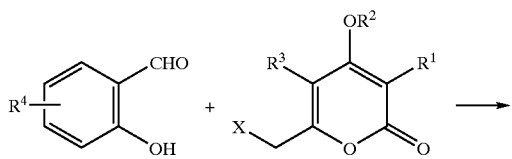

-continued

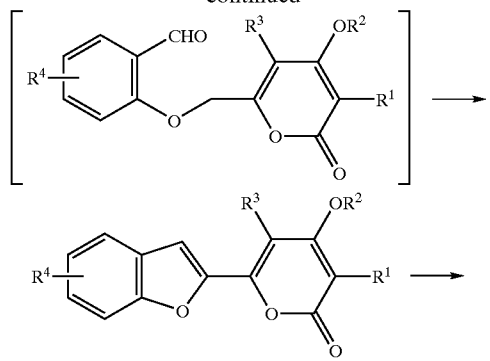

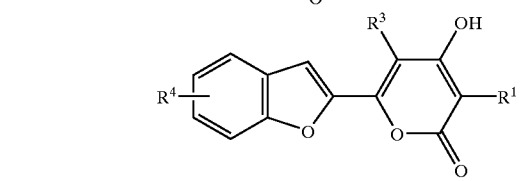

A benzofuryl-α-pyrone derivative of the invention may also be produced by the method shown as Production Process 4. A benzofuryl-α-pyrone derivative can be obtained by a method in which an α-pyrone derivative with a —$CH_2X$ substituent at the 6-carbon (wherein X represents a leaving group such as Cl, Br, I, OMs or OTf) is reacted with a substituted salicyl aldehyde in the presence of a base such as $K_2CO_3$ and/or DBU.

Production Process 5

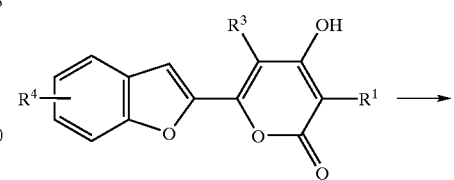

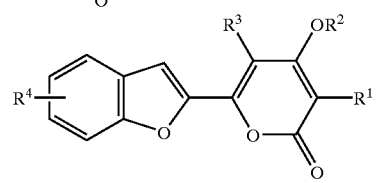

Benzofuryl-α-pyrone derivatives of the invention wherein $R^2$ (wherein $R^2$ represents a group as defined above) is $COR^5$ or $SO_2R^6$ (wherein $R^5$ and $R^6$ represent groups as defined above) can be produced by the method shown as Production Process 5. Of the benzofuryl-α-pyrone derivatives according to the invention, a benzofuryl-α-pyrone derivative wherein $R^2$ is —$COR^5$ may be produced by a method wherein a starting material, 6-benzofuryl-4- hydroxy-α-pyrone derivative obtained by any of Production Processes 1 to 4 above, with modifications if necessary, is reacted with an acid chloride or acid anhydride in the presence of a base, for example, a tertiary amine such as Et₃N or a nitrogen-containing aromatic heterocycle such as pyridine or imidazole, or alternatively, a method wherein the starting material is reacted with a carboxylic acid in the presence of a condensation agent such as WSC-HOBt, DCC-HOBt, CDI, diethyl cyanophosphate or diphenylphosphoryl azide, or by a method using the "Mitsunobu reaction" wherein the starting material is reacted with a carboxylic acid in the presence of Ph₃P-DEAD. Similarly, a benzofuryl-α-pyrone derivative wherein R² is SO₂R⁶ may be produced by reacting a starting material, 6-benzofuryl-4-hydroxy-α-pyrone derivative, with a sulfonyl chloride derivative represented by RSO₂Cl, in the presence of a base, for example, a tertiary amine such as Et₃N or a nitrogen-containing aromatic heterocycle such as pyridine or imidazole.

Benzofuryl-α-pyrone derivatives of the present invention wherein R⁴ is a substituent as defined above other than hydrogen can be produced by the method shown as Production Process 6 or 7. As shown in Production Process 6, a readily available substituted salicyl aldehyde derivative is used as the starting material for any of Production Processes 1 to 5 above, with modifications if necessary, to obtain a benzofuryl-α-pyrone (route A) or a 2-benzofurancarboxylic acid ester intermediate (route B) substituted with hydroxy, methoxy, formyl, bromo, nitro, etc. Route A is a method involving functional group conversion from the hydroxy, methoxy, formyl, bromo or nitro substituent at the benzofuryl-α-pyrone stage, while route B is a method wherein the α-pyrone ring is constructed after functional group conversion of R⁴ at the 2-benzofurancarboxylic acid ester intermediate stage.

Production Process 6

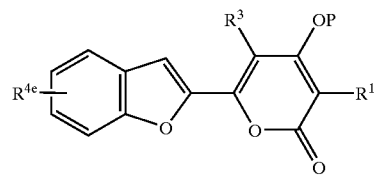

P = H, Ac, MOM
R⁴ᵉ = OMe, OH, OTf, CHO, Br, NO₂

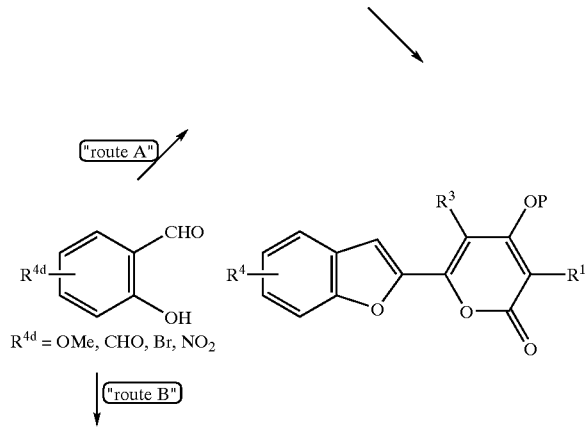

R⁴ᵈ = OMe, CHO, Br, NO₂

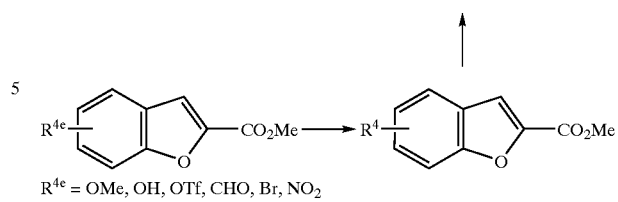

R⁴ᵉ = OMe, OH, OTf, CHO, Br, NO₂

Production Process 7

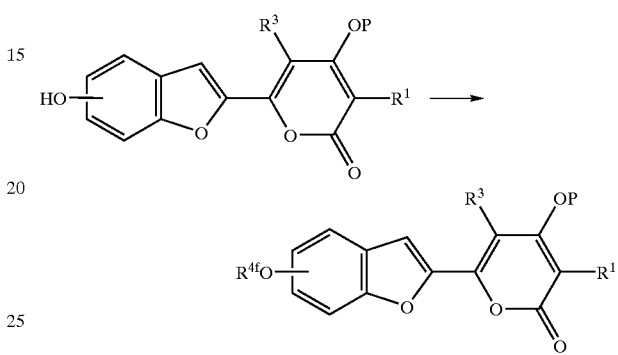

R⁴ᶠ = alkyl, acyl, sulfonyl etc.

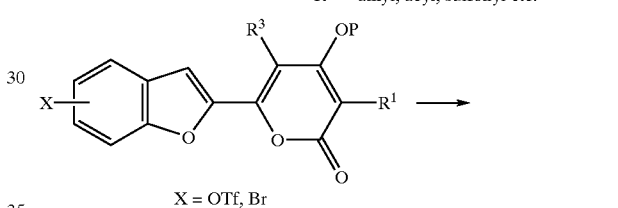

X = OTf, Br

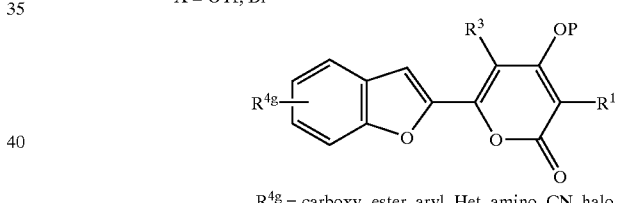

R⁴ᵍ = carboxy, ester, aryl, Het, amino, CN, halo

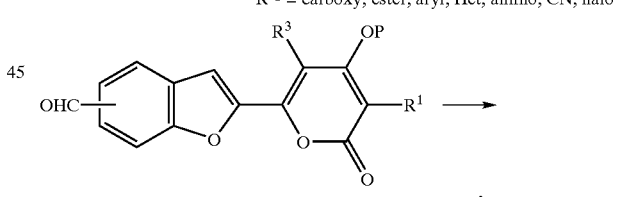

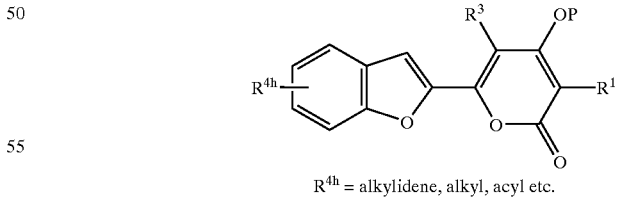

R⁴ʰ = alkylidene, alkyl, acyl etc.

The functional group conversion of R⁴ from hydroxy, methoxy, formyl, bromo, nitro, etc. can be accomplished by the method shown in Production Process 7. For the benzofuran-α-pyrone intermediate obtained by route A in Production Process 6, functional group conversion from hydroxyl may be accomplished by acylation with an acid chloride or acid anhydride, sulfonylation with sulfonyl chloride or sulfonic anhydride, alkylation by the Mitsunobu reaction, etc.; functional group conversion from bromo or trifluoromethanesulfonyloxy may be accomplished by carbonylation, allylation, cyanation, halogenation, amination, etc. with a transition metal catalyst such as a palladium catalyst, for example; and functional group conversion from formyl may be accomplished by alkylation or acylation with a nucleophilic agent such as an organometallic reagent or an enolate.

Functional group conversion of $R^4$ from a 2-benzofurancarboxylic acid ester intermediate obtained by route B of Production Process 6 can also be accomplished using the same method of Production Process 7.

Production Processes 1 to 7 shown above are not intended to restrict the synthesis processes for the compounds of the invention, and any other processes known in the art may also be used.

Benzofuryl-α-pyrone derivatives of the invention and their salts that are obtained in the manner described above have a triglyceride biosynthesis inhibiting effect, a blood triglyceride lowering effect and a blood HDL elevating effect, as demonstrated by Examples given below, and can therefore be used as active ingredients, in combination with the carriers, etc. described below if necessary, to provide pharmaceutical compositions, and to provide triglyceride biosynthesis inhibitors, blood triglyceride lowering agents or blood HDL elevating agents according to the invention.

For clinical application of a benzofuryl-α-pyrone derivative of the invention or its salt as a prophylactic or therapeutic agent for hypertriglyceridemia, arteriosclerosis or the like, it may be administered orally or parenterally such as intrarectally, subcutaneously, intramuscularly, intravenously or percutaneously, but oral or intravenous administration is preferred.

For oral administration, it may be in the form of a solid or liquid preparation. Solid preparations include tablets, pills, powders and granules. The active substances in such solid preparations are blended with pharmacologically acceptable carriers such as sodium bicarbonate, calcium carbonate, potato starch, sucrose, mannitol and carboxymethyl cellulose. The formulation may be carried out by a common method, and other additives, for example, lubricants such as calcium stearate and magnesium stearate, may also be included for formulation in addition to the carrier. Enteric coated preparations may also be prepared having an enteric coating formed by spraying the above-mentioned solid preparations with, for example, an aqueous solution or an organic solvent solution of an enteric coating substance such as cellulose acetate phthalate, hydroxypropylmethyl cellulose phthalate, polyvinyl alcohol phthalate or styrene-maleic anhydride copolymer, or a methacrylic acid or methyl methacrylate copolymer. Solid preparations such as powders or granules may also be encapsulated,by enteric coated capsules.

A liquid preparation for oral administration contains, for example, an emulsifier, solution, suspension, syrup or elixir. These preparations contain conventionally used pharmacologically acceptable carriers such as water or liquid paraffin. Oily bases such as coconut oil, fractionated coconut oil, soybean oil or corn oil are also used as carriers. Pharmacologically acceptable carriers also contain, when necessary, commonly used adjuvants, aromatics, stabilizers or preservatives. A liquid preparation may be administered in the form of a capsule formed from an absorbable substance such as gelatin. Solid preparations for intrarectal administration include suppositories that are produced by known methods to contain the active ingredient.

A preparation for parenteral administration is administered as a sterile aqueous or non-aqueous solution, suspension or emulsion. A non-aqueous solution or suspension may contain propyl glycol, polyethylene glycol, a vegetable oil such as olive oil or soybean oil or an injectable organic ester such as ethyl oleate, as pharmacologically acceptable carriers. Such preparations may also contain adjuvants such as preservatives, humectants, emulsifiers, dispersers and stabilizers. These solutions, suspensions and emulsions may be sterilized by appropriate means such as, for example, filtration through a bacteria-retaining filter, heating, inclusion of a sterilizing agent or treatment with ultraviolet irradiation. After production and just prior to use of the sterile solid preparation, it may be dissolved in sterile water or a sterile injection solvent for use. Fatty emulsions prepared by adding water to a uniform solution of the active ingredients with a vegetable oil such as soybean oil and a phospholipid such as lecithin, may be homogenized with a homogenizer such as a pressure jet homogenizer or an ultrasonic homogenizer to be used as injections.

Percutaneous administration dosage forms include ointments, creams and the like. These may be produced by common methods.

When an active ingredient according to the invention is used as a treatment agent for hypertriglyceridemia or as a prophylactic agent for arteriosclerosis, it may usually be administered at about 1 to 1000 mg per day for adults, though this will depend on the patient's condition, age, gender and body weight and the route of administration. The dosage may be administered either at one time, or over a few times, such as 2 to 6 times, per day.

The various routes of administration are preferably selected based on the absorption efficiency in the body for the particular physiologically active benzofuryl-α-pyrone derivative, as determined by well-known pharmacological methods.

EXAMPLES

The abbreviations used for the derivatives used throughout the present specification including the examples, and for the groups within their structures and the reagents used, are those commonly used in the field of organic chemistry; the meanings of the abbreviations are given below.

THF: tetrahydrofuran, $Et_2O$: diethyl ether, DMF: N,N-dimethylformamide, AcOEt: ethyl acetate, MeOH: methanol, EtOH: ethanol, DBU: 1,8-diazabicyclo[5.4.0]-7-undecene, DEAD: diethyl azodicarboxylate, TMAD: azodicarboxylic acid bis(dimethylamide), DMSO: dimethylsulfoxide, $Et_3N$: triethylamine, Py: pyridine, n-BuLi: normal-butyllithium, LDA: lithium diisopropylamide, $Ac_2O$: acetic anhydride, WSC: 1-(3-dimethylaminopropyl)-3-ethylcarbodiimide hydrochloride, DCC: 1,3-dicyclohexylcarbodiimide, CDI: carbonyldiimidazole, HOBt: 1-hydroxybenzotriazole, PPTS: pyridinium para-toluenesulfonate, TMSOTf: trimethylsilyl trifluoromethanesulfonate, TfOH: trifluoromethanesulfonic acid, Ms: methanesulfonyl, Tf: trifluoromethanesulfonyl, p-Ts: para-toluenesulfonyl, Ph: phenyl, Bu: butyl, Bzl: benzyl, Ac: acetyl, TMS: trimethylsilyl Production Examples Synthesis of Intermediates Synthesis of methyl 2-benzofurancarboxylate After adding thionyl chloride (3.80 ml) to a solution of 2-benzofurancarboxylic acid (2.00 g) in MeOH (60 ml) at −40° C., the mixture was stirred for 19 hours while the temperature gradually increased to room temperature. The reaction solution was concentrated under reduced pressure and the residue was purified by silica gel column chromatography (n-hexane/AcOEt=6/1) to obtain methyl 2-benzofurancarboxylate.

Yield: 2.16 g (y. 99.2%)

$^1$H NMR(δ ppm, CDCl$_3$): 3.99(s, 3H), 7.28 to 7.50(m, 2H), 7.54(s, 1H), 7.60(d, J=8.9 Hz, 1H), 7.69(d, J=7.6 Hz, 1H)

Synthesis of methyl 2-methyl-3-oxopentanoate

Methyl iodide (57 ml) and K$_2$CO$_3$ (127 g) were added to a solution of methyl propionylacetate (100 g) in acetone (800 ml) while cooling on ice. The reaction solution was stirred for 96 hours at room temperature and celite filtered, and then the mother liquor was slowly concentrated under reduced pressure and distilled under reduced pressure to obtain methyl 2-methyl-3-oxopentanoate.

Yield: 105 g (y. 94.8%)

$^1$H NMR(δ ppm, CDCl$_3$): 1.08(t, J=7.3 Hz, 3H), 1.35(d, J=7.3 Hz, 3H), 2.45 to 2.72(m, 2H), 3.54(q, J=7.3 Hz, 1H), 3.73(s, 3H)

Synthesis of methyl 3-oxononanoate

Pyridine (11.2 ml) and n-heptanoyl chloride (11.8 ml) were added to a solution of merudoramu acid (10.0 g) in CHCl$_2$ (150 ml) at 0° C., and the mixture was stirred at 0° C. for 30 minutes and then at room temperature for 2 hours. The reaction solution was cooled to 0° C., diluted hydrochloric acid was added and extraction was performed with CH$_2$Cl$_2$. The organic layer was rinsed with water and saturated saline, dried with Na$_2$SO$_4$ and then filtered and concentrated. MeOH (150 ml) was added to the residue prior to heated reflux for 3 hours. After cooling, the reaction solution was concentrated under reduced pressure and the residue was purified by silica gel column chromatography (n-hexane/AcOEt=13/1) to obtain methyl 3-oxononanoate.

Yield: 8.51 g (y. 65.9%)

$^1$H NMR(δ ppm, CDCl$_3$): 0.88(t, J=6.9 Hz, 3H), 1.22 to 1.40(m, 6H), 1.51 to 1.69(m, 2H), 2.53(t, J=7.3 Hz, 2H), 3.45(s, 2H), 3.74(s, 3H)

Synthesis of methyl 2-methyl-3-oxononanoate

K$_2$CO$_3$ (2.67 g) was added to a solution of methyl 3-oxononanoate (3.01 g) and methyl iodide (2.77 g) in acetone (100 ml) and the mixture was stirred at room temperature for 24 hours. The reaction solution was celite filtered, and then the mother liquor was concentrated under reduced pressure and the residue was purified by silica gel column chromatography (n-hexane/AcOEt=13/1) to obtain methyl 2-methyl-3-oxononanoate.

Yield: 3.06 g (y. 94.6%)

$^1$H NMR(δ ppm, CDCl$_3$): 0.90(t, J=6.9 Hz, 3H), 1.21 to 1.39(m, 9H), 1.51 to 1.65(m, 2H), 2.47 to 2.56(m, 2H), 3.53(q, J=7.3 Hz, 1H), 3.73(s, 3H)

Synthesis of ethyl 2-(benzyloxy)acetate

Benzyl alcohol (27.5 ml) was added to a suspension of NaH (1.1 g) in Et$_2$O (250 ml) at 0° C., and after stirring at 0° C. for 10 minutes and at room temperature for 5 minutes, the reaction solution was cooled to −10 to 0° C. and trichloroacetonitrile (27 ml) was added dropwise over 15 minutes. The reaction solution was stirred for one hour while the temperature slowly increased to room temperature, and was then concentrated under reduced pressure. A solution of MeOH (1.0 ml) in n-pentane (100 ml) was added to the residue, and the mixture was vigorously stirred, filtered and concentrated. After then adding n-pentane to the residue and refiltering, the mother liquor was concentrated. Et$_2$O (80 ml), n-pentane (80 ml) and ethyl glycolate (25 g) were added to the residue, and then TfOH (1.5 ml) was added at 0° C. and the mixture was stirred at 0° C. for 10 minutes and at room temperature for 2 hours. The reaction solution was filtered, the mother liquor was poured into a saturated NaHCO$_3$ aqueous solution and extraction was performed with Et$_2$O. The organic layer was rinsed with water and dried with MgSO$_4$, and then filtered and concentrated. The residue was purified by silica gel column chromatography (n-hexane/AcOEt=10/1→6/1) to obtain ethyl 2-(benzyloxy)acetate.

Yield: 38.76 g (y. 83.2%)

$^1$H NMR(δ ppm, CDCl$_3$): 1.29(t, J=7.26 Hz, 3H), 4.09(s, 2H), 4.23(q, J=7.26 Hz, 2H), 4.63(s, 2H), 7.21 to 7.45(m, 5H)

Synthesis of methyl 6-benzyloxy-2,4-dimethyl-3,5-dioxohexanoate

A solution of methyl 2-methyl-3-oxopentanoate (13.05 g) in THF (100 ml) was added to a suspension of NaH (3.80 g) in THF (100 ml) at 0° C., and after stirring at 0° C. for 15 minutes, 1.63 M n-BuLi (58 ml) was added and the mixture was stirred at 0° C. for 20 minutes to prepare a light yellow dienolate. The reaction solution was cooled to −78° C., a solution of ethyl 2-(benzyloxy)acetate (17.56 g) in THF (30 ml) was added, and the mixture was stirred at −78° C. for 5 minutes and then at 0° C. for one hour. Diluted hydrochloric acid was poured into the reaction solution for quenching, and extraction was performed with AcOEt at near neutral. The organic layer was rinsed with saturated saline and dried with MgSO$_4$, and then filtered and concentrated. The residue was purified by silica gel column chromatography (n-hexane/AcOEt=5/1→3/1) to obtain methyl 6-benzyloxy-2,4-dimethyl-3,5-dioxohexanoate.

Yield: 9.78 g (y. 37%)

$^1$H NMR(δ ppm, CDCl$_3$): 1.17 to 1.42(m, 6H), 3.62 to 3.80(m, 4H), 3.98 to 4.28(m, 3H), 4.48 to 4.65(m, 2H), 7.12 to 7.42(m, 5H)

Synthesis of 4-acetyloxy-6-(benzyloxy)methyl-3,5-dimethyl-2H-pyran-2-one

An aqueous solution (6 ml) of LiOH-hydrate (64 mg) was added to a solution of methyl 6-benzyloxy-2,4-dimethyl-3,5-dioxohexanoate (430 mg) in THF (10 ml), and the mixture was stirred at room temperature for 1.5 hours. The reaction solution was neutralized with diluted hydrochloric acid, and after distilling off the volatile components under reduced pressure, extraction was performed with AcOEt at pH 3. The organic layer was dried with MgSO$_4$ and then filtered and concentrated. Ac$_2$O (6 ml) was added to the residue, and after stirring at room temperature for 30 minutes, pyridine (4 ml) was added and the mixture was stirred at room temperature for one hour. The reaction solution was concentrated under reduced pressure, and the residue was purified by silica gel column chromatography (n-hexane/AcOEt=3/1→12/5) to obtain 4-acetyloxy-6-(benzyloxy)methyl-3,5-dimethyl-2H-pyran-2-one.

Yield: 212 mg (y. 47.7%)

$^1$H NMR(δ ppm, CDCl$_3$): 1.88(s, 3H), 1.93(s, 3H), 2.34(s, 3H), 4.35(s, 2H), 4.58(s, 2H), 7.23 to 7.41(m, 5H)

Synthesis of 6-(benzyloxy)methyl-3,5-dimethyl-4-hydroxy-2H-pyran-2-one

K$_2$CO$_3$ (3.0 g) and water (10 ml) were added to a solution of 4-acetyloxy-6-(benzyloxy)methyl-3,5-dimethyl-2H-pyran-2-one (6.08 g) in MeOH (100 ml), and after stirring at room temperature overnight, the reaction solution was celite filtered and the mother liquor was concentrated under reduced pressure. Water was added to the residue, extraction was performed with AcOEt, and the organic layer was dried with Na$_2$SO$_4$ and then filtered and concentrated. The residue was purified by silica gel column chromatography (n-hexane/AcOEt=5/1→1/1) to obtain 6-(benzyloxy)methyl-3,5-dimethyl-4-hydroxy-2H-pyran-2-one.

Yield: 4.82 g (y. 86%)

(TLC Rf=0.3; n-hexane/AcOEt=1/1)

Synthesis of 6-(benzyloxy)methyl-3,5-dimethyl-4-methoxymethoxy-2H-pyran-2-one Diisopropylethylamine (2.1 ml) was added to a solution of 6-(benzyloxy)methyl-3,5-dimethyl-4-hydroxy-2H-pyran-2-one (2.60 g) in THF (50 ml), and after stirring the mixture at room temperature for one hour, chloromethyl methyl ether (921 μl) was added at 0° C. and the mixture was stirred at room temperature for one hour. After concentrating the reaction solution under reduced pressure, water was added to the residue, extraction was performed with AcOEt, and the organic layer was dried with Na$_2$SO$_4$ and then filtered and concentrated. The residue was purified by silica gel column chromatography (n-hexane/AcOEt=5/1→1/1) to obtain 6-(benzyloxy)methyl-3,5-dimethyl-4-methoxymethoxy-2H-pyran-2-one.

Yield: 1.80 g (y. 60%)

(TLC Rf=0.6; n-hexane/AcOEt=1/1)

Synthesis of 3,5-dimethyl-6-hydroxymethyl-4-methoxymethoxy-2H-pyran-2-one

20% Pd(OH)$_2$/C (360 mg) was added to a solution of 6-(benzyloxy)methyl-3,5-dimethyl-4-methoxymethoxy-2H-pyran-2-one (1.80 g) in EtOH (50 ml), and the mixture was vigorously stirred at room temperature for 3 hours under a hydrogen gas atmosphere. The reaction solution was celite filtered and the mother liquor was concentrated under reduced pressure. The residue was purified by silica gel column chromatography (n-hexane/AcOEt=1/1) to obtain 3,5-dimethyl-6-hydroxymethyl-4-methoxymethoxy-2H-pyran-2-one.

Yield: 1.26 g (y. 99%)

(TLC Rf=0.15; n-hexane/AcOEt=1/1)

Synthesis of 3,5-dimethyl-4-methoxymethoxy-6-(methylsulfonyloxy)methyl-2H-pyran-2-one Triethylamine (606 mg) was added to a solution of 3,5-dimethyl-6-hydroxymethyl-4-methoxymethoxy-2H-pyran-2-one (1.26 g) in THF (50 ml), and after stirring the mixture at room temperature for one hour, methanesulfonyl chloride (1.05 g) was added and the mixture was stirred at room temperature overnight. Water was added to the reaction solution, extraction was performed with AcOEt, and the organic layer was dried with Na$_2$SO$_4$ and then filtered and concentrated. The residue was purified by silica gel column chromatography (n-hexane/AcOEt=1/1) to obtain 3,5-dimethyl-4-methoxymethoxy-6-(methylsulfonyloxy)methyl-2H-pyran-2-one.

Yield: 1.35 g (y. 73%)

(TLC Rf=0.5; n-hexane/AcOEt=1/1)

Synthesis of 6-bromomethyl-3.5-dimethyl-4-methoxymethoxy-2H-pyran-2-one

Sodium bromide (500 mg) was added to a solution of 3,5-dimethyl-4-methoxymethoxy-6-(methylsulfonyloxy)methyl-2H-pyran-2-one (1.35 g) in DMF (20 ml), and after the stirring the mixture at room temperature for one hour, the reaction solution was concentrated under reduced pressure. Water was added to the residue, extraction was performed with AcOEt, and the organic layer was dried with Na$_2$SO$_4$ and then filtered and concentrated. The residue was purified by silica gel column chromatography (n-hexane/AcOEt=1/1) to obtain 6-bromomethyl-3,5-dimethyl-4-methoxymethoxy-2H-pyran-2-one.

Yield: 1.21 g (y. 99%)

(TLC Rf=0.7; n-hexane/AcOEt=1/1)

Synthesis of methyl 6-hydroxybenzofuran-2-carboxylate

A suspension of 4-methoxysalicyl aldehyde (50 g), K$_2$CO$_3$ (65 g) and methyl bromoacetate (65 g) in DMF (500 ml) was stirred at 60° C. for one hour, and after cooling, the reaction solution was concentrated under reduced pressure. Water was added to the residue, extraction was performed with AcOEt, and the organic layer was dried with MgSO$_4$ and then filtered and concentrated. Toluene (500 ml) was added to the residue to make a suspension, and upon addition of DBU (70 g), the mixture was stirred at 130° C. overnight. After cooling, the reaction solution was concentrated under reduced pressure, water was added to the residue and extraction was performed with AcOEt. The organic layer was dried with MgSO$_4$ and then filtered and concentrated. The residue was dissolved in MeOH (500 ml), concentrated hydrochloric acid (50 ml) was added and the mixture was stirred at 60° C. overnight. After cooling, the reaction solution was concentrated under reduced pressure, AcOEt (500 ml) was added to the residue, a saturated NaHCO$_3$ aqueous solution (500 ml) was slowly added to separate the organic layer and aqueous layer, and the aqueous layer was extracted with AcOEt. The organic layer was dried with MgSO$_4$ and then filtered and concentrated. The residue was dissolved in CH$_2$Cl$_2$ (1000 ml), boron tribromide (125 g) was slowly added at 0° C., and then the mixture was stirred at room temperature for 24 hours. The reaction solution was concentrated under reduced pressure, the resulting brown oil was dissolved in MeOH (500 ml), concentrated hydrochloric acid (50 ml) was further added and the mixture was stirred at 60° C. overnight. After cooling, the reaction solution was concentrated under reduced pressure, AcOEt (500 ml) was added to the residue, a saturated NaHCO$_3$ aqueous solution (500 ml) was slowly added to separate the organic layer and aqueous layer, and the aqueous layer was extracted with AcOEt. The organic layer was dried with MgSO$_4$ and then filtered and concentrated.

The residue was purified by silica gel column chromatography (n-hexane/AcOEt=3/1) to obtain methyl 6-hydroxybenzofuran-2-carboxylate.

Yield: 37.9 g (y. 60%)

$^1$H NMR(δ ppm, CDCl$_3$): 3.88(s, 3H), 5.50 to 6.50(brs, 1H), 6.80 to 7.80(m, 4H)

Synthesis of methyl 6-(benzyloxy)benzofuran-2-carboxylate

A solution of methyl 6-hydroxybenzofuran-2-carboxylate (3.58 g) in THF (30 ml) was slowly added to a suspension of NaH (800 mg) in THF (100 ml) at room temperature, and after stirring for one hour, DMF (35 ml) was added, benzyl bromide (3.77 g) was slowly added and the mixture was stirred for one hour. Water was added to the reaction solution, extraction was performed with AcOEt, and the organic layer was dried with $MgSO_4$ and then filtered and concentrated. The residue was purified by silica gel column chromatography (n-hexane/AcOEt=10/1) to obtain methyl 6-(benzyloxy)benzofuran-2-carboxylate.

Yield: 4.85 g (y. 95%)

$^1$H NMR($\delta$ ppm, $CDCl_3$): 3.95(s, 3H), 5.19(5, 2H), 6.85 (dd, J=8.1 Hz, 2.0 Hz, 1H), 7.05(d, J=2.0 Hz, 1H), 7.43(s, 1H), 7.51(d, J=8.1 Hz, 1H)

Synthesis of 2-hydroxy-4-morpholinobenzaldehyde

After slowly adding a solution of 3-morpholinophenol (5.0 g) in THF (100 ml) to a 3 M diethyl ether solution (10 ml) of ethylmagnesium bromide, the mixture was stirred at 30° C. for 1.5 hours. Paraformaldehyde (3.0 g) and $Et_3N$ (3.0 g) were added to the reaction solution and the mixture was stirred at 80° C. for 4 hours. After cooling, a 6 N hydrochloric acid aqueous solution (20 ml) was added, the mixture was stirred for an hour, and then the organic layer and aqueous layer were separated and the aqueous layer was rendered weakly alkaline prior to extraction with AcOEt. The organic layers were combined and dried with $MgSO_4$, and then filtered and concentrated. The residue was purified by silica gel column chromatography (n-hexane/AcOEt=3/1) to obtain 2-hydroxy-4-morpholinobenzaldehyde.

Yield: 3.57 g (y. 62%)

$^1$H NMR($\delta$ ppm, $CDCl_3$): 3.30(t, J=4.8 Hz, 4H), 3.84(t, J=4.8 Hz, 4H), 6.18(d, J=2.1 Hz, 1H), 6.55(dd, J=8.9 Hz, 2.1 Hz, 1H), 7.78(d, J=8.9 Hz, 1H), 10.30(s, 1H)

Synthesis of methyl 6-morpholinobenzofuran-2-carboxylate

Methyl bromoacetate (3.0 g) and $K_2CO_3$ (3.0 g) were added to a solution of 2-hydroxy-4-morpholinobenzaldehyde (3.5 g) in acetonitrile (100 ml), and after heated reflux for 16 hours, the reaction solution was filtered and the mother liquor was concentrated under reduced pressure. MeOH (100 ml) and concentrated hydrochloric acid (10 ml) were added to the residue, and after reflux for 5 hours, the reaction solution was concentrated under reduced pressure. A saturated $NaHCO_3$ aqueous solution (100 ml) was added to the residue prior to extraction with AcOEt, and the organic layer was dried with $MgSO_4$ and then filtered and concentrated. The residue was purified by silica gel column chromatography (n-hexane/AcOEt=5/1) to obtain methyl 6-morpholinobenzofuran-2-carboxylate.

Yield: 3.1 g (y. 71%)

$^1$H NMR($\delta$ ppm, $CDCl_3$): 3.22(t, J=4.8 Hz, 4H), 3.80(t, J=4.8 Hz, 4H), 3.95(s, 3H), 6.96 to 7.00(m, 2H), 7.44(s, 1H), 7.53(d, J=8.6 Hz, 1H)

Synthesis of methyl 5-formylbenzofuran-2-carboxylate $K_2CO_3$ (30 g) was added to a solution of 5-formylsalicyl aldehyde (25 g) and methyl bromoacetate (30 g) in acetonitrile (500 ml), and after heated reflux for 24 hours followed by cooling, the reaction solution was filtered and the mother liquor was concentrated under reduced pressure. A saturated ammonium chloride aqueous solution (100 ml) was added to the residue prior to extraction with AcOEt, and the organic layer was dried with $MgSO_4$ and then filtered and concentrated. The residue was purified by silica gel column chromatography (n-hexane/AcOEt=5/1) to obtain methyl 5-formylbenzofuran-2-carboxylate.

Yield: 15 g (y. 44%)

Mass analysis: [$M^+$+H]=205.2

Synthesis of methyl 5-(dimethoxymethyl)benzofuran-2-carboxylate

Methyl orthoformate (1.0 g) and polymer-bound PPTS (1.0 g) were added to a solution of methyl 5-formylbenzofuran-2-carboxylate (15 g) in MeOH (100 ml), and after allowing the mixture to stand at room temperature for 8 hours, the reaction solution was filtered and the mother liquor was concentrated under reduced pressure. The residue was purified by silica gel column chromatography (n-hexane/AcOEt=9/1) to obtain methyl 5-(dimethoxymethyl)benzofuran-2-carboxylate.

Yield: 10 g (y. 54%)

$^1$H NMR($\delta$ ppm, $CDCl_3$): 3.35(s, 3H), 3.98(s, 3H), 5.49(s, 1H), 7.53 to 7.61(m, 3H), 7.81(s, 1H)

The following compound was produced by a process similar to the preceding production example, using organic chemical techniques well-known to those skilled in the art.

Ethyl 5-bromobenzofuran-2-carboxylate $^1$H NMR($\delta$ ppm, $CDCl_3$): 1.43(t, J=7.3 Hz, 3H), 4.45(q, J=7.3 Hz, 2H), 7.45(s, 1H), 7.47(d, J=8.4 Hz, 1H), 7.54(dd, J=8.4 Hz, 2.2 Hz, 1H), 7.82(d, J=2.2 Hz, 1H)

Example 1

Synthesis of 4-acetyloxy-6-(benzofuran-2-yl) -3, 5-dimethyl-2H-pyran-2-one

After adding 60% NaH (220 mg) to a solution of methyl 2-methyl-3-oxopentanoate (750 mg) in THF (5 ml) at 0° C. and stirring at 0° C. for 5 minutes, the mixture was cooled to −78° C. To this reaction solution there was added 1.63 M n-BuLi (3.3 ml), and the mixture was stirred at −78° C. for 30 minutes to prepare a dienolate. A solution of methyl 2-benzofurancarboxylate (300 mg) in THF (10 ml) was added to the dienolate, and the mixture was stirred at −78° C. for 20 minutes. The reaction solution was allowed to return to 0° C., aqueous $KHSO_4$ was added for quenching, and extraction was performed with AcOEt. The organic layer was rinsed with saturated saline and dried with $MgSO_4$, and then filtered and concentrated. The residue was crudely purified by silica gel column chromatography (n-hexane/AcOEt=3/1→2/1) to obtain methyl 5-(benzofuran-2-yl)-2,4-dimethyl-3,5-dioxopentanoate.

Yield: 433 mg (mixture)

An aqueous solution (30 ml) of LiOH-hydrate (2.62 g) was added to a solution of 5-(benzofuran-2-yl)-2,4-dimethyl-3,5-dioxopentanoate (14.98 g) in MeOH (50 ml), and after stirring at room temperature for 20 minutes, the MeOH was distilled off under reduced pressure. The aqueous solution of the residue was rinsed with $Et_2O$ and then cooled on ice, and a $KHSO_4$ aqueous solution was added for adjustment to pH 2.0 to 2.5. The precipitated crystals were filtered off and rinsed with water. The mother liquor was saturated with saline and extracted with AcOEt, and the organic layer was concentrated. The residue was combined with the filtered off crystals, and after adding pyridine (40 ml) and $Ac_2O$ (40 ml), the mixture was stirred at room temperature for 3.5 hours. The reaction solution was concentrated under reduced pressure and the residue was recrystallized from n-hexane/AcOEt=3/1 to obtain 4-acetyloxy-6-(benzofuran-2-yl)-3,5-dimethyl-2H-pyran-2-one.

Yield: 6.11 g (y. 47.3%)

$^1$H NMR($\delta$ ppm, CDCl$_3$): 2.00(s, 3H), 2.31(s, 3H), 2.40(s, 3H), 7.23 to 7.42(m, 2H), 7.36(s, 1H), 7.53(d, J=8.2 Hz, 1H), 7.65(d, J=7.6 Hz, 1H)

Example 2

Synthesis of 6-(benzofuran-2-yl)-3,5-dimethyl-4-hydroxy-2H-pyran-2-one

An aqueous solution (30 ml) of LiOH-hydrate (465 mg) was added to a solution of 4-acetyloxy-6-(benzofuran-2-yl)-3,5-dimethyl-2H-pyran-2-one (3.00 g) in MeOH (100 ml) at 0° C., and after stirring at room temperature for 2 hours, the MeOH was distilled off under reduced pressure. The residue was rinsed with Et$_2$O, and then a KHSO$_4$ aqueous solution was added at 0° C. for adjustment to pH 2.0. The precipitated crystals were filtered off and thoroughly rinsed with water and Et$_2$O in that order and then dried to obtain 6-(benzofuran-2-yl)-3,5-dimethyl-4-hydroxy-2H-pyran-2-one.

Yield: 2.54 g (y. 98.5%)

$^1$H NMR($\delta$ ppm, DMSO-d6): 1.93(s, 3H), 2.28(s, 3H), 7.28 to 7.47(m, 2H), 7.39(s, 1H), 7.68(d, J=8.3 Hz, 1H), 7.74(d, J=7.3 Hz, 1H), 10.91(brs, 1H)

Example 3

Synthesis of 6-(benzofuran-2-yl)-4-benzoyloxy-3,5-dimethyl-2H-pyran-2-one

Pyridine (64 μl) and benzoyl chloride (45 μl) were added to a suspension of 6-(benzofuran-2-yl)-3,5-dimethyl-4-hydroxy-2H-pyran-2-one (40 mg) in CH$_2$Cl$_2$ (5 ml), and the mixture was stirred at room temperature for 50 minutes. The reaction solution was poured into a KHSO$_4$ aqueous solution and extracted with AcOEt, and the organic layer was rinsed with saturated saline and dried with MgSO$_4$, and then filtered and concentrated. The residue was purified by silica gel column chromatography (n-hexane/AcOEt=5/1→4/1) to obtain 6-(benzofuran-2-yl)-4-benzoyloxy-3,5-dimethyl-2H-pyran-2-one.

Yield: 48 mg (y. 71.2%) Light yellow crystals.

$^1$H NMR($\delta$ ppm, CDCl$_3$): 2.04(s, 3H), 2.35(s, 3H), 7.24 to 7.42(m, 3H), 7.49 to 7.77(m, 5H), 8.23(d, J=7.3 Hz, 2H)

Example 4

Synthesis of 6-(benzofuran-2-yl)-3,5-dimethyl-4-methanesulfonyloxy-2H-pyran-2-one Et$_3$N (130 μl) and methanesulfonyl chloride (24 μl) were added to a suspension of 6-(benzofuran-2-yl)-3,5-dimethyl-4-hydroxy-2H-pyran-2-one (40 mg) in THF (5 ml), and the mixture was stirred at room temperature for one hour. The reaction solution was poured into aqueous KHSO$_4$ and extracted with AcOEt, and the organic layer was rinsed with saturated saline and dried with MgSO$_4$, and then filtered and concentrated. The residue was purified by silica gel column chromatography (n-hexane/AcOEt=2/1) to obtain 6-(benzofuran-2-yl)-3,5-dimethyl-4-methanesulfonyloxy-2H-pyran-2-one.

Yield: 46 mg (y. 88.2%) Yellow crystals.

$^1$H NMR($\delta$ ppm, CDCl$_3$): 2.22(s, 3H), 2.50(s, 3H), 3.39(s, 3H), 7.26 to 7.44(m, 3H), 7.54(d, J=8.2 Hz, 1H), 7.66(d, J=7.6 Hz, 1H)

Example 5

Synthesis of 6-(benzofuran-2-yl)-3,5-dimethyl-4-(2-pyridylcarboxy)-2H-pyran-2-one WSC (43 mg) was added to a solution of 6-(benzofuran-2-yl)-3,5-dimethyl-4-hydroxy-2H-pyran-2-one (40 mg), picolinic acid (23 mg) and HOBt (21 mg) in DMF (3 ml), and the mixture was stirred at room temperature for 21.5 hours. The reaction solution was concentrated under reduced pressure, and the residue was purified by silica gel column chromatography (n-hexane/AcOEt=2/1→3/2) to obtain 6-(benzofuran-2-yl)-3,5-dimethyl-4-(2-pyridylcarboxy)-2H-pyran-2-one.

Yield: 30 mg (y. 53.2%) Light yellow crystals.

$^1$H NMR($\delta$ ppm, CDCl$_3$): 2.07(s, 3H), 2.38(s, 3H), 7.25 to 7.42(m, 3H), 7.53(d, J=8.2 Hz, 1H), 7.61 to 7.69(m, 2H), 7.99(dd, J=1.6 Hz, 7.9 Hz, 1H), 8.32(d, J=7.9 Hz, 1H), 8.90(d, J=4.6 Hz, 1H)

Example 6

Synthesis of 3,5-dimethyl-4-hydroxy-6-(6-morpholinylbenzofuran-2-yl)-2H-pyran-2-one A solution of methyl 2-methyl-3-oxopentanoate (865 mg) in THF (30 ml) was slowly added to a suspension of NaH (240 mg) in THF (50 ml), and after stirring for 10 minutes, the mixture was cooled to −78° C. and 1.58 M n-BuLi (3.8 ml) was slowly added dropwise. After stirring the reaction solution at −78° C. for 30 minutes, a solution of methyl 6-morpholinylbenzofuran-2-carboxylate (1.3 g) in THF (15 ml) was slowly added and the mixture was stirred at −78° C. for 4 hours. A saturated ammonium chloride aqueous solution (30 ml) was added to the reaction solution, and after bringing it to room temperature, extraction was performed with AcOEt and the organic layer was dried with MgSO$_4$ and then filtered and concentrated. The residue was dissolved in MeOH (30 ml) and THF (30 ml), a 4 N lithium hydroxide aqueous solution (10 ml) was added, and after stirring at room temperature for 4 hours, a saturated KHSO$_4$ aqueous solution (50 ml) was slowly added. The deposited yellow precipitate was filtered off and rinsed with AcOEt to obtain 3,5-dimethyl-4-hydroxy-6-(6-morpholinylbenzofuran-2-yl)-2H-pyran-2-one.

Yield: 1.40 g (y. 82%)

$^1$H NMR($\delta$ ppm, DMSO-d6): 1.92(s, 3H), 2.26(s, 3H), 3.19(t, J=4.8 Hz, 4H), 3.75(t, J=4.8 Hz, 4H), 7.05(d, J=8.4 Hz, 1H), 7.16(s, 1H), 7.25(s, 1H), 7.54(d, J=8.4 Hz, 1H), 10.8(s, 1H)

Example 7

Synthesis of 3.5-dimethyl-6-(5-formylbenzofuran-2-yl)-4-hydroxy 2H-pyran-2-one

A solution of methyl 2-methyl-3-oxopentanoate (7.5 g) in THF (50 ml) was slowly added to a suspension of NaH (2.1 g) in THF (200 ml), and after stirring for 10 minutes, the mixture was cooled to −78° C. and 1.58 M n-BuLi (32 ml) was slowly added dropwise. After stirring the reaction solution at −78° C. for 30 minutes, a solution of methyl 5-(dimethoxymethyl)benzofuran-2-carboxylate (10 g) in THF (50 ml) was slowly added and the mixture was stirred at −78° C. for 4 hours. A saturated ammonium chloride aqueous solution (30 ml) was added to the reaction solution, and after bringing it to room temperature, extraction was performed with AcOEt and the organic layer was dried with MgSO$_4$ and then filtered and concentrated. The residue was dissolved in MeOH (100 ml) and THF (100 ml), a 4 N lithium hydroxide aqueous solution (25 ml) was added, and after stirring at room temperature for 4 hours, a saturated KHSO$_4$ aqueous solution (50 ml) was slowly added. The deposited yellow precipitate was filtered off and rinsed with AcOEt to obtain 3,5-dimethyl-6-(5-formylbenzofuran-2-yl)-4-hydroxy-2H-pyran-2-one Yield: 10.8 g (y. 95%)

$^1$H NMR($\delta$ ppm, DMSO-d6): 1.87(s, 3H), 2.23(s, 3H), 7.51(s, 1H), 7.78 to 7.92(m, 2H), 8.28(s, 1H), 10.0(s, 1H)

Example 8

Synthesis of 4-acetyloxy-3,5-dimethyl-6-(5-formylbenzofuran-2-yl)-2H-pyran-2-one After adding Et$_3$N (1.7 g) to a suspension of 3,5-dimethyl-6-(5-formylbenzofuran-2-yl)-4-hydroxy-2H-pyran-2-one (5.0 g) in CH$_2$Cl$_2$ (100 ml), the mixture was cooled on ice, acetyl chloride (1.32 g) was added and the mixture was stirred at room temperature for one hour. Water (100 ml) was added to the reaction solution, extraction was performed with AcOEt, and the organic layer was dried with MgSO$_4$ and then filtered and concentrated. The residue was purified by silica gel column chromatography (n-hexane/AcOEt=3/1) to obtain 4-acetyloxy-3,5-dimethyl-6-(5-formylbenzofuran-2-yl)-2H-pyran-2-one.

Yield: 5.1 g (y. 88%)

$^1$H NMR($\delta$ ppm, CDCl$_3$): 2.02(s, 3H), 2.32(s, 3H), 2.41(s, 3H), 7.46(s, 1H), 7.66(d, J=8.4 Hz, 1H), 7.96(d, J=8.4 Hz, 1H), 8.20(s, 1H), 10.1(s, 1H)

Example 9

Synthesis of 3,5-dimethyl-6-(5-((3,5-dioxo-2,4-thiazolidinylidene)methyl)benzofuran-2-yl)-4-hydroxy-2H-pyran-2-one Piperidine (100 mg) was added to a solution of 4-acetyloxy-3,5-dimethyl-6-(5-formylbenzofuran-2-yl)-2H-pyran-2-one (374 mg) and 1,3-thiazolidine-2,4-dione (135 mg) in THF (50 ml), and the mixture was subjected to heated reflux for 4 hours. After cooling, a 15% sodium hydroxide aqueous solution (10 ml) was added to the reaction solution, and then after stirring for one hour it was concentrated under reduced pressure. The residue was purified by silica gel column chromatography (CH$_2$Cl$_2$/MeOH=5/1) to obtain 3,5-dimethyl-6-(5-((3,5-dioxo-2,4-thiazolidinylidene)methyl)benzofuran-2-yl)-4-hydroxy-2H-pyran-2-one.

Yield: 400 mg (y. 91%)

$^1$H NMR($\delta$ ppm, DMSO-d6): 1.96(s, 3H), 2.22(s, 3H), 7.32(s, 1H), 7.45(d, J=8.4 Hz, 1H), 7.75(d, J=8.4 Hz, 1H), 8.12(s, 1H), 8.24(s, 1H), 10.91(s, 1H), 12.90(s, 1H)

Example 10

Synthesis of 3,5-dimethyl-6-(5-((3,5-dioxo-2,4-thiazolidinyl)methyl)benzofuran-2-yl)-4-hydroxy-2H-pyran-2-one To 3,5-dimethyl-6-(5-((3,5-dioxo-2,4-thiazolidinylidene)methyl)benzofuran-2-yl)-4-hydroxy-2H-pyran-2-one (350 mg) in a mixed solvent of EtOH (10 ml) and 1,4-dioxane (10 ml) there was added 10% Pd/C (70 mg), and the mixture was stirred for one day in a hydrogen gas atmosphere. The reaction solution was filtered, the mother liquor was concentrated under reduced pressure, and then the residue was purified by silica gel column chromatography (CH$_2$Cl$_2$/MeOH=5/1) to obtain 3,5-dimethyl-6-(5-((3,5-dioxo-2,4-thiazolidinyl)methyl)benzofuran-2-yl)-4-hydroxy-2H-pyran-2-one.

Yield: 352 mg (y. quant.)

$^1$H NMR($\delta$ ppm, DMSO-d6): 1.97(s, 3H), 2.24(s, 3H), 3.34 to 3.55(m, 1H), 3.67 to 3.82(m, 1H), 4.98 to 5.01(m, 1H), 7.24(s, 1H), 7.39(d, J=8.4 Hz, 1H), 7.61(d, J=8.4 Hz, 1H), 8.12(s, 1H), 10.93(s, 1H), 12.20(s, 1H)

Example 11

Synthesis of 6-(benzofuran-2-yl)-4-hydroxy-3-methyl-5-n-pentyl-2H-pyran-2-one

A solution of methyl 2-methyl-3-oxononanoate (3.06 g) in THF (5 ml) was added to a suspension of 60% NaH (608 mg) in THF (30 ml) while cooling on ice, and the mixture was stirred at 0° C. for 10 minutes and then at room temperature for 30 minutes. The reaction solution was cooled to −78° C., 1.66 M n-BuLi (9.2 ml) was added, and the mixture was stirred at −78° C. for 30 minutes to prepare a dienolate. A solution of methyl 2-benzofurancarboxylate (1.25 g) in THF (5 ml) was added to the dienolate, and the mixture was stirred at −78° C. for 30 minutes. The reaction solution was brought to 0° C., an NH$_4$Cl aqueous solution was added for quenching, and extraction was performed with AcOEt. The organic layer was rinsed with water and saturated saline in that order, and then dried with Na$_2$SO$_4$, filtered and concentrated. The residue was dissolved in MeOH (50 ml), and after adding 2N-LiOH (30 ml) and stirring at room temperature for 2 hours, 1N-HCl was added at 0° C. to acidity of approximately pH 3, and extraction was performed with AcOEt. The organic layer was rinsed with water and saturated saline in that order, and then dried with Na$_2$SO$_4$, filtered and concentrated. Pyridine (20 ml) and Ac$_2$O (20 ml) were added to the residue, and after stirring the mixture at room temperature for 5 hours it was concentrated under reduced pressure. The residue was dissolved in MeOH (20 ml), imidazole (483 mg) was added at 0° C., and after stirring the mixture at 0° C. for 10 minutes and then at room temperature for 30 minutes, it was concentrated under reduced pressure. AcOEt was added to the residue, and the precipitated crystals were filtered off. The crystals were recrystallized from EtOH to obtain 6-(benzofuran-2-yl)-4-hydroxy-3-methyl-5-n-pentyl-2H-pyran-2-one.

Yield: 357.9 mg (y. 16.1%)

$^1$H NMR($\delta$ ppm, DMSO-d6): 0.87(t, J=6.9 Hz, 3H), 1.28 to 1.60(m, 6H), 1.93(s, 3H), 2.74 to 2.85(m, 2H), 7.28 to 7.46(m, 3H), 7.63(d, J=8.3 Hz, 1H), 7.75(d, J=7.3 Hz, 1H), 10.86(brs, 1H)

Example 12

Synthesis of 3,5-dimethyl-4-hydroxy-6-(5-methoxybenzofuran-2-yl)-2H-pyran-2-one

K$_2$CO$_3$ (138 mg) was added to a solution of 5-methoxysalicyl aldehyde (152 mg) and 6-bromomethyl-3,5-dimethyl-4-methoxymethoxy-2H-pyran-2-one (277 mg) in DMF (5 ml), and the mixture was stirred at room temperature for 16 hours. A 6 N hydrochloric acid aqueous solution was slowly added to the reaction solution, and after stirring for one hour, extraction was performed with AcOEt and the organic layer was dried with MgSO$_4$ and then filtered and concentrated. The residue was purified by silica gel column chromatography (n-hexane/AcOEt=1/1) to obtain 3,5-dimethyl-4-hydroxy-6-(5-methoxybenzofuran-2-yl)-2H-pyran-2-one.

Yield: 229 mg (y. 80%)

$^1$H NMR($\delta$ ppm, CDCl$_3$): 2.01(s, 3H), 2.25(s, 3H), 4.00(s, 3H), 5.50 to 6.50(brs, 1H), 6.80 to 7.80(m, 4H)

Example 13

Synthesis of 3,5-dimethyl-4-hydroxy-6-(7-methoxybenzofuran-2-yl)-2H-pyran-2-one 3,5-dimethyl-4-hydroxy-6-(7-methoxybenzofuran-2-yl)-2H-pyran-2-one was obtained in the same manner as the preceding example.

Yield: 78%

$^1$H NMR($\delta$ ppm, CDCl$_3$): 2.10(s, 3H), 2.26(s, 3H), 4.00(s, 3H), 5.50 to 6.50(brs, 1H), 6.80 to 7.80(m, 4H)

Example 14

Synthesis of 6-(5-aminobenzofuran-2-yl)-3,5-dimethyl-4-methoxymethoxy-2H-pyran-2-one and 3,5-dimethyl-6-(5-(ethylamino)benzofuran-2-yl)-4-methoxymethoxy-2H-pyran-2-one To a solution of 3,5-dimethyl-4-methoxymethoxy-6-(5-nitrobenzofuran-2-yl)-2H-pyran-2-one (100 mg) in dioxane (20 ml) and EtOH (20 ml) there was added 5% Pd/C (5 mg), and after displacing the reaction vessel atmosphere with hydrogen, the mixture was stirred at room temperature overnight. The reaction solution was filtered and concentrated, and then purified by silica gel thin-layer chromatography (n-hexane/AcOEt=1/1) to obtain 6-(5-aminobenzofuran-2-yl)-3,5-dimethyl-4-methoxymethoxy-2H-pyran-2-one and 3,5-dimethyl-6-(5-(ethylamino)benzofuran-2-yl)-4-methoxymethoxy-2H-pyran-2-one.

6-(5-aminobenzofuran-2-yl)-3,5-dimethyl-4-methoxymethoxy-2H-pyran-2-one;

Yield: 45 mg (y. 49%)

$^1$H NMR($\delta$ ppm, CDCl$_3$): 2.12(s, 3H), 2.42(s, 3H), 3.64(s, 3H), 5.16(s, 2H), 6.83(dd, J=2.3 Hz, 8.9 Hz, 1H), 6.96(d, J=2.3 Hz, 1H), 7.20(s, 1H), 7.33(d, J=8.9 Hz, 1H), 7.42(s, 2H)

3,5-dimethyl-6-(5-(ethylamino)benzofuran-2-yl)-4-methoxymethoxy-2H-pyran-2-one;

Yield: 33 mg (y. 33%)

$^1$H NMR($\delta$ ppm, CDCl$_3$): 1.30(t, J=7.3 Hz, 3H), 2.11(s, 3H), 2.39(s, 3H), 3.19(q, J=7.3 Hz, 2H), 3.62(s, 3H), 5.11(s, 2H), 6.69(dd, J=2.3 Hz, 8.9 Hz, 1H), 6.75(d, J=2.3 Hz, 1H), 7.20(s, 1H), 7.31(d, J=8.9 Hz, 1H)

Example 15

Synthesis of 6-(5-(acetylamino)benzofuran-2-yl)-3,5-dimethyl-4-methoxymethoxy-2H-pyran-2-one Pyridine (400 μl) and Ac$_2$O (15 μl) were added to 6-(5-aminobenzofuran-2-yl)-3,5-dimethyl-4-methoxymethoxy-2H-pyran-2-one (45 mg), and after stirring the mixture at room temperature for 6 hours, an NH$_4$Cl aqueous solution was added and extraction was performed with CH$_2$Cl$_2$. The organic layer was dried, filtered and concentrated, and the residue was purified by silica gel thin-layer chromatography (CH$_2$Cl$_2$) to obtain 6-(5-acetylamino)benzofuran-2-yl)-3,5-dimethyl-4-methoxymethoxy-2H-pyran-2-one.

Yield: 20 mg (y. 39%)

$^1$H NMR($\delta$ ppm, CDCl$_3$): 2.10(s, 3H), 2.17(s, 3H), 2.43(s, 3H), 3.64(s, 3H), 5.20(s, 2H), 7.32(s, 1H), 7.45(d, J=8.9 Hz, 1H), 7.50(d, J=8.9 Hz, 1H), 7.97(d, J=0.7 Hz, 1H)

Example 16

Synthesis of 6-(5-aminobenzofuran-2-yl)-3,5-dimethyl-4-hydroxy-2H-pyran-2-one

THF (20 ml) was added to and stirred with 6-(5-aminobenzofuran-2-yl)-3,5-dimethyl-4-methoxymethoxy-2H-pyran-2-one (58 mg), one drop of concentrated hydrochloric acid was added and the mixture was stirred at room temperature for one hour. The reaction solution was concentrated under reduced pressure and the residue was purified by thin-layer chromatography (n-hexane/AcOEt =1/1) to obtain 6-(5-aminobenzofuran-2-yl)-3,5-dimethyl-4-hydroxy-2H-pyran-2-one.

Yield: 13 mg (y. 27%)

$^1$H NMR($\delta$ ppm, DMSO-d6): 1.93(s, 3H), 2.27(s, 3H), 6.71(dd, J=2.0 Hz, 8.9 Hz, 1H), 6.79(d, J=2.0 Hz, 1H), 7.16(s, 1H), 7.33(d, J=8.9 Hz, 1H)

Example 17

Synthesis of 6-(6-(benzyloxy)benzofuran-2-yl)-3,5-dimethyl-4-hydroxy-2H-pyran-2-one and 4-acetyloxy-6-(6-(benzyloxy)benzofuran-2-yl)-3,5-dimethyl-2H-pyran-2-one A solution of methyl 2-methyl-3-oxopentanoate (3.24 g) in THF (30 ml) was slowly added to a suspension of NaH (900 mg) in THF (50 ml) at 0° C., and after stirring for 10 minutes, the mixture was cooled to −78° C. and 1.58 M n-BuLi (14.2 ml) was slowly added dropwise. After stirring the reaction solution at −78° C. for 30 minutes, a solution of methyl 6-(benzyloxy)benzofuran-2-carboxylate (4.26 g) in THF (15 ml) was slowly added and the mixture was stirred at −78° C. for 4 hours. A saturated ammonium chloride aqueous solution was added to the reaction solution, and after bringing it to room temperature, extraction was performed with AcOEt and the organic layer was dried with MgSO$_4$ and then filtered and concentrated. The residue was dissolved in MeOH (30 ml) and THF (10 ml), a 4 N lithium hydroxide aqueous solution (5 ml) and water (50 ml) were added, and after stirring at room temperature for 4 hours, a saturated KHSO$_4$ aqueous solution (30 ml) was slowly added. The deposited yellow precipitate was filtered off and rinsed with AcOEt to obtain 6-(6-(benzyloxy)benzofuran-2-yl)-3,5-dimethyl-4-hydroxy-2H-pyran-2-one.

Yield: 964 mg (y. 25%)

$^1$H NMR($\delta$ ppm, DMSO-d6): 2.00(s, 3H), 2.24(s, 3H), 5.27(s, 2H), 7.11(d, J=8.4 Hz, 1H), 7.30 to 7.70(m, 8H), 10.8(brs, 1H)

The filtrate was further concentrated under reduced pressure, water (30 ml) and AcOEt (30 ml) were added, the organic layer and aqueous layer were separated, and the aqueous layer was extracted with AcOEt. The organic layers were combined, dried with MgSO$_4$, filtered and concentrated. Acetic anhydride (10 ml) and pyridine (3 ml) were added to the residue, and after stirring overnight, the reaction solution was concentrated under reduced pressure and purified by silica gel column chromatography (n-hexane/AcOEt=5/1→1/1) to obtain 4-acetyloxy-6-(6-(benzyloxy)benzofuran-2-yl)-3,5-dimethyl-2H-pyran-2-one.

Yield: 904 mg (y. 21%)

$^1$H NMR($\delta$ ppm, CDCl$_3$): 1.92(s, 3H), 1.97(s, 3H), 2.37(s, 3H), 5.09(s, 2H), 6.80 to 7.80(m, 9H)

Example 18

Synthesis of 4-acetyloxy-3,5-dimethyl-6-(6-hydroxybenzofuran-2-yl)-2H-pyran-2-one To a solution of 4-acetyloxy-6-(6-(benzyloxy)benzofuran-2-yl)-3,5-dimethyl-2H-pyran-2-one (500 mg) in EtOH (50 ml) and 1,4-dioxane (50 ml) there was added 10% Pd/C (100 mg), and the mixture was vigorously stirred at room temperature for 3 hours under a hydrogen gas atmosphere. The reaction solution was celite filtered, and then the filtrate was concentrated under reduced pressure and the residue was purified by silica gel column chromatography (n-hexane/AcOEt=1/1) to obtain 4-acetyloxy-3,5-dimethyl-6-(6-hydroxybenzofuran-2-yl)-2H-pyran-2-one.

Yield: 388 mg (y. 95%)

$^1$H NMR($\delta$ ppm, CDCl$_3$): 1.92(s, 3H), 1.97(s, 3H), 2.37(s, 3H), 5.50 to 6.50(brs, 1H), 6.80 to 7.80(m, 4H)

Example 19

Synthesis of 4-acetyloxy-3,5-dimethyl-6-(6-(trifluoromethanesulfonyloxy)benzofuran-2-yl)-2H-pyran-2-one Pyridine (100 mg) was added to a solution of 4-acetyloxy-3,5-dimethyl-6-(6-hydroxybenzofuran-2-yl)-2H-pyran-2-one (385 mg) in CH$_2$Cl$_2$ (10 ml), and after stirring at room temperature for one hour, trifluoromethanesulfonic anhydride (415 mg) was slowly added while cooling on ice and the mixture was stirred at room temperature for 2 hours. A saturated NaHCO$_3$ aqueous solution (10 ml) was added to the reaction solution, extraction was performed with AcOEt, and the organic layer was dried with Na$_2$SO$_4$ and then filtered and concentrated. The residue was purified by silica gel column chromatography (n-hexane/AcOEt=2/1) to obtain 4-acetyloxy-3,5-dimethyl-6-(6-(trifluoromethanesulfonyloxy) benzofuran-2-yl)-2H-pyran-2-one.

Yield: 392 mg (y. 72%)

Mass analysis: [M$^+$+H]=447.3

Example 20

Synthesis of 4-acetyloxy-3,5-dimethyl-6-(6-(methoxycarbonyl benzofuran-2-yl)-2H-pyran-2-one After adding a solution of 4-acetyloxy-3,5-dimethyl-6-(6-(trifluoromethanesulfonyloxy)benzofuran-2-yl)-2H-pyran-2-one (350 mg) in THF (5 ml) and Et$_3$N (80 mg) to a mixed solution of palladium acetate (3.5 mg) and diphenylphospinopropane (6.5 mg) in DMSO (5 ml) and MeOH (5 ml), the mixture was stirred at room temperature for one hour under a carbon monoxide atmosphere, and then further stirred at 80° C. for 2 hours. The reaction solution was concentrated under reduced pressure and the residue was purified by silica gel column chromatography (n-hexane/AcOEt=1/1) to obtain 4-acetyloxy-3,5-dimethyl-6-(6-(methoxycarbonyl) benzofuran-2-yl)-2H-pyran-2-one.

Yield: 92 mg (y. 33%)

Mass analysis: [M$^+$+H]=357.3

Example 21

Synthesis of 6-(6-carboxybenzofuran-2-yl)-3,5-dimethyl-4-hydroxy-2H-pyran-2-one

A mixed solution of 4-acetyloxy-3,5-dimethyl-6-(6-(methoxycarbonyl)benzofuran-2-yl)-2H-pyran-2-one (85 mg) and K$_2$CO$_3$ (45 mg) in MeOH (5 ml) and H$_2$O (1 ml) was stirred at room temperature for one hour, and then the reaction solution was rendered acidic with a 1 N hydrochloric acid aqueous solution and concentrated under reduced pressure. The residue was purified by silica gel column chromatography (AcOEt/MeOH=5/1) to obtain 6-(6-carboxybenzofuran-2-yl)-3,5-dimethyl-4-hydroxy-2H-pyran-2-one.

Yield: 71 mg (y. quant.)

Mass analysis: [M$^+$+H]=301.2

Example 22

Synthesis of 3,5-dimethyl-4-hydroxy-6-(6-(methoxycarbonyl)benzofuran-2-yl)-2H-pyran-2-one Trimethylsilyldiazomethane (2 M hexane solution, 85 $\mu$l) was added to a mixed solution of 6-(6-carboxybenzofuran-2-yl)-3,5-dimethyl-4-hydroxy-2H-pyran-2-one (50 mg) in MeOH (5 ml) and toluene (1 ml), and the mixture was stirred at room temperature for 10 minutes. After adding acetic acid to the reaction solution for quenching of the excess trimethylsilyldiazomethane, it was concentrated under reduced pressure. The residue was purified by silica gel column chromatography (CH$_2$Cl$_2$/MeOH =9/1) to obtain 3,5-dimethyl-4-hydroxy-6-(6-(methoxycarbonyl) benzofuran-2-yl)-2H-pyran-2-one.

Yield: 50 mg (y. 96%)

Mass analysis: [M$^+$+H]=315.3

Example 23

Synthesis of 4-acetyloxy-3,5-dimethyl-6-(6-dimethylaminobenzofuran-2-yl)-2H-pyran-2-one Tetrakis(triphenylphosphine)palladium (3 mg) and dimethylaminotrimethyltin (34 mg) were added to a solution of 4-acetyloxy-3,5-dimethyl-6-(6-(trifluoromethanesulfonyloxy) benzofuran-2-yl)-2H-pyran-2-one (45 mg) in toluene (5 ml), and the mixture was stirred at 50° C. overnight. After cooling, the reaction solution was concentrated under reduced pressure and the residue was purified by silica gel column chromatography (n-hexane/AcOEt=5/1) to obtain 4-acetyloxy-3,5-dimethyl-6-(6-dimethylaminobenzofuran-2-yl)-2H-pyran-2-one.

Yield: 9.6 mg (y. 28%)

Mass analysis: [M$^+$+H]=342.3

Example 24

Synthesis of 4-acetyloxy-3,5-dimethyl-6-(6-(2-furyl)benzofuran-2-yl)-2H-pyran-2-one 4-acetyloxy-3,5-dimethyl-6-(6-(2-furyl)benzofuran-2-yl)-2H-pyran-2-one was obtained in the same manner as the preceding example, using 2-(tributylstannyl)furan.

Yield: 31 mg (y. 87%)

Mass analysis: [M$^+$+H]=365.3

Example 25

Synthesis of 4-acetyloxy-3,5-dimethyl-6-(6-(2-thienyl)benzofuran-2-yl)-2H-pyran-2-one 4-acetyloxy-3,5-dimethyl-6-(6-(2-thienyl)benzofuran-2-yl)-2H-pyran-2-one was obtained in the same manner as the preceding example, using 2-(tributylstannyl)thiophene.

Yield: 31 mg (y. 85%)

Mass analysis: [M$^+$+H]=381.4

Example 26

Synthesis of 3,5-dimethyl-4-hydroxy-6-(6-methoxybenzofuran-2-yl)-2H-pyran-2-one

K$_2$CO$_3$ (1.38 g) was added to a solution of 4-methoxysalicyl aldehyde (1.52 g) and 6-bromo-3,5-dimethyl-4-methoxymethoxy-2H-pyran-2-one (2.77 g) in DMF (50 ml), and after stirring at room temperature overnight, the reaction solution was concentrated under reduced pressure. Water (50 ml) was added to the residue, extraction was performed with AcOEt, and the organic layer was dried with $MgSO_4$ and then filtered and concentrated. The residue was purified by silica gel column chromatography (n-hexane/AcOEt=1/1) to obtain 3.46 g of a yellow oil. Diisopropylethylamine (1.29 g) and DMF (20 ml) were added to 1.74 g of the yellow oil, prior to heated reflux overnight. After cooling, a 6 N hydrochloric acid aqueous solution (10 ml) was slowly added to the reaction solution, and the mixture was stirred at room temperature for one hour and then concentrated under reduced pressure. Water (50 ml) was added to the residue, extraction was performed with AcOEt, and the organic layer was dried with $MgSO_4$ and then filtered and concentrated. The residue was purified by silica gel column chromatography (n-hexane/AcOEt=1/1) to obtain 3,5-dimethyl-4-hydroxy-6-(6-methoxybenzofuran-2-yl)-2H-pyran-2-one.

Yield: 20 mg (y. 1.3%)

$^1$H NMR($\delta$ ppm, $CDCl_3$): 2.12(s, 3H), 2.27(s, 3H), 4.00(s, 3H), 5.50 to 6.50(brs, 1H), 6.80 to 7.80(m, 4H)

Example 27

Synthesis of 3,5-dimethyl-4-hydroxy-6-(5-(5-pyrimidinylmethoxy)benzofuran-2-yl)-2H-pyran-2-one A solution of tributylphosphine in 2 N THF (0.94 ml) and a solution of TMAD (323 mg) in $CH_2Cl_2$ (3 ml) were added dropwise to a solution of 4-acetyloxy-3,5-dimethyl-6-(5-hydroxybenzofuran-2-yl)-2H-pyran-2-one (118 mg) and 5-hydroxymethylpyrimidine (202 mg) in THF (30 ml) at 0° C., and the mixture was stirred at room temperature overnight. The reaction solution was cooled on ice, a 1 N lithium hydroxide aqueous solution (5 ml) was added and the mixture was stirred at room temperature for one hour, after which the reaction solution was again cooled on ice, a 1 N hydrochloric acid aqueous solution (5 ml) and AcOEt were added, the organic layer and aqueous layer were separated, and the aqueous layer was further extracted with AcOEt. The organic layers were combined and dried with $MgSO_4$, and then filtered and concentrated. The residue was purified by silica gel column chromatography (AcOEt/MeOH=10/1) to obtain 3,5-dimethyl-4-hydroxy-6-(5-(5-pyrimidinylmethoxy)benzofuran-2-yl)-2H-pyran-2-one.

Yield: 35 mg (y. 26%)

$^1$H NMR($\delta$ ppm, DMSO-d6): 1.95(s, 3H), 2.29(s, 3H), 5.24(s, 2H), 7.12 to 7.14(m, 1H), 7.33 to 7.38(m, 2H), 7.61 to 7.63(m, 1H), 8.95(s, 2H), 9.18(s, 1H), 10.91(brs, 1H)

The following compounds were produced by processes similar to those described in the preceding examples and production examples, using organic chemical techniques well-known to those skilled in the art.

Example 28

6-(benzofuran-2-yl)-3,5-dimethyl-4-(4-hydroxymethylbenzoyloxy)-2H-pyran-2-one $^1$H NMR($\delta$ ppm, $CDCl_3$): 2.04(s, 3H), 2.34(s, 3H), 4,86(s, 2H), 7.24 to 7.42(m, 3H), 7.53(d, J=8.2 Hz, 1H), 7.58(d, J=8.3 Hz, 1H), 7.66(d, J=7.9 Hz, 1H), 8.22(d, J=8.3 Hz, 1H)

Example 29

6-(benzofuran-2-yl)-4-(2-N-carbobenzyloxy -N-methylamino)acetyloxy)-3,5-dimethyl-2H-pyran-2-one $^1$H NMR($\delta$ ppm, $CDCl_3$): 1.84, 2.00(s, 3H), 2.14, 2.32(s, 3H), 3.13, 3.14(s, 3H), 4.33, 4.36(s, 2H), 5.18, 5.20(s, 2H), 7.25 to 7.43(m, 8H), 7.53(d, J=8.6 Hz, 1H), 7.66(d, J=6.9Hz, 1H)

Example 30

6-(benzofuran-2-yl)-3,5-dimethyl-4-(4-methoxybenzoyloxy)-2H-pyran-2-one $^1$H NMR($\delta$ ppm, $CDCl_3$): 2.03(s, 3H), 2.34(s, 3H), 3.93(s, 3H), 7.04(d, J=8.9 Hz, 2H), 7.24 to 7.42(m, 3H), 7.52(d, J=8.2 Hz, 1H), 7.66(d, J=7.9 Hz, 1H), 8.17(d, J=9.2 Hz, 1H)

Example 31

6-(benzofuran-2-yl)-3,5-dimethyl-4-phenylacetyloxy-2H-pyran-2-one $^1$H NMR($\delta$ ppm, $CDCl_3$): 1.86(s, 3H), 2.14(s, 3H), 3.93(s, 2H), 7.21 to 7.45(m, 8H), 7.50(d, J=7.9 Hz, 1H), 7.63(d, J=7.9 Hz, 1H)

Example 32

6-(benzofuran-2-yl)-4-hydroxy-3-methyl-2H -pyran-2-one $^1$H NMR($\delta$ ppm, DMSO-d6): 1.85(s, 3H), 6.73(s, 1H), 7.29 to 7.46(m, 3H), 7.67(d, J=7.9 Hz, 1H), 7.73(d, J=7.3 Hz, 1H), 11.58(brs, 1H)

Example 33

6-(benzofuran-2-yl)-5-ethyl-4-hydroxy-3-methyl-2H-pyran-2-one $^1$H NMR($\delta$ ppm, DMSO-d6): 1.18(t, J=7.3 Hz, 3H), 1.93(s, 3H), 2.79 (q, J=7.3 Hz, 2H), 7.29 to 7.44(m, 3H), 7.67 (d, J=8.3 Hz, 1H), 7.74(d, J=8.3 Hz, 1H), 10.89(brs, 1H)

Example 34

6-(benzofuran-2-yl)-4-hydroxy-5-isopropyl-3-methyl-2H-pyran-2-one $^1$H NMR($\delta$ ppm, DMSO-d6): 1.33(d, J=6.9 Hz, 6H), 1.93(s, 3H), 3.40 to 3.56(m, 1H), 7.29 to 7.46(m, 3H), 7.67(d, J=8.6 Hz, 1H), 7.74(d, J=7.6 Hz, 1H), 10.85(s, 1H)

Example 35

6-(benzofuran-2-yl)-4-hydroxy-3-methyl-5-phenyl-2H-pyran-2-one $^1$H NMR($\delta$ ppm, DMSO-d6): 2.06(s, 3H), 6.32(s, 1H), 7.27 to 7.63(m, 9H), 10.79(brs, 1H)

Example 36

6-(benzofuran-2-yl)-5-benzyl-4-hydroxy-3-methyl-2H-pyran-2-one $^1$H NMR($\delta$ ppm, DMSO-d6): 1.93(s, 3H), 4.23(s, 2H), 7.13 to 7.37(m, 8H), 7.62(d, J=8.3 Hz, 1H), 7.71(d, J=7.6 Hz, 1H), 11.01(brs, 1H)

Example 37

6-(benzofuran-2-yl)-4-hydroxy-5-methoxy-3-methyl-2H-pyran-2-one $^1$H NMR($\delta$ ppm, DMSO-d6): 1.92(s, 3H), 3.82(s, 3H), 7.32 to 7.51(m, 3H), 7.72(d, J=7.9 Hz, 1H), 7.78(d, J=7.3 Hz, 1H), 11.40(brs, 1H)

Example 38

6-(benzofuran-2-yl)-4-hydroxy-3-isopropyl-5-methyl-2H-pyran-2-one $^1$H NMR($\delta$ ppm, DMSO-d6): 1.22(d, J=6.9 Hz, 6H), 2.29(s, 3H), 3.20 to 3.30(m, 1H), 7.30 to 7.45(m, 3H), 7.68(d, J=7.9 Hz, 1H), 7.74(d, J=7.6 Hz, 1H), 10.68(s, 1H)

Example 39

6-(benzofuran-2-yl)-3,5-dimethyl-4-isobutyryloxy-2H-pyran-2-one

¹H NMR(δ ppm, CDCl₃): 1.39(d, J=6.9 Hz, 6H), 1.98(s, 3H), 2.29(s, 3H), 2.83 to 3.01(m, 1H), 7.25 to 7.42(m, 2H), 7.36(s, 1H), 7.52(d, J=8.3 Hz, 1H), 7.65(d, J=7.6 Hz, 1H)

Example 40

4-acetyloxy-3,5-dimethyl-6-(5-nitrobenzofuran-2-yl-2H-pyran-2-one

¹H NMR(δ ppm, CDCl₃): 2.02(s, 3H), 2.32(s, 3H), 2.42(s, 3H), 7.46(s, 1H), 7.64(d, J=8.9 Hz, 1H), 8.30(dd, J=2.3 Hz, 8.9 Hz, 1H), 8.59(d, J=2.3 Hz, 1H)

Example 41

3,5-dimethyl-4-methoxymethoxy-6-(5-nitrobenzofuran-2-yl -2H-pyran-2-one

¹H NMR(δ ppm, CDCl₃): 2.14(s, 3H), 2.43(s, 3H), 3.64(s, 3H), 5.14(s, 2H), 7.43(s, 1H), 7.63(d, J=9.0 Hz, 1H), 8.30(dd, J=2.1 Hz, 9.0 Hz, 1H), 8.58(d, J=2.1 Hz, 1H)

Example 42

6-(benzofuran-2-yl)-3,5-dimethyl-4-phenoxyacetyloxy-2H-pyran-2-one

¹H NMR(δ ppm, CDCl₃): 1.97(s, 3H), 2.28(s, 3H), 4.98(s, 2H), 6.95 to 7.12(m, 3H), 7.23 to 7.44(m, 5H), 7.52(d, J=7.9 Hz, 1H), 7.65(d, J=7.6 Hz, 1H)

Example 43

6-(benzofuran-2-yl)-3,5-dimethyl-4-trifluoromethanesulfonyloxy-2H-pyran-2-one

¹H NMR(δ ppm, CDCl₃): 2.23(s, 3H), 2.50(s, 3H), 7.28 to 7.46(m, 3H), 7.55(d, J=8.2 Hz, 1H), 7.68(d, J=7.6 Hz, 1H)

Example 44

6-(benzofuran-2-yl)-3,5-dimethyl-4-paratoluenesulfonyloxy-2H-pyran-2-one

¹H NMR(δ ppm, CDCl₃): 1.81(s, 3H), 2.33(s, 3H), 2.51(s, 3H), 7.28 to 7.48(m, 5H), 7.53(d, J=8.2 Hz, 1H), 7.66(d, J=7.6 Hz, 1H), 7.90(d, J=8.3 Hz, 2H)

Example 45

3,5-dimethyl-4-hydroxy-6-(5-nitrobenzofuran-2-yl)-2H-pyran-2-one

¹H NMR(δ ppm, CD3OD): 1.96(s, 3H), 2.32(s, 3H), 7.61(s, 1H), 7.95(d, J=9.2 Hz, 1H), 8.30(dd, J=2.3 Hz, 9.2 Hz, 1H), 8.71(d, J=2.3 Hz, 1H), 11.00(brs, 1H)

Example 46

3,5-dimethyl-6-(5-(ethylamino)benzofuran-2-yl)-4-hydroxy-2H-pyran-2-one

¹H NMR(δ ppm, CD3OD): 1.42(t, J=7.3 Hz, 3H), 2.04(s, 3H), 2.43(s, 3H), 3.44(q, J=7.3 Hz, 2H), 7.37(s, 1H), 7.50(dd, J=2.0 Hz, 8.9 Hz, 1H), 7.68(d, J=8.9 Hz, 1H), 7.79(d, J=2.0 Hz, 1H)

Example 47

3,5-dimethyl-4-hydroxy-6-(5-(p-touenesulfonylamino)benzofuran-2-yl)-2H-pyran-2-one ¹H NMR(δ ppm, CD3OD): 2.00(s, 3H), 2.36(s, 6H), 7.07 to 7.11(m, 1H), 7.21 to 7.26(m, 2H), 7.34 to 7.41(m, 2H), 7.57 to 7.61(m, 2H), 7.70 to 7.77(m, 1H)

Example 48

3,5-dimethyl-6-(5-(dimethylamino)benzofuran-2-yl)-4-hydroxy-2H-pyran-2-one

¹H NMR(δ ppm, CD3OD): 1.95(s, 3H), 2.30(s, 3H), 3.12(s, 6H), 7.41 to 7.75(m, 4H)

Example 49

6-(5-(dibenzylamino)benzofuran-2-yl)-3,5-dimethyl-4-hydroxy-2H-pyran-2-one

¹H NMR(δ ppm, CD3OD): 1.94(s, 3H), 2.31(s, 3H), 4.65(s, 4H), 6.89 to 6.94(m, 2H), 7.07(s, 1H), 7.13 to 7.88(m, 11H)

Example 50

6-(benzofuran-2-yl)-3,5-dimethyl-4-isonicotinoyloxy-2H-pyran-2-one

¹H NMR(δ ppm, CDCl₃): 2.04(s, 3H), 2.34(s, 3H), 7.26 to 7.42(m, 3H), 7.53(d, J=7.9 Hz, 1H), 7.67(d, J=7.3 Hz, 1H), 8.03, 8.95(ABq, J=6.3 Hz, 4H)

Example 51

4-(2-aminoacetyloxy-6-(benzofuran-2-yl)-3,5-dimethyl-2H-pyran-2-one hydrochloride ¹H NMR(δ ppm, DMSO-d6): 1.96(s, 3H), 2.27(s, 3H), 4.41(s, 2H), 7.31 to 7.50(m, 2H), 7.55(s, 1H), 7.71(d, J=8.3 Hz, 1H), 7.78(d, J=7.9 Hz, 1H), 8.61(brs, 3H)

Example 52

6-(5-benzyloxybenzofuran-2-yl)-4-(2-(t-butoxycarbonylamino)acetyloxy)-3,5-dimethyl-2H-pyran-2-one ¹H NMR(δppm, CDCl₃): 1.48(s, 9H), 2.00(s, 3H), 2.30(s, 3H), 4.23(d, J=5.9 Hz, 2H), 5.06 to 5.14(m, 1H), 5.11(s, 2H), 7.06(dd, J=2.6 Hz, 8.9 Hz, 1H), 7.14(d, J=2.6 Hz, 1H), 7.27 to 7.50(m, 7H)

Example 53

4-(2-aminoacetyloxy)-6-(5-benzyloxybenzofuran-2-yl)-3 5-dimethyl-2H-pyran-2-one hydrochloride ¹H NMR(δ ppm, DMSO-d6): 1.95(s, 3H), 2.24(s, 3H), 4.41(s, 2H), 5.16(s, 2H), 7.13(d, J=9.2 Hz, 1H), 7.29 to 7.51(m, 7H), 7.62(d, J=9.6 Hz, 1H), 8.57(brs, 2H)

Example 54

4-(4-(acetylamino)benzoyloxy)-6-(5-benzyloxybenzofuran-2-yl)-3,5-dimethyl-2H-pyran-2-one ¹H NMR(δ ppm, CDCl₃): 2.02(s, 3H), 2.26(s, 3H), 2.31(s, 3H), 5.12(s, 2H), 7.06(dd, J=2.6 Hz, 8.9 Hz, 1H), 7.15(d, J=2.6 Hz, 1H), 7.21 to 7.50(m, 8H), 7.72(d, J=8.9 Hz, 1H), 8.18(d, J=8.9 Hz, 1H)

Example 55

6-(5-benzyloxybenzofuran-2-yl)-3,5-dimethyl-4-nicotinoyloxy-2H-pyran-2-one

¹H NMR(δ ppm, CDCl₃): 2.04(s, 3H), 2.33(s, 3H), 5.12(s, 2H), 7.07(dd, J=2.6 Hz, 8.9 Hz, 1H), 7.16(d, J=2.6 Hz, 1H), 7.31 to 7.60(m, 8H), 8.48(d, J=7.9 Hz, 1H), 8.94(brs, 1H), 9.43(s, 1H)

Example 56

6-(5-benzyloxybenzofuran-2-yl)-3,5-dimethyl-4-isonicotinoyloxy-2H-pyran-2-one $^1$H NMR(δ ppm, CDCl$_3$): 2.03(s, 3H), 2.32(s, 3H), 5.12(s, 2H), 7.07(dd, J=2.3 Hz, 8.9 Hz, 1H), 7.16(d, J=2.3 Hz, 1H), 7.30 to 7.50(m, 7H), 8.03(d, J=5.9 Hz, 2H), 8.94(d, J=5.9 Hz, 2H)

Example 57

6-(5-benzyloxybenzofuran-2-yl)-5-ethyl-4-hydroxy-3-methyl-2H-pyran-2-one $^1$H NMR(δ ppm, DMSO-d6): 1.17(t, J=7.3 Hz, 3H), 1.93(s, 3H), 2.78(q, J=7.3 Hz, 2H), 5.14(s, 2H), 7.07(dd, J=2.6 Hz, 8.9 Hz, 1H), 7.29 to 7.48(m, 7H), 7.57(d, J=9.2 Hz, 1H), 10.87(brs, 1H)

Example 58

5-ethyl-4-hydroxy-3-methyl-6-(5-(3-pyrimidinylmethoxy)benzofuran-2-yl)-2H-pyran-2-one $^1$H NMR(δ ppm, DMSO-d6): 1.24(t, J=7.3 Hz, 3H), 1.99(s, 3H), 2.93(q, J=7.3 Hz, 2H), 5.20(s, 2H), 7.07 to 7.10(m, 1H), 7.27 to 7.28(m, 2H), 7.45 to 7.49(m, 2H), 7.97(d, J=7.6 Hz, 1H), 8.51(m, 1H), 8.67(s, 1H)

Example 59

4-acetyloxy-3,5-dimethyl-6-(5-(2-thiazolylmethoxy)benzofuran-2-yl)-2H-pyran-2-one $^1$H NMR(δ ppm, CDCl$_3$): 2.13(s, 3H), 2.34(s, 3H), 2.41(s, 3H), 5.30(s, 2H), 7.09(dd, J=8.6 Hz, 2,4 Hz, 1H), 7.32(s, 1H), 7.36(d, J=1.9 Hz, 1H), 7.47(d, J=1.9 Hz, 1H), 7.51(d, J=8.6 Hz, 1H), 7.86(d, J=2.4 Hz, 1H)

Example 60

4-hydroxy-3,5-dimethyl-6-(5-(2-thiazolylmethoxy)benzofuran-2-yl)-2H-pyran-2-one $^1$H NMR(δ ppm, CD3OD): 1.98(s, 3H), 2.29(s, 3H), 5.41(s, 2H), 6.87(dd, J=8.9 Hz, 2.4 Hz, 1H), 7.03(d, J=2.4 Hz, 1H), 7.48(d, J=8.9 Hz, 1H), 7.87(d, J=3.2 Hz, 1H), 7.91(d, J=3.2 Hz, 1H), 9.40(s, 1H)

Example 61

6-(benzofuran-2-yl)-3,5-dimethyl-4-(3-phenylpropionyloxy)-2H-pyran-2-one $^1$H NMR(δ ppm, CDCl$_3$): 1.86(s, 3H), 2.16(s, 3H), 2.94 to 3.18(m, 4H), 7.20 to 7.41(m, 8H), 7.52(d, J=7.9 Hz, 1H), 7.64(d, J=7.6 Hz, 1H)

Example 62

6-(benzofuran-2-yl)-3,5-dimethyl-4-(2-furoyloxy)-2H-pyran-2-one $^1$H NMR(δ ppm, CDCl$_3$): 2.04(s, 3H), 2.35(s, 3H), 6.67 (dd, J=1.7 Hz, 3.6 Hz, 1H), 7.25 to 7.42(m, 2H), 7.38(s, 1H), 7.50(d, J=3.6 Hz, 1H), 7.53(d, J=8.6 Hz, 1H), 7.66(d, J=7.6 Hz, 1H), 7.76(d, J=1.7 Hz, 1H)

Example 63

6-(benzofuran-2-yl)-3,5-dimethyl-4-nicotinoyloxy-2H-pyran-2-one $^1$H NMR(δ ppm, CDCl$_3$): 2.05(s, 3H), 2.36(s, 3H), 7.26 to 7.43(m, 3H), 7.50 to 7.60(m, 2H), 7.67(d, J=7.6 Hz, 1H), 8.49(d, J=7.9 Hz, 1H), 8.95(d, J=4.3 Hz, 1H), 9.44(s, 1H)

Example 64

6-(benzofuran-2-yl)-3,5-dimethyl-4-(2-acetylamino-4-(morpholin-4-yl)-4-oxobutyryloxy)-2H-pyran-2-one $^1$H NMR(δ ppm, CDCl$_3$): 2.01(s, 3H), 2.05(s, 3H), 2.33(s, 3H), 3.00(dd, J=4.4 Hz, 16.8 Hz, 1H), 3.16(dd, J=7.6 Hz, 16.8 Hz, 1H), 3.60 to 3.73(m, 8H), 5.37 to 5.44(m, 1H), 6.44(d, J=9.3 Hz, 1H), 7.27 to 7.40(m, 3H), 7.52(d, J=8.3 Hz, 1H), 7.65(d, J=7.3 Hz, 1H)

Example 65

4-acetyloxy-6-(5-bromobenzofuran-2-yl)-3,5-dimethyl-2H-pyran-2-one $^1$H NMR(δ ppm, CDCl$_3$): 2.00(s, 3H), 2.30(s, 3H), 2.40(s, 3H), 7.29(s, 1H), 7.40(d, J=8.9 Hz, 1H), 7.47(dd, J=8.9 Hz, 2.2 Hz, 1H), 7.78(d, J=2.2 Hz, 1H)

Example 66

6-(benzofuran-2-yl)-5-cyclopentylmethyl-4-hydroxy-3-methyl-2H-pyran-2-one $^1$H NMR(δ ppm, DMSO-d6): 1.16 to 1.27(m, 2H), 1.40 to 1.69(m, 6H), 1.94(s, 3H), 2.02 to 2.17(m, 1H), 2.90(d, J=7.3 Hz, 2H), 7.29 to 7.44(m, 3H), 7.65(d, J=8.2 Hz, 1H), 7.74(d, J=7.3 Hz, 1H), 10.85(s, 1H)

Example 67

6-(benzofuran-2-yl)-4-hydroxy-3-methyl-5-phenoxy-2H-pyran-2-one $^1$H NMR(δ ppm, DMSO-d6): 2.03(s, 3H), 7.11 to 7.22(m, 3H), 7.32 to 7.49(m, 5H), 7.69(d, J=8.3 Hz, 1H), 7.76(d, J=7.6 Hz, 1H), 11.56(brs, 1H)

Example 68

6-(benzofuran-2-yl)-5-(2-butenyl)-4-hydroxy-3-methyl-2H-pyran-2-one $^1$H NMR(δ ppm, DMSO-d6): 1.70 to 1.78(m, 3H), 2.03(s, 3H), 3.57 to 3.64(m, 2H), 5.61 to 5.67(m, 2H), 7.39 to 7.54(m, 3H), 7.78(d, J=8.3 Hz, 1H), 7.84(d, J=7.6 Hz, 1H), 11.00(brs, 1H)

Example 69

6-(benzofuran-2-yl)-4-(1-carbobenzyloxy-2-pyrrolidon-5-ylcarboxy)-3,5-dimethyl-2H-pyran-2-one $^1$H NMR(δ ppm, CDCl$_3$): 1.94(s, 3H), 2.25(s, 3H), 2.30 to 2.40(m, 1H), 2.51 to 2.88(m, 3H), 5.03(dd, J=2.6 Hz, 8.9 Hz, 1H), 5.33, 5.38(ABq, J=2.2 Hz, 2H), 7.28 to 7.48(m, 8H), 7.52(d, J=8.6 Hz, 1H), 7.66(d, J=7.9 Hz, 1H)

Example 70

6-(benzofuran-2-yl)-3,5-dimethyl-4-(2-pyrrolidon-5-ylcarboxy)-2H-pyran-2-one $^1$H NMR(δ ppm, DMSO-d6): 1.91(s, 3H), 2.23(s, 3H), 2.19 to 2.38(m, 3H), 2.47 to 2.66(m, 1H), 4.65 to 4.73(m, 1H), 7.31 to 7.40(m, 1H), 7.41 to 7.50(m, 1H), 7.53(s, 1H), 7.71(d, J=8.3 Hz, 1H), 7.77(d, J=7.6 Hz, 1H), 8.34(s, 1H)

Example 71

6-(benzofuran-2-yl)-4-(2-(t-butoxycarbonylamino)acetyloxy)-3,5-dimethyl-2H-pyran-2-one $^1$H NMR(δ ppm, CDCl$_3$): 1.48(s, 9H), 2.00(s, 3H), 2.32(s, 3H), 4.23(d, J=6.3 Hz, 2H), 5.10(brs, 1H), 7.25 to 7.42(m, 3H), 7.53(d, J=7.9 Hz, 1H), 7.65(d, J=7.9 Hz, 1H)

Example 72

6-(benzofuran-2-yl)-4-(2,4-dimethoxybenzoyloxy)-3,5-dimethyl-2H-pyran-2-one $^1$H NMR($\delta$ ppm, CDCl$_3$): 2.05(s, 3H), 2.35(s, 3H), 3.92(s, 3H), 3.95(s, 3H), 6.54 to 6.66(m, 2H), 7.25 to 7.41(m, 3H), 7.52(d, J=8.2 Hz, 1H), 7.65(d, J=7.6 Hz, 1H), 8.08(d, J=8.6 Hz, 1H)

Example 73

6-(benzofuran-2-yl)-4-(2,6-dimethoxybenzoyloxy)-3,5-dimethyl-2H-pyran-2-one $^1$H NMR($\delta$ ppm, CDCl$_3$): 2.17(s, 3H), 2.48(s, 3H), 3.91(s, 6H), 6.65(d, J=8.3 Hz, 2H), 7.25 to 7.45(m, 4H), 7.54(d, J=8.2 Hz, 1H), 7.66(d, J=7.9 Hz, 1H)

Example 74

6-(benzofuran-2-yl)-3,5-dimethyl-4-(6-hydroxynicotinoyloxy)-2H-pyran-2-one $^1$H NMR($\delta$ ppm, DMSO-d6): 1.91(s, 3H), 2.24(s, 3H), 6.48(d, J=9.9 Hz, 1H), 7.31 to 7.50(m, 2H), 7.54(s, 1H), 7.71(d, J=8.3 Hz, 1H), 7.78(d, J=7.9 Hz, 1H), 7.95(d, J=9.9 Hz, 1H), 8.43(s, 1H), 12.51(brs, 1H)

Example 75

6-(benzofuran-2-yl)-3,5-dimethyl-4-(3-dimethylaminobenzoyloxy)-2H-pyran-2-one $^1$H NMR($\delta$ ppm, CDCl$_3$): 2.04(s, 3H), 2.35(s, 3H), 3.05(s, 6H), 7.04(dd, J=2.6 Hz, 8.6 Hz, 1H), 7.25 to 7.44(m, 4H), 7.48 to 7.59(m, 3H), 7.66(d, J=7.6 Hz, 1H)

Example 76

4-(4-(acetylamino)benzoyloxy)-6-(benzofuran-2-yl)-3,5-dimethyl-2H-pyran-2-one $^1$H NMR($\delta$ ppm, CDCl$_3$): 2.03(s, 3H), 2.26(s, 3H), 2.33(s, 3H), 7.24 to 7.41(m, 3H), 7.49(s, 1H), 7.52(d, J=8.2 Hz, 1H), 7.66(d, J=7.6 Hz, 1H), 7.73(d, J=8.6 Hz, 2H), 8.18(d, J=8.6 Hz, 2H)

Example 77

3,5-dimethyl-6-(6-(2-fluorobenzyloxy)benzofuran-2-yl)-4-hydroxy-2H-pyran-2-one

Mass analysis: [M$^+$+H]=381.0

Example 78

3,5-dimethyl-6-(5-(2-fluorobenzyloxy)benzofuran-2-yl)-4-hydroxy-2H-pyran-2-one

Mass analysis: [M$^+$+H]=381.0

Example 79

6-(5-(4-chlorobenzyloxy)benzofuran-2-yl)-3,5-dimethyl-4-hydroxy-2H-pyran-2-one

Mass analysis: [M$^+$+H]=397.0

Example 80

6-(6-(2-bromobenzyloxy)benzofuran-2-yl)-3,5-dimethyl-4-hydroxy-2H-pyran-2-one

Mass analysis: [M$^+$+H]=442.0

Example 81

6-(5-(2-bromobenzyloxy)benzofuran-2-yl)-3,5-dimethyl-4-hydroxy-2H-pyran-2-one

Mass analysis: [M$^+$+H]=442.0

Example 82

6-(6-(3-bromobenzyloxy)benzofuran-2-yl)-3,5-dimethyl-4-hydroxy-2H-pyran-2-one

Mass analysis: [M$^+$+H]=442.0

Example 83

6-(5-(3-bromobenzyloxy)benzofuran-2-yl)-3,5-dimethyl-4-hydroxy-2H-pyran-2-one

Mass analysis: [M$^+$+H]=442.0

Example 84

3,5-dimethyl-4-hydroxy-6-(6-(3,4-(methylenedioxy)benzyloxy)benzofuran-2-yl -2H-pyran-2-one Mass analysis: [M$^+$+H]=407.0

Example 85

3,5-dimethyl-4-hydroxy-6-(5-(3,4-(methylenedioxy)benzyloxy)benzofuran-2-yl)-2H-pyran-2-one Mass analysis: [M$^+$+H]=407.0

Example 86

3,5-dimethyl-4-hydroxy-6-(6-(2-pyridylmethoxy)benzofuran-2-yl)-2H-pyran-2-one

Mass analysis: [M$^+$+H]=364.0

Example 87

3,5-dimethyl-4-hydroxy-6-(5-(2-pyridylmethoxy)benzofuran-2-yl)-2H-pyran-2-one

Mass analysis: [M$^+$+H]=364.0

Example 88

3,5-dimethyl-4-hydroxy-6-(6-(3-pyridylmethoxy)benzofuran-2-yl)-2H-pyran-2-one

Mass analysis: [M$^+$+H]=364.0

Example 89

3,5-dimethyl-4-hydroxy-6-(5-(3-pyridylmethoxy)benzofuran-2-yl)-2H-pyran-2-one

Mass analysis: [M$^+$+H]=364.0

Example 90

3,5-dimethyl-4-hydroxy-6-(6-(4-pyridylmethoxy)benzofuran-2-yl)-2H-pyran-2-one

Mass analysis: [M$^+$+H]=364.0

Example 91

3,5-dimethyl-4-hydroxy-6-(5-(4-pyridylmethoxy)benzofuran-2-yl)-2H-pyran-2-one

Mass analysis: [M$^+$+H]=364.0

Example 92

3,5-dimethyl-4-hydroxy-6-(6-(tetrahydrofuran-3-ylmethoxy)benzofuran-2-yl)-2H-pyran-2-one Mass analysis: [M$^+$+H]=357.0

Example 93

3,5-dimethyl-4-hydroxy-6-(5-(tetrahydrofuran-3-ylmethoxy)benzofuran-2-yl)-2H-pyran-2-one Mass analysis: [M$^+$+H]=357.0

Example 94

3,5-dimethyl-4-hydroxy-6-(6-(1-methylpiperidin-2-ylmethoxy)benzofuran-2-yl)-2H-pyran-2-one Mass analysis: [M$^+$+H]=384.0

Example 95

3,5-dimethyl-4-hydroxy-6-(5-(1-methylpiperidin-2-ylmethoxy)benzofuran-2-yl)-2H-pyran-2-one Mass analysis: [M$^+$+H]=384.0

Example 96

3,5-dimethyl-4-hydroxy-6-(6-(1-methylpiperidin-3-ylmethoxy)benzofuran-2-yl)-2H-pyran-2-one Mass analysis: [M$^+$+H]=384.0

Example 97

3,5-dimethyl-4-hydroxy-6-(5-(1-methylpiperidin-3-ylmethoxy)benzofuran-2-yl)-2H-pyran-2-one Mass analysis: [M$^+$+H]=384.0

Example 98

3,5-dimethyl-4-hydroxy-6-(6-(1-methyl-3-piperidinyloxy)benzofuran-2-yl)-2H-pyran-2-one Mass analysis: [M$^+$+H]=370.0

Example 99

3,5-dimethyl-4-hydroxy-6-(5-(1-methyl-3-piperidyloxy)benzofuran-2-yl)-2H-pyran-2-one Mass analysis: [M$^+$+H]=370.0

Example 100

3,5-dimethyl-4-hydroxy-6-(6-(1-methyl-3-pyrrolidyloxy)benzofuran-2-yl)-2H-pyran-2-one Mass analysis: [M$^+$+H]=356.0

Example 101

3,5-dimethyl-4-hydroxy-6-(5-(1-methyl-3-pyrrolidyloxy)benzofuran-2-yl)-2H-pyran-2-one Mass analysis: [M$^+$+H]=356.0

Example 102

3,5-dimethyl-4-hydroxy-6-(6-(2-pyrrolidinylethoxy)benzofuran-2-yl)-2H-pyran-2-one Mass analysis: [M$^+$+H]=370.0

Example 103

3,5-dimethyl-4-hydroxy-6-(5-(2-pyrrolidyloxy)benzofuran-2-yl)-2H-pyran-2-one

Mass analysis: [M$^+$+H]=370.0

Example 104

6-(6-(4-(diethylamino)-1-methylbutoxy)benzofuran-2-yl)-3,5-dimethyl-4-hydroxy-2H-pyran-2-one Mass analysis: [M$^+$+H]=414.0

Example 105

6-(5-(4-(diethylamino)-1-methylbutoxy)benzofuran-2-yl)-3,5-dimethyl-4-hydroxy-2H-pyran-2-one Mass analysis: [M$^+$+H]=414.0

Example 106

6-(6-(1,3-bis(dimethylamino)-2-propoxy)benzofuran-2-yl)-3,5-dimethyl-4-hydroxy-2H-pyran-2-one Mass analysis: [M$^+$+H]=401.0

Example 107

6-(5-(1,3-bis(dimethylamino)-2-propoxy)benzofuran-2-yl)-3,5-dimethyl-4-hydroxy-2H-pyran-2-one Mass analysis: [M$^+$+H]=401.0

Example 108

3,5-dimethyl-4-hydroxy-6-(6-(2-pyrrolidon-5-ylmethoxy)benzofuran-2-yl)-2H-pyran-2-one Mass analysis: [M$^+$+H]=370.0

Example 109

3,5-dimethyl-4-hydroxy-6-(5-(2-pyrrolidon-5-ylmethoxy)benzofuran-2-yl)-2H-pyran-2-one Mass analysis: [M$^+$+H]=370.0

Example 110

6-(6-(chroman-4-yloxy)benzofuran-2-yl)-3,5-dimethyl-4-hydroxy-2H-pyran-2-one

Mass analysis: [M$^+$+H]=405.0

Example 111

6-(5-(chroman-4-yloxy)benzofuran-2-yl)-3,5-dimethyl-4-hydroxy-2H-pyran-2-one

Mass analysis: [M$^+$+H]=405.0

Example 112

6-(6-(1-(n-butoxycarbonyl)ethoxy)benzofuran-2-yl)-3,5-dimethyl-4-hydroxy-2H-pyran-2-one Mass analysis: [M$^+$+H]=401.0

Example 113

6-(5-(1-(n-butoxycarbonyl)ethoxy)benzofuran-2-yl)-3,5-dimethyl-4-hydroxy-2H-pyran-2-one Mass analysis: [M$^+$+H]=401.0

Example 114

3,5-dimethyl-4-hydroxy-6-(6-(2-(morpholin-4-yl)ethoxy)benzofuran-2-yl)-2H-pyran-2-one Mass analysis: [M$^+$+H]=386.0

Example 115

3,5-dimethyl-4-hydroxy-6-(5-(2-(morpholin-4-yl)ethoxy)benzofuran-2-yl)-2H-pyran-2-one Mass analysis: [M$^+$+H]=386.0

Example 116

6-(6-(4-carboxybenzyloxy)benzofuran-2-yl)-3,5-dimethyl-4-hydroxy-2H-pyran-2-one

Mass analysis: [M$^+$+H]=407.0

Example 117

6-(5-(4-carboxybenzyloxy)benzofuran-2-yl)-3,5-dimethyl-4-hydroxy-2H-pyran-2-one

Mass analysis: [M$^+$+H]=407.0

Example 118

6-(6-(4-chlorobenzyloxy)benzofuran-2-yl)-3,5-dimethyl-4-hydroxy-2H-pyran-2-one

Mass analysis: [M$^+$+H]=397.0

Example 119

3,5-dimethyl-4-hydroxy-6-(6-(2-(trifluoromethyl)benzyloxy)benzofuran-2-yl)-2H-pyran-2-one Mass analysis: [M$^+$+H]=431.0

Example 120

3,5-dimethyl-4-hydroxy-6-(5-(2-(trifluoromethyl)benzyloxy)benzofuran-2-yl)-2H-pyran-2-one Mass analysis: [M$^+$+H]=431.0

Example 121

3,5-dimethyl-4-hydroxy-6-(6-(3-(trifluoromethyl)benzyloxy)benzofuran-2-yl)2H-pyran-2-one Mass analysis: [M$^+$+H]=431.0

Example 122

3,5-dimethyl-4-hydroxy-6-(5-(3-(trifluoromethyl)benzyloxy)benzofuran-2-yl)-2H-pyran-2-one Mass analysis: [M$^+$+H]=431.0

Example 123

3,5-dimethyl-4-hydroxy-6-(6-(4-(trifluoromethyl)benzyloxy)benzofuran-2-yl)-2H-pyran-2-one Mass analysis: [M$^+$+H]=431.0

Example 124

3,5-dimethyl-4-hydroxy-6-(5-(4-(trifluoromethyl)benzyloxy)benzofuran-2-yl)-2H-pyran-2-one Mass analysis: [M$^+$+H]=431.0

Example 125

6-(6-(cyclopentylmethoxy)benzofuran-2-yl)-3,5-dimethyl-4-hydroxy-2H-pyran-2-one

Mass analysis: [M$^+$+H]=355.0

Example 126

6-(5-(cyclopentylmethoxy)benzofuran-2-yl)-3,5-dimethyl-4-hydroxy-2H-pyran-2-one

Mass analysis: [M$^+$+H]=355.0

Example 127

6-(6-(cyclopropylmethoxy)benzofuran-2-yl)-3,5-dimethyl-4-hydroxy-2H-pyran-2-one

Mass analysis: [M$^+$+H]=327.0

Example 128

6-(5-(cyclopropylmethoxy)benzofuran-2-yl)-3,5-dimethyl-4-hydroxy-2H-pyran-2-one

Mass analysis: [M$^+$+H]=327.0

Example 129

6-(6-(2,4-dimethylbenzyloxy)benzofuran-2-yl)-3,5-dimethyl-4-hydroxy-2H-pyran-2-one Mass analysis: [M$^+$+H]=391.0

Example 130

6-(5-(2,4-dimethylbenzyloxy)benzofuran-2-yl)-3,5-dimethyl-4-hydroxy-2H-pyran-2-one Mass analysis: [M$^+$+H]=391.0

Example 131

6-(6-(2,5-dimethylbenzyloxy)benzofuran-2-yl)-3,5-dimethyl-4-hydroxy-2H-pyran-2-one Mass analysis: [M$^+$+H]=391.0

Example 132

6-(5-(2,5-dimethylbenzyloxy)benzofuran-2-yl)-3,5-dimethyl-4-hydroxy-2H-pyran-2-one Mass analysis: [M$^+$+H]=391.0

Example 133

6-(6-(3,4-dimethylbenzyloxy)benzofuran-2-yl)-3,5-dimethyl-4-hydroxy-2H-pyran-2-one Mass analysis: [M$^+$+H]=391.0

Example 134

6-(5-(3,4-dimethylbenzyloxy)benzofuran-2-yl)-3,5-dimethyl-4-hydroxy-2H-pyran-2-one Mass analysis: [M$^+$+H]=391.0

Example 135

6-(6-(3,5-dimethylbenzyloxy)benzofuran-2-yl)-3,5-dimethyl-4-hydroxy-2H-pyran-2-one Mass analysis: [M$^+$+H]=391.0

Example 136

6-(5-(3,5-dimethylbenzyloxy)benzofuran-2-yl)-3,5-dimethyl-4-hydroxy-2H-pyran-2-one Mass analysis: $[M^++H]=391.0$

Example 137

3,5-dimethyl-4-hydroxy-6-(6-((2-thienyl)methoxy)benzofuran-2-yl)-2H-pyran-2-one

Mass analysis: $[M^++H]=369.0$

Example 138

3,5-dimethyl-4-hydroxy-6-(5-((2-thienyl)methoxy)benzofuran-2-yl)-2H-pyran-2-one

Mass analysis: $[M^++H]=369.0$

Example 139

3,5-dimethyl-6-(6-((2-furyl)methoxy)benzofuran-2-yl)-4-hydroxy-2H-pyran-2-one

Mass analysis: $[M^++H]=353.0$

Example 140

3,5-dimethyl-6-(5-((2-furyl)methoxy)benzofuran-2-yl)-4-hydroxy-2H-pyran-2-one

Mass analysis: $[M^++H]=353.0$

Example 141

3,5-dimethyl-4-hydroxy-6-(6-(2-phenoxyethoxy)benzofuran-2-yl)-2H-pyran-2-one

Mass analysis: $[M^++H]=392.0$

Example 142

3,5-dimethyl-4-hydroxy-6-(5-(2-phenoxyethoxy)benzofuran-2-yl)-2H-pyran-2-one

Mass analysis: $[M^++H]=392.0$

Example 143

3,5-dimethyl-4-hydroxy-6-(6-(1-(2-(trifluoromethyl)phenyl)ethoxy)benzofuran-2-yl)-2H-pyran-2-one Mass analysis: $[M^++H]=445.0$

Example 144

3,5-dimethyl-4-hydroxy-6-(5-(1-(2-(trifluoromethyl)phenyl)ethoxy)benzofuran-2-yl)-2H-pyran-2-one Mass analysis: $[M^++H]=445.0$

Example 145

6-(6-(2-chloro-5-nitrobenzyloxy)benzofuran-2-yl)-3,5-dimethyl-4-hydroxy-2H-pyran-2-one Mass analysis: $[M^++H]=442.0$

Example 146

6-(6-(3-chloro-6-nitrobenzyloxy)benzofuran-2-yl)-3,5-dimethyl-4-hydroxy-2H-pyran-2-one Mass analysis: $[M^++H]=442.0$

Example 147

6-(5-(3-chloro-6-nitrobenzyloxy)benzofuran-2-yl)-3,5-dimethyl-4-hydroxy-2H-pyran-2-one Mass analysis: $[M^++H]=442.0$

Example 148

6-(6-(2-cyclohexylethoxy)benzofuran-2-yl)-3,5-dimethyl-4-hydroxy-2H-pyran-2-one

Mass analysis: $[M^++H]=383.0$

Example 149

6-(5-(2-cyclohexylethoxy)benzofuran-2-yl)-3,5-dimethyl-4-hydroxy-2H-pyran-2-one

Mass analysis: $[M^++H]=383.0$

Example 150

3,5-dimethyl-4-hydroxy-6-(6-(1,4-pentadien-3-yloxy)benzofuran-2-yl)-2H-pyran-one Mass analysis: $[M^++H]=339.0$

Example 151

3,5-dimethyl-4-hydroxy-6-(5-(1,4-pentadien-3-yloxy)benzofuran-2-yl )-2H-pyran-2-one Mass analysis: $[M^++H]=339.0$

Example 152

6-(6-(2,4-dichlorobenzyloxy)benzofuran-2-yl)-3,5-dimethyl-4-hydroxy-2H-pyran-2-one Mass analysis: $[M^++H]=432.0$

Example 153

6-(5-(2,4-dichlorobenzyloxy)benzofuran-2-yl)-3,5-dimethyl-4-hydroxy-2H-pyran-2-one Mass analysis: $[M^++H]=432.0$

Example 154

6-(6-(2,5-dichlorobenzyloxy)benzofuran-2-yl)-3,5-dimethyl-4-hydroxy-2H-pyran-2-one Mass analysis: $[M^++H]=432.0$

Example 155

6-(5-(2,5-dichlorobenzyloxy)benzofuran-2-yl)-3,5-dimethyl-4-hydroxy-2H-pyran-2-one Mass analysis: $[M^++H]=432.0$

Example 156

6-(6-(2,6-dichlorobenzyloxy)benzofuran-2-yl)-3,5-dimethyl-4-hydroxy-2H-pyran-2-one Mass analysis: $[M^++H]=432.0$

Example 157

6-(5-(2,6-dichlorobenzyloxy)benzofuran-2-yl)-3,5-dimethyl-4-hydroxy-2H-pyran-2-one Mass analysis: $[M^++H]=432.0$

Example 158

6-(6-(3,4-dichlorobenzyloxy)benzofuran-2-yl)-3,5-dimethyl-4-hydroxy-2H-pyran-2-one Mass analysis: $[M^++H]=432.0$

Example 159

6-(5-(3,4-dichlorobenzyloxy)benzofuran-2-yl)-3,5-dimethyl-4-hydroxy-2H-pyran-2-one Mass analysis: $[M^++H]=432.0$

Example 160

6-(6-(3,5-dichlorobenzyloxy)benzofuran-2-yl)-3,5-dimethyl-4-hydroxy-2H-pyran-2-one Mass analysis: $[M^++H]=432.0$

Example 161

6-(5-(3,5-dichlorobenzyloxy)benzofuran-2-yl)-3,5-dimethyl-4-hydroxy-2H-pyran-2-one Mass analysis: $[M^++H]=432.0$

Example 162

6-(6-(4-n-butoxybenzyloxy)benzofuran-2-yl)-3,5-dimethyl-4-hydroxy-2H-pyran-2-one Mass analysis: $[M^++H]=435.0$

Example 163

6-(5-(4-n-butoxybenzyloxy)benzofuran-2-yl)-3,5-dimethyl-4-hydroxy-2H-pyran-2-one Mass analysis: $[M^++H]=435.0$

Example 164

3,5-dimethyl-4-hydroxy-6-(6-(3-methyl-2-nitrobenzyloxy)benzofuran-2-yl)-2H-pyran-2-one Mass analysis: $[M^++H]=422.0$

Example 165

3,5-dimethyl-4-hydroxy-6-(5-(3-methyl-2-nitrobenzyloxy)benzofuran-2-yl)-2H-pyran-2-one Mass analysis: $[M^++H]=422.0$

Example 166

3,5-dimethyl-6-(6-(2,3-dimethyl-4-methoxybenzyloxy)benzofuran-2-yl)-4-hydroxy-2H-pyran-2-one Mass analysis: $[M^++H]=421.0$

Example 167

3,5-dimethyl-6-(5-(2,3-dimethyl-4-methoxybenzyloxy)benzofuran-2-yl)-4-hydroxy-2H-pyran-2-one Mass analysis: $[M^++H]=421.0$

Example 168

3,5-dimethyl-6-(6-(3,5-dinitrobenzyloxy)benzofuran-2-yl)-4-hydroxy-2H-pyran-2-one Mass analysis: $[M^++H]=453.0$

Example 169

3,5-dimethyl-6-(5-(3,5-dinitrobenzyloxy)benzofuran-2-yl)-4-hydroxy-2H-pyran-2-one Mass analysis: $[M^++H]=453.0$

Example 170

3,5-dimethyl-4-hydroxy-6-(6-(1,2,3,4-tetrahydronaphthalen-1-yloxy)benzofuran-2-yl)-2H-pyran-2-one Mass analysis: $[M^++H]=403.0$

Example 171

3,5-dimethyl-4-hydroxy-6-(5-(1,2,3,4-tetrahydronaphthalen-1-yloxy)benzofuran-2-yl)-2H-pyran-2-one Mass analysis: $[M^{+-}+H]=403.0$

Example 172

3,5-dimethyl-4-hydroxy-6-(6-(1-naphthylmethoxy)benzofuran-2-yl)-2H-pyran-2-one

Mass analysis: $[M^++H]=413.0$

Example 173

3,5-dimethyl-4-hydroxy-6-(5-(1-naphthylmethoxy)benzofuran-2-yl)-2H-pyran-2-one

Mass analysis: $[M^++H]=413.0$

Example 174

3,5-dimethyl-4-hydroxy-6-(6-(2-naphthylmethoxy)benzofuran-2-yl -2H-pyran-2-one

Mass analysis: $[M^++H]=413.0$

Example 175

3,5-dimethyl-4-hydroxy-6-(5-(2-naphthylmethoxy)benzofuran-2-yl)-2H-pyran-2-one

Mass analysis: $[M^++H]=413.0$

Example 176

6-(6-(1,4-benzodioxan-2-ylmethoxy)benzofuran-2-yl)-3,5-dimethyl-4-hydroxy-2H-pyran-2-one Mass analysis: $[M^++H]=421.0$

Example 177

6-(5-(1,4-benzodioxan-2-ylmethoxy)benzofuran-2-yl)-3,5-dimethyl-4-hydroxy-2H-pyran-2-one Mass analysis: $[M^++H]=421.0$

Example 178

3,5-dimethyl-6-(6-(3-hexen-1-yloxy)benzofuran-2-yl)-4-hydroxy-2H-pyran-2-one

Mass analysis: $[M^++H]=355.0$

Example 179

3,5-dimethyl-6-(5-(3-hexen-1-yloxy)benzofuran-2-yl)-4-hydroxy-2H-pyran-2-one

Mass analysis: $[M^++H]=355.0$

Example 180

6-(6-(2-butyn-1-yloxy)benzofuran-2-yl)-3,5-dimethyl-4-hydroxy-2H-pyran-2-one

Mass analysis: [M$^+$+H]=325.0

Example 181

6-(5-(2-butyn-1-yloxy)benzofuran-2-yl)-3,5-dimethyl-4-hydroxy-2H-pyran-2-one

Mass analysis: [M$^+$+H]=325.0

Example 182

3,5-dimethyl-6-(6-(2,2-dimethyl-1,3-dioxolan-4-ylmethoxy)benzofuran-2-yl)-4-hydroxy-2H-pyran-2-one Mass analysis: [M$^+$+H]=387.0

Example 183

3,5-dimethyl-6-(5-(2,2-dimethyl-1,3-dioxolan-4-ylmethoxy)benzofuran-2-yl)-4-hydroxy-2H-pyran-2-one Mass analysis: [M$^+$+H]=387.0

Example 184

3,5-dimethyl-6-(6-(2-ethoxyethoxy)benzofuran-2-yl)-4-hydroxy-2H-pyran-2-one

Mass analysis: [M$^+$+H]=345.0

Example 185

3,5-dimethyl-6-(5-(2-ethoxyethoxy)benzofuran-2-yl)-4-hydroxy-2H-pyran-2-one

Mass analysis: [M$^+$+H]=345.0

Example 186

3,5-dimethyl-4-hydroxy-6-(6-(3-methyloxetan-3-ylmethoxy)benzofuran-2-yl)-2H-pyran-2-one Mass analysis: [M$^+$+H]=357.0

Example 187

3,5-dimethyl-4-hydroxy-6-(5-(3-methyloxetan-3-ylmethoxy)benzofuran-2-yl)-2H-pyran-2-one Mass analysis: [M$^+$+H]=357.0

Example 188

3,5-dimethyl-6-(6-(5-hexyn-1-yloxy)benzofuran-2-yl)-4-hydroxy-2H-pyran-2-one

Mass analysis: [M$^+$+H]=353.0

Example 189

3,5-dimethyl-6-(5-(5-hexyn-1-yloxy)benzofuran-2-yl)-4-hydroxy-2H-pyran-2-one

Mass analysis: [M$^+$+H]=353.0

Example 190

3,5-dimethyl-6-(6-(5-hexen-1-yloxy)benzofuran-2-yl)-4-hydroxy-2H-pyran-2-one

Mass analysis: [M$^+$+H]=355.0

Example 191

3,5-dimethyl-6-(5-(5-hexen-1-yloxy)benzofuran-2-yl)-4-hydroxy-2H-pyran-2-one

Mass analysis: [M$^+$+H]=355.0

Example 192

3,5-dimethyl-6-(6-(2,2-dimethylpropoxy)benzofuran-2-yl)-4-hydroxy-2H-pyran-2-one Mass analysis: [M$^+$+H]=343.0

Example 193

3,5-dimethyl-6-(5-(2,2-dimethylpropoxy)benzofuran-2-yl -4-hydroxy-2H-pyran-2-one Mass analysis: [M$^+$+H]=343.0

Example 194

3,5-dimethyl-6-(6-(2,2-diphenylethoxy)benzofuran-2-yl)-4-hydroxy-2H-pyran-2-one

Mass analysis: [M$^+$+H]=453.0

Example 195

3,5-dimethyl-6-(5-(2,2-diphenylethoxy)benzofuran-2-yl)-4-hydroxy-2H-pyran-2-one

Mass analysis: [M$^+$+H]=453.0

Example 196

3,5-dimethyl-4-hydroxy-6-(6-(2-phenyl-2-propoxy)benzofuran-2-yl)-2H-pyran-2-one

Mass analysis: [M$^+$+H]=391.0

Example 197

3,5-dimethyl-4-hydroxy-6-(5-(2-phenyl-2-propoxy)benzofuran-2-yl -2H-pyran-2-one

Mass analysis: [M$^+$+H]=391.0

Example 198

3,5-dimethyl-4-hydroxy-6-(6-(2-(1-naphthyl)ethoxy)benzofuran-2-yl)-2H-pyran-2-one Mass analysis: [M$^+$+H]=427.0

Example 199

3,5-dimethyl-4-hydroxy-6-(5-(2-(1-naphtyl)ethoxy)benzofuran-2-yl)-2H-pyran-2-one Mass analysis: [M$^+$+H]=427.0

Example 200

6-(6-(bis(4-methoxyphenyl)methoxy)benzofuran-2-yl)-3,5-dimethyl-4-hydroxy-2H-pyran-2-one Mass analysis: [M$^+$+H]=499.0

Example 201

6-(5-(bis(4-methoxyphenyl)methoxy)benzofuran-2-yl)-3,5-dimethyl-4-hydroxy-2H-pyran-2-one Mass analysis: [M$^+$+H]=499.0

Example 202

3,5-dimethyl-4-hydroxy-6-(6-(3-phenylpropoxy)benzofuran-2-yl)-2H-pyran-2-one

Mass analysis: [M$^+$+H]=391.0

Example 203

3,5-dimethyl-4-hydroxy-6-(5-(3-phenylpropoxy)benzofuran-2-yl)-2H-pyran-2-one

Mass analysis: [M$^+$+H]=391.0

Example 204

3,5-dimethyl-4-hydroxy-6-(6-(4-phenylbutoxy)benzofuran-2-yl)-2H-pyran-2-one

Mass analysis: [M$^+$+H]=405.0

Example 205

3,5-dimethyl-4-hydroxy-6-(5-(4-phenylbutoxy)benzofuran-2-yl)-2H-pyran-2-one

Mass analysis: [M$^+$+H]=405.0

Example 206

6-(6-(cyclohexylmethoxy)benzofuran-2-yl)-3,5-dimethyl-4-hydroxy-2H-pyran-2-one

Mass analysis: [M$^+$+H]=369.0

Example 207

6-(5-(cyclohexylmethoxy)benzofuran-2-yl)-3,5-dimethyl-4-hydroxy-2H-pyran-2-one

Mass analysis: [M$^+$+H]=369.0

Example 208

6-(6-(3-cyclohexylpropoxy)benzofuran-2-yl)-3,5-dimethyl-4-hydroxy-2H-pyran-2-one Mass analysis: [M$^+$+H]=397.0

Example 209

6-(5-(3-cyclohexylpropoxy)benzofuran-2-yl)-3,5-dimethyl-4-hydroxy-2H-pyran-2-one Mass analysis: [M$^+$+H]=397.0

Example 210

6-(6-(3-buten-1-yloxy)benzofuran-2-yl)-3,5-dimethyl-4-hydroxy-2H-pyran-2-one

Mass analysis: [M$^+$+H]=327.0

Example 211

6-(5-(3-buten-1-yloxy)benzofuran-2-yl)-3,5-dimethyl-4-hydroxy-2H-pyran-2-one

Mass analysis: [M$^+$+H]=327.0

Example 212

6-(6-(2-(benzyloxy)ethoxy)benzofuran-2-yl)-3,5-dimethyl-4-hydroxy-2H-pyran-2-one Mass analysis: [M$^+$+H]=407.0

Example 213

6-(5-(2-(benzyloxy)ethoxy)benzofuran-2-yl)-3,5-dimethyl-4-hydroxy-2H-pyran-2-one Mass analysis: [M$^+$+H]=407.0

Example 214

3,5-dimethyl-4-hydroxy-6-(6-(2-propyn-1-yloxy)benzofuran-2-yl)-2H-pyran-2-one

Mass analysis: [M$^+$+H]=311.0

Example 215

3,5-dimethyl-4-hydroxy-6-(5-(2-propyn-1-yloxy)benzofuran-2-yl)-2H-pyran-2-one

Mass analysis: [M$^+$+H]=311.0

Example 216

3,5-dimethyl-6-(6-(5-(ethoxycarbonyl)pentyloxy)benzofuran-2-yl)-4-hydroxy-2H-pyran-2-one Mass analysis: [M$^+$+H]=415.0

Example 217

3,5-dimethyl-6-(5-(5-(ethoxycarbonyl)pentyloxy)benzofuran-2-yl)-4-hydroxy-2H-pyran-2-one Mass analysis: [M$^+$+H]=415.0

Example 218

3,5-dimethyl-6-(6-ethoxybenzofuran-2-yl)-4-hydroxy-2H-pyran-2-one

Mass analysis: [M$^+$+H]=301.0

Example 219

3,5-dimethyl-4-hydroxy-6-(6-isopropoxybenzofuran-2-yl)-2H-pyran-2-one

Mass analysis: [M$^+$+H]=329.0

Example 220

6-(5-(1-t-butoxycarbonylpiperidin-2-ylmethoxy)benzofuran-2-yl)-3,5-dimethyl-4-hydroxy-2H-pyran-2-one Mass analysis: [M$^+$+H]=470.0

Example 221

6-(5-(1-t-butoxycarbonylpiperidin-4-ylmethoxy)benzofuran-2-yl)-3,5-dimethyl-4-hydroxy-2H-pyran-2-one Mass analysis: [M$^+$+H]=470.0

Example 222

6-(5-(1-t-butoxycarbonylpiperidin-4-yloxy)benzofuran-2-yl)-3,5-dimethyl-4-hydroxy-2H-pyran-2-one Mass analysis: [M$^+$+H]=456.0

Example 223

6-(5-(1-t-butoxycarbonylpyrrolidin-3-yloxy)benzofuran-2-yl)-3,5-dimethyl-4-hydroxy-2H-pyran-2-one Mass analysis: [M$^+$+H]=442.0

Example 224

6-(5-(4-(t-butoxycarbonylamino)butoxy)benzofuran-2-yl)-3,5-dimethyl-4-hydroxy-2H-pyran-2-one Mass analysis: [M++H]=444.0

Example 225

3,5-dimethyl-6-(6-(3-fluorobenzyloxy)benzofuran-2-yl )-4-hydroxy-2H-pyran-2-one

Mass analysis: [M++H]=381.0

Example 226

3,5-dimethyl-6-(5-(3-fluorobenzyloxy)benzofuran-2-yl)-4-hydroxy-2H-pyran-2-one

Mass analysis: [M++H]=381.0

Example 227

3,5-dimethyl-6-(6-(4-fluorobenzyloxy)benzofuran-2-yl)-4-hydroxy-2H-pyran-2-one

Mass analysis: [M++H]=381.0

Example 228

3,5-dimethyl-6-(5-(4-fluorobenzyloxy)benzofuran-2-yl)-4-hydroxy-2H-pyran-2-one

Mass analysis: [M+⁻+H]=381.0

Example 229

3,5-dimethyl-4-hydroxy-6-(6-(2-nitrobenzyloxy)benzofuran-2-yl)-2H-pyran-2-one

Mass analysis: [M++H]=408.0

Example 230

3,5-dimethyl-4-hydroxy-6-(5-(2-nitrobenzyloxy)benzofuran-2-yl)-2H-pyran-2-one

Mass analysis: [M++H]=408.0

Example 231

3,5-dimethyl-4-hydroxy-6-(6-(3-nitrobenzyloxy)benzofuran-2-yl)-2H-pyran-2-one

Mass analysis: [M++H]=408.0

Example 232

3,5-dimethyl-4-hydroxy-6-(5-(3-nitrobenzyloxy)benzofuran-2-yl)-2H-pyran-2-one

Mass analysis: [M++H]=408.0

Example 233

3,5-dimethyl-4-hydroxy-6-(6-(4-nitrobenzyloxy)benzofuran-2-yl)-2H-pyran-2-one

Mass analysis: [M++H]=408.0

Example 234

3,5-dimethyl-4-hydroxy-6-(5-(4-nitrobenzyloxy)benzofuran-2-yl)-2H-pyran-2-one

Mass analysis: [M++H]=408.0

Example 235

3,5-dimethyl-4-hydroxy-6-(6-(3-methoxybenzyloxy)benzofuran-2-yl)-2H-pyran-2-one

Mass analysis: [M++H]=393.0

Example 236

3,5-dimethyl-4-hydroxy-6-(5-(3-methoxybenzyloxy)benzofuran-2-yl)-2H-pyran-2-one

Mass analysis: [M++H]=393.0

Example 237

3,5-dimethyl-4-hydroxy-6-(6-(4-methoxybenzyloxy)benzofuran-2-yl)-2H-pyran-2-one

Mass analysis: [M++H]=393.0

Example 238

3,5-dimethyl-4-hydroxy-6-(5-(4-methoxybenzyloxy)benzofuran-2-yl)-2H-pyran-2-one

Mass analysis: [M++H]=393.0

Example 239

6-(6-(2-chlorobenzyloxy)benzofuran-2-yl)-3,5-dimethyl-4-hydroxy-2H-pyran-2-one

Mass analysis: [M++H]=397.0

Example 240

6-(5-(2-chlorobenzyloxy)benzofuran-2-yl)-3,5-dimethyl-4-hydroxy-2H-pyran-2-one

Mass analysis: [M++H]=397.0

Example 241

6-(6-(3-chlorobenzyloxy)benzofuran-2-yl)-3,5-dimethyl-4-hydroxy-2H-pyran-2-one

Mass analysis: [M++H]=397.0

Example 242

6-(5-(3-chlorobenzyloxy)benzofuran-2-yl)-3,5-dimethyl-4-hydroxy-2H-pyran-2-one

Mass analysis: [M++H]=397.0

Example 243

3,5-dimethyl-4-hydroxy-6-(5-(5-thiazolylmethoxy)benzofuran-2-yl)-2H-pyran-2-one $^1$H NMR($\delta$ ppm, DMSO-d6): 1.93(s, 3H), 2.28(s, 3H), 5.44(s, 2H), 7.08(dd, J=8.9 Hz, 2.7 Hz, 1H), 7.31(s, 1H), 7.37(d, J=2.7 Hz, 1H), 7.59(d, J=8.9 Hz, 1H), 8.02(s, 1H), 9.11(s, 1H)

Example 244

4-acetyloxy-6-(5-(2,4-dichloro-5-thiazolylmethoxy)benzofuran-2-yl)-3,5-dimethyl-2H-pyran-2-one $^1$H NMR($\delta$ ppm, CDCl$_3$): 2.00(s, 3H), 2.30(s, 3H), 2.39(s, 3H), 5.21(s, 2H), 7.01(dd, J=8.9 Hz, 2.4 Hz, 1H), 7.04(d, J=8.9 Hz, 1H), 7.27(d, J=2.4 Hz, 1H), 7.44(d, J=8.9 Hz, 1H)

Example 245

3,5-dimethyl-4-hydroxy-6-(5-(2-(morpholinesulfonyl)-5-thiazolylmethoxy)benzofuran-2-yl)-2H-pyran-2-one $^1$H NMR($\delta$ ppm, DMSO-d6): 1.94(s, 3H), 2.29(s, 3H), 3.15–3.18(m, 4H), 3.64 to 3.67(m, 4H), 5.53(s, 2H), 7.12 (dd, J=8.8 Hz, 2.7 Hz, 1H), 7.34(s, 1H), 7.39(d, J=2.7 Hz, 1H), 7.63(d, J=8.8 Hz, 1H), 8.26(s, 1H)

Example 246

3,5-dimethyl-4-hydroxy-6-(5-(3-thienylmethoxy)benzofuran-2-yl)-2H-pyran-2-one $^1$H NMR($\delta$ ppm, CD3OD): 1.93(s, 3H), 2.33(s, 3H), 5.13(s, 2H), 7.02(dd, J=8.9 Hz, 2.7 Hz, 1H), 7.18(d, J=2.7 Hz, 1H), 7.20(s, 1H), 7.24(d, J=2.7 Hz, 1H), 7.39 to 7.45(m, 3H)

Example 247

3,5-dimethyl-4-hydroxy-6-(5-(2-(morpholinesulfonyl)-5-thienylmethoxy)benzofuran-2-yl)-2H-pyran-2-one $^1$H NMR($\delta$ ppm, CDCl$_3$): 1.91(s, 3H), 2.31(s, 3H), 2.98 to 3.03(m, 4H), 3.71 to 3.75(m, 4H), 5.38(s, 2H), 7.03(dd, J=8.9 Hz, 2.7 Hz, 1H), 7.19(s, 1H), 7.27 to 7.29(m, 2H), 7.51(d, J=2.7 Hz, 1H)

Example 248

4-acetyloxy-3,5-dimethyl-6-(5-(2-(morpholinesulfonyl)-5-thienylmethoxy)benzofuran-2-yl)-2H-pyran-2-one $^1$H NMR($\delta$ ppm, CDCl$_3$): 2.00(s, 3H), 2.30(s, 3H), 2.40(s, 3H), 3.06 to 3.10(m, 4H), 3.74 to 3.81(m, 4H), 5.29(s, 2H), 7.04(dd, J=9.2 Hz, 2.7 Hz, 1H), 7.15(d, J=2.7 Hz, 1H), 7.31(s, 1H), 7.43 to 7.47(m, 2H)

Example 249

3,5-dimethyl-4-hydroxy-6-(5-(4-oxazolylmethoxy)benzofuran-2-yl)-2H-pyran-2-one

Mass analysis: [M$^+$+H]=354.0

Example 250

6-(5-(N-benzoyl-N-methylamino)benzofuran-2-yl)-3,5-dimethyl-4-hydroxy-2H-pyran-2-one Mass analysis: [M$^+$+H]=390.0

Example 251

3,5-dimethyl-4-hydroxy-6-(5-(N-methyl-N-(phenylacetyl)amino)benzofuran-2-yl)-2H-pyran-2-one Mass analysis: [M$^+$+H]=404.5

Example 252

3,5-dimethyl-4-hydroxy-6-(5-(N-methyl-N-(2-thienylcarbonyl)amino)benzofuran-2-yl)-2H-pyran-2-one Mass analysis: [M$^+$+H]=396.0

Example 253

3,5-dimethyl-4-hydroxy-6-(5-(N-methyl-N-(3-pyridylcarbonyl)amino)benzofuran-2-yl)-2H-pyran-2-one Mass analysis: [M$^+$+H]=391.0

Example 254

3,5-dimethyl-4-hydroxy-6-(5-(N-isobutyryl-N-methylamino)benzofuran-2-yl)-2H-pyran-2-one Mass analysis: [M$^+$+H]=356.0

Example 255

6-(5-(N-(t-butoxycarbonyl)-N-methylamino)benzofuran-2-yl)-3,5-dimethyl-4-hydroxy-2H-pyran-2-one Mass analysis: [M$^+$+H]=386.0

The following compounds were also produced by processes similar to those described in the preceding examples and production examples, using organic chemical techniques well-known to those skilled in the art.

Example 256
6-(5-benzoylaminobenzofuran-2-yl)-4-benzoyloxy-3,5-dimethyl-2H-pyran-2-one

Example 257
4-acetyloxy-3,5-dimethyl-6-(5-trifluoromethanesulfonyloxybenzofuran-2-yl)-2H-pyran-2-one

Example 258
6-(4-benzyloxybenzofuran-2-yl)-3,5-dimethyl-4-hydroxy-2H-pyran-2-one

Example 259
4-acetyloxy-3,5-dimethyl-6-(5-(methoxycarbonyl)benzofuran-2-yl)-2H-pyran-2-one

Example 260
4-acetyloxy-6-(4-benzyloxybenzofuran-2-yl)-3,5-dimethyl-2H-pyran-2-one

Example 261
4-acetyloxy-3,5-dimethyl-6-(5-hydroxybenzofuran-2-yl)-2H-pyran-2-one

Example 262
3,5-dimethyl-4-hydroxy-6-(5-hydroxybenzofuran-2-yl)-2H-pyran-2-one

Example 263
4-acetyloxy-3,5-dimethyl-6-(5-(4-methoxybenzoyloxy)benzofuran-2-yl)-2H-pyran-2-one

Example 264
4-acetyloxy-6-(5-carboxybenzofuran-2-yl)-3,5-dimethyl-2H-pyran-2-one

Example 265
4-acetyloxy-6-(4-acetyloxybenzofuran-2-yl)-3,5-dimethyl-2H-pyran-2-one

Example 266
4-acetyloxy-3,5-dimethyl-6-(4-methoxybenzofuran-2-yl)-2H-pyran-2-one

Example 267
3,5-dimethyl-4-hydroxy-6-(4-methoxybenzofuran-2-yl)-2H-pyran-2-one

Example 268
4-acetyloxy-3,5-dimethyl-6-(5-methoxybenzofuran-2-yl)-2H-pyran-2-one

Example 269
4-acetyloxy-6-(5-acetyloxybenzofuran-2-yl)-3,5-dimethyl-2H-pyran-2-one

Example 270
4-acetyloxy-6-(5-benzyloxybenzofuran-2-yl)-3,5-dimethyl-2H-pyran-2-one Example 271
6-(5-benzyloxybenzofuran-2-yl)-3,5-dimethyl-4-hydroxy-2H-pyran-2-one
Example 272
3,5-dimethyl-4-hydroxy-6-(6-hydroxybenzofuran-2-yl)-2H-pyran-2-one
Example 273
4-acetyloxy-3,5-dimethyl-6-(6-methoxybenzofuran-2-yl)-2H-pyran-2-one
Example 274
4-acetyloxy-3,5-dimethyl-6-(5-p-toluenesulfonyloxy benzofuran-2-yl)-2H-pyran-2-one
Example 275
4-acetyloxy-6-(6-acetyloxybenzofuran-2-yl)-3,5-dimethyl-2H-pyran-2-one
Example 276
6-(6-cyclohexyloxybenzofuran-2-yl)-3,5-dimethyl-4-hydroxy-2H-pyran-2-one
Example 277
3,5-dimethyl-4-hydroxy-6-(6-trifluoromethanesulfonyloxybenzofuran-2-yl)-2H-pyran-2-one
Example 278
4-acetyloxy-3,5-dimethyl-6-(6-(2-(methoxycarbonyl)ethoxy)benzofuran-2-yl)-2H-pyran-2-one
Example 279
3,5-dimethyl-4-hydroxy-6-(6-(2-(methoxycarbonyl)ethoxy)benzofuran-2-yl)-2H-pyran-2-one
Example 280
4-acetyloxy-6-(6-(2-(acetyloxy)ethoxy)benzofuran-2-yl)-3,5-dimethyl-2H-pyran-2-one
Example 281
3,5-dimethyl-4-hydroxy-6-(7-hydroxybenzofuran-2-yl)-2H-pyran-2-one
Example 282
4-acetyloxy-3,5-dimethyl-6-(7-methoxybenzofuran-2-yl -2H-pyran-2-one
Example 283
3,5-dimethyl-4-hydroxy-6-(4-hydroxybenzofuran-2-yl -2H-pyran-2-one
Example 284
4-acetyloxy-6-(7-acetyloxybenzofuran-2-yl)-3,5-dimethyl-2H-pyran-2-one
Example 285
4-acetyloxy-6-(7-benzyloxybenzofuran-2-yl)-3,5-dimethyl-2H-pyran-2-one
Example 286
6-(7-benzyloxybenzofuran-2-yl)-3,5-dimethyl-4-hydroxy-2H-pyran-2-one
Example 287
4-acetyloxy-6-(benzofuran-2-yl)-3-isopropyl-5-methyl-2H-pyran-2-one
Example 288
6-(4,6-dimethoxybenzofuran-2-yl)-3,5-dimethyl-4-hydroxy-2H-pyran-2-one
Example 289
4-acetyloxy-6-(4,6-dimethoxybenzofuran-2-yl)-3,5-dimethyl-2H-pyran-2-one
Example 290
3,5-dimethyl-4-hydroxy-6-(5-(methoxycarbonyl)benzofuran-2-yl)-2H-pyran-2-one
Example 291
3,5-dimethyl-4-hydroxy-6-(6-methoxymethoxybenzofuran-2-yl)-2H-pyran-2-one
Example 292
4-acetyloxy-3,5-dimethyl-6-(6-methoxymethoxybenzofuran-2-yl)-2H-pyran-2-one
Example 293
6-(5-carboxybenzofuran-2-yl)-3,5-dimethyl-4-hydroxy-2H-pyran-2-one
Example 294
4-acetyloxy-3,5-dimethyl-6-(5-(phenoxycarbonyl)benzofuran-2-yl)-2H-pyran-2-one
Example 295
4-acetyloxy-3,5-dimethyl-6-(5-(phenylcarbamoyl)benzofuran-2-yl)-2H-pyran-2-one
Example 296
4-acetyloxy-6-(5-benzoyloxybenzofuran-2-yl)-3,5-dimethyl-2H-pyran-2-one
Example 297
6-(5-(N-(4-chlorophenylsulfonyl)-N-methylamino)benzofuran-2-yl )-3,5-dimethyl-4-hydroxy-2H-pyran-2-one
Example 298
3,5-dimethyl-4-hydroxy-6-(5-(N-methyl-N-phenylsulfonyl)benzofuran-2-yl)-2H-pyran-2-one
Example 299
3,5-dimethyl-4-hydroxy-6-(5-(N-methyl-N-phenylcarbamoyl)benzofuran-2-yl)-2H-pyran-2-one
Example 300
6-(5-(benzimidazolylcarbamoyl)benzofuran-2-yl)-3,5-dimethyl-4-hydroxy-2H-pyran-2-one
Example 301
6-(5-(benzothiazolylcarbamoyl)benzofuran-2-yl)-3,5-dimethyl-4-hydroxy-2H-pyran-2-one
Example 302
3,5-dimethyl-4-hydroxy-6-(5-(1,3,4-trihydroiso quinolin-2-ylcarbonyl)benzofuran-2-yl)-2H-pyran-2-one
Example 303
3,5-dimethyl-4-hydroxy-6-(5-morpholinylbenzofuran-2-yl )-2H-pyran-2-one
Example 304
3,5-dimethyl-4-hydroxy-6-(5-(5-hydroxy-3-pyridylmethoxy)benzofuran-2-yl)-2H-pyran-2-one
Example 305
3,5-dimethyl-4-hydroxy-6-(5-(4-(sulfamoyl)phenylcarbamoyl)benzofuran-2-yl)-2H-pyran-2-one
Example 306
3,5-dimethyl-4-hydroxy-6-(5-(4-pyridylmethylcarbamoyl)benzofuran-2-yl)-2H-pyran-2-one
Example 307
3,5-dimethyl-4-hydroxy-6-(5-(4-piperidinyl)benzofuran-2-yl )-2H-pyran-2-one
Example 308
6-(5-(N-benzyl-N-methylcarbamoyl)benzofuran-2-yl)-3,5-dimethyl-4-hydroxy-2H-pyran-2-one
Example 309
3,5-dimethyl-4-hydroxy-6-(5-(N-methyl-N-(4-pyridyl)carbamoyl)benzofuran-2-yl)-2H-pyran-2-one

Example 310

Preparation of Cells

Human hepatic cancer cells HepG2 were inoculated into a 24-well plate (Costar No. 3524) at $4 \times 10^4$ cells/well, and 1 ml of medium (eRDF medium containing 10% bovine serum (Kyokuto Chemical Co.)) was used for 6 day culturing with 5% $CO_2$ at 37° C. After drawing off the supernatant medium, the cells were freshly rinsed with 1 ml of PBS(−) buffer solution (Takara Shuzo) and drawn off. This procedure was repeated twice and then 1 ml of fresh medium (eRDF medium) was added.

Preparation of Sample 6-(benzofuran-2-yl)-3,5-dimethyl-4-hydroxy-2H-pyran-2-one (Example 2) was dissolved in dimethylsulfoxide (DMSO) to prepare a 20 mM sample stock solution. A diluted solution was obtained by diluting the sample solution with DMSO.

TG Production

To the cells prepared above there were added the sample stock solution or its diluted solution at 5 μl per well and 10 μl of $^{14}$C-acetic acid solution (a solution of Amersham Code No. CFA13 diluted 4.4-fold with PBS(−) buffer), and culturing was carried out for one day with 5% $CO_2$ at 37° C.

TG Quantification

After the culturing was completed, the culture solution was removed, and 1 ml of extraction solution (a mixture of n-hexane and isopropyl alcohol at 2:1) was added for extraction treatment on the lipid components in the cells. After the treatment, the extract containing the obtained lipid components was air-dried, the residue was redissolved in 20 μl of a mixed solution of n-hexane and ethyl acetate at 9:1, and the solution was spotted on a thin-layer chromatography plate (S319, Tokyo Kasei) and developed by thin-layer chromatography with the mixed solution mentioned above. After air-drying, the lipid components were colored with iodine vapor, the portion corresponding to TG was cut out, and the amount of TG biosynthesized was measured with a liquid scintillation counter. The results are shown in Table 1. It was demonstrated that 6-(benzofuran-2-yl)-3,5-dimethyl-4-hydroxy-2H-pyran-2-one exhibits triglyceride biosynthesis inhibiting activity.

TABLE 1

| Sample concentration (Example 2) | TG production inhibiting activity |
|---|---|
| 1 μM | 22% |
| 10 μM | 70% |
| 100 μM | 98% |

Example 311

The TG production inhibiting activity of the invention compounds was evaluated in the same manner as the above example. According to the results of the evaluation, the compounds of the following example numbers exhibited an $IC_{50}$ value of less than 10 μM, at least 30% TG production inhibiting activity at a concentration of 1 μM, or at least 50% TG production inhibiting activity at a concentration of 10 μM: 1, 2, 3, 4, 5, 9, 10, 11, 12, 13, 19, 25, 26, 27, 28, 29, 30, 31, 33, 34, 36, 39, 40, 42, 45, 48, 49, 50, 51, 52, 53, 54, 55, 56, 57, 58, 59, 61, 62, 63, 64, 65, 66, 69, 70, 71, 72, 75, 76, 78, 85, 89, 97, 117, 120, 122, 134, 138, 153, 159, 163, 170, 215, 226, 228, 236, 242, 243, 244, 245, 246, 247, 248, 249, 250, 251, 252, 255, 257, 259, 260, 265, 268, 270, 271, 274, 285, 290, 291, 297, 298, 299, 300, 301, 302, 303, 304, 305, 306, 307, 308, 309.

The compounds of the following example numbers exhibited an $IC_{50}$ value of at least 10 μM and less than 100 μM; at least 5% and less than 30% TG production inhibiting activity at a concentration of 1 μM; or at least 30% and less than 50% TG production inhibiting activity at a concentration of 10 μM: 6, 7, 8, 14, 17, 18, 20, 22, 23, 24, 32, 35, 37, 38, 43, 46, 47, 60, 67, 68, 74, 79, 81, 83, 87, 95, 107, 115, 124, 126, 144, 155, 157, 175, 177, 179, 181, 183, 185, 187, 191, 193, 195, 197, 201, 203, 207, 213, 217, 220, 222, 224, 230, 240, 253, 254, 258, 261, 262, 263, 264, 266, 267, 269, 272, 273, 275, 278, 280, 281, 282, 283, 284, 286, 287, 292, 295, 296.

Example 312

Drug Effect Evaluation Test 6-(benzofuran-2-yl)-3,5-dimethyl-4-hydroxy-2H-pyran-2-one (Example 2) was suspended in a 0.5% carboxymethyl cellulose Na aqueous solution (vehicle) to prepare 20 mg/ml and 60 mg/ml administration solutions, and these were orally administered to 6-week-old SD male rats at a dose of 5 ml/kg once a day, for 7 consecutive days. CE-2 by Nihon Crea Co. was used for the rat feed, and the rats were allowed free access to food and water. The rats were separated into a vehicle-administered group of 6 rats and a drug-administered group of 6 rats for a test. At 4 hours after the final drug administration, the rats were killed under ether anesthesia, blood was drawn from the abdominal aorta, and the serum levels of TG, total cholesterol (TC) and HDL- were measured.

Triglyceride EII-HA Test Wako (product of Wako Junyaku Kogyo) was used for the TG measurement, HA Test Wako/Cholesterol E-HA Test Wako (product of Wako Junyaku Kogyo) was used for the total cholesterol (TC) measurement, and HDL-cholesterol Test Wako (product of Wako Junyaku Kogyo) was used for the HDL measurement.

As shown in Table 2, the invention compound-administered group had dose-dependent lower TG levels. Also, as shown in Table 3, the TC and HDL levels increased in a dose dependent manner. The increase in TC was almost totally due to an increase in HDL. No cases of rat death or inhibited body weight gain were found during the administration period.

TABLE 2

| Administered solution | Serum TG (mg/dl) (mean ± SE) |
|---|---|
| No sample administered | 108.3 ± 8.9 |
| Example 2 (100 mg/kg) | 94.8 ± 6.5 |
| Example 2 (300 mg/kg) | 74.8 ± 10.7 |

TABLE 3

| Administered solution | Serum HDL-C (mg/dl) (mean ± SE) |
|---|---|
| No sample administered | 30.5 ± 1.7 |
| Example 2 (100 mg/kg) | 35.0 ± 3.1 |
| Example 2 (300 mg/kg) | 42.2 ± 3.8 |

The above data demonstrate that the compounds of the invention have TG-lowering effects and/or HDL-elevating effects, and are therefore useful as blood triglyceride lowering agents, lipid metabolism enhancers, arteriosclerosis prophylactic agents or arteriosclerosis treatment agents.

Example 313

Tablets were prepared with each tablet having the following composition.

| | |
|---|---|
| Active ingredient | 200 μg |
| Lactose | 180 mg |
| Potato starch | 50 mg |
| Polyvinyl pyrrolidone | 10 mg |
| Magnesium stearate | 5 mg |

The active ingredient, lactose and potato starch were combined, and the mixture was evenly moistened with a 20% ethanol solution of polyvinyl pyrrolidone. The moistened mixture was passed through a 20 mesh sieve, dried at 45° C. and then passed through a 15 mesh sieve. The granules obtained in this manner were blended with magnesium stearate and compressed into tablets.

Example 314

Hard gelatin capsules were prepared with each capsule containing the following composition.

| | |
|---|---|
| Active ingredient | 100 μg |
| Fine crystalline cellulose | 195 mg |
| Amorphous silicic acid | 5 mg |

The active ingredient, fine crystalline cellulose and unpressed amorphous silicic acid were thoroughly blended and filled into hard gelatin capsules.

Example 315

The active ingredient was dissolved in fractionated coconut oil. This was heated and dissolved in a coating component having the following formula, and a soft capsule manufacturing machine was used to prepare soft capsules by a common procedure, with 100 μg of the active ingredient in each capsule.

Coating Formula

| | |
|---|---|
| Gelatin | 10 parts by weight |
| Glycerin | 5 parts by weight |
| Sorbic acid | 0.08 parts by weight |
| Purified water | 14 parts by weight |

INDUSTRIAL APPLICABILITY

The pharmaceutical agents of the present invention exhibit triglyceride biosynthesis inhibiting action, blood triglyceride lowering effects or blood HDL level elevating effects, and they may therefore be used as therapeutic agents for hypertriglyceridemia, as lipid metabolism enhancers, or as prophylactic and/or therapeutic agents for arteriosclerosis.

What is claimed is:

1. A benzofuryl-α-pyrone derivative represented by the following structural formula (I)

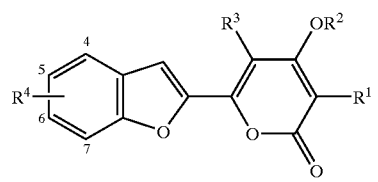

wherein
$R^1$ represents hydrogen or an alkyl group of 1 to 5 carbons;
$R^2$ represents hydrogen, —CO—$R^5$ (wherein $R^5$ represents hydrogen, an alkyl group of 1 to 5 carbons with optional substituents, a cycloalkyl group of 3 to 7 carbons, or an aryl group of 6 to 10 carbons), or —$SO_2R^6$ (wherein $R^6$ represents an optionally halogen-substituted alkyl group of 1 to 5 carbons or aryl group of 6 to 10 carbons);
$R^3$ represents hydrogen, an alkyl group of 1 to 5 carbons, an alkenyl group of 2 to 5 carbons, an alkynyl group of 2 to 5 carbons, a cycloalkyl group of 3 to 7 carbons, a cycloalkyl group of 3 to 7 carbons-alkyl group of 1 to 5 carbons, an aryl group of 6 to 10 carbons, an aralkyl group of 7 to 20 carbons-alkoxy group of 1 to 5 carbons or an aryloxy group of 6 to 10 carbons;
$R^4$ is a substituent at the C-4 position, C-5 position, C-6 position or C-7 position of the benzofuran ring and represents:
$R^{4a}$ which represents hydrogen, a nitro group, a cyano group, a halogen atom, an alkenyl group of 2 to 5 carbons, an alkynyl group of 2 to 5 carbons, an aryl group of 6 to 10 carbons, —$OR^7$ (wherein $R^7$ represents hydrogen, a cycloalkyl group of 3 to 7 carbons, an aryl group of 6 to 10 carbons, an optionally halogen-substituted alkylsulfonyl group of 1 to 4 carbons or an arylsulfonyl group of 6 to 10 carbons), —O—CO—$R^8$ (wherein $R^8$ represents hydrogen, an alkyl group of 1 to 4 carbons, an aryl group of 6 to 10 carbons, or an aralkyl group of 7 to 20 carbons), —$NR^9R^{10}$ (wherein $R^9$ and $R^{10}$ each independently represents hydrogen, an alkyl group of 1 to 4 carbons, an aralkyl group of 7 to 20 carbons, a phenyl group, —$SO_2$—$R^{11}$ (wherein $R^{11}$ represents an optionally halogen-substituted alkyl group of 1 to 12 carbons, an aryl group of 6 to 10 carbons, or an aralkyl group of 7 to 20 carbons) or —CO—$R^{12}$ (wherein $R^{12}$ represents hydrogen, an alkyl group of 1 to 12 carbons, an aryl group of 6 to 10 carbons, an aralkyl group of 7 to 20 carbons, an alkoxy group of 1 to 10 carbons, an aryloxy group of 6 to 10 carbons, or an aralkyloxy group of 7 to 20 carbons)), —CO—$R^{13}$ (wherein $R^{13}$ represents hydrogen, —OH, an alkyl group of 1 to 4 carbons, an aryl group of 6 to 10 carbons, an alkoxy group of 1 to 4 carbons, an aryloxy group of 6 to 10 carbons or an aralkyloxy group of 7 to 20 carbons) or —CO—$NR^{14}R^{15}$ (wherein $R^{14}$ and $R^{15}$ each independently represents hydrogen, an alkyl group of 1 to 4 carbons, a cycloalkyl group of 3 to 7 carbons, an aryl group of 6 to 10 carbons, or an aralkyl group of 7 to 20 carbons);
$R^{4b}$ which represents a saturated or unsaturated alkoxy group of 1 to 6 carbons optionally substituted with 1 to 3 groups selected from the group consisting of halogens, cycloalkyl groups of 3 to 7 carbons, phenyl, naphthyl, —OR$^{16}$ (wherein R$^{16}$ represents hydrogen, an alkyl group of 1 to 4 carbons, a phenyl group, a naphthyl group, or a benzyl group), —O—CO—R$^{16}$ (wherein R$^{16}$ represents hydrogen, an alkyl group of 1 to 4 carbons, a phenyl group, a naphthyl group, or a benzyl group), —NR$^{17}$R$^{18}$ (wherein R$^{17}$ and R$^{18}$ each independently represents hydrogen, an alkyl group of 1 to 4 carbons, an alkylsulfonyl group of 1 to 4 carbons, a phenylsulfonyl group, an aminosulfonyl group, a methylaminosulfonyl group, a dimethylaminosulfonyl group, a diethylaminosulfonyl group, or an alkyl group of 1 to 4 carbons substituted with 1 or 2 groups selected from among phenyl, phenoxy, and hydroxyl), —NH—CO—R$^{19}$ (wherein R$^{19}$ represents hydrogen, an alkyl group of 1 to 4 carbons, a phenyl group, a naphthyl group, a benzyl group, an alkoxy group of 1 to 4 carbons or a benzyloxy group), —CO—R$^{20}$ (wherein R$^{20}$ represents hydrogen, an alkoxy group of 1 to 4 carbons, a phenoxy group, a benzyloxy group or —OR$^{21}$ (wherein R$^{21}$ represents hydrogen) and —CO—NR$^{22}$R$^{23}$ (wherein R$^{22}$ and R$^{23}$ each independently represents hydrogen, an alkyl group of 1 to 4 carbons, or a benzyl group); or R$^{4C}$ which represents an alkyl group of 1 to 4 carbons optionally substituted with 1 to 3 groups selected from the group consisting of halogens, cycloalkyl groups of 3 to 7 carbons, phenyl, naphthyl, —SH, —OR$^{16}$ (wherein R$^{16}$ represents hydrogen, an alkyl group of 1 to 4 carbons, a phenyl group, a naphthyl group, or a benzyl group), —O—CO—R$^{16}$ (wherein R$^{16}$ represents hydrogen, an alkyl group of 1 to 4 carbons, a phenyl group, a naphthyl group, or a benzyl group), —NR$^{17}$R$^{18}$ (wherein R$^{17}$ and R$^{18}$ each independently represents hydrogen, an alkyl group of 1 to 4 carbons, an alkylsulfonyl group of 1 to 4 carbons, a phenylsulfonyl group, an aminosulfonyl group, a methylaminosulfonyl group, a dimethylaminosulfonyl group, a diethylaminosulfonyl group, or an alkyl group of 1 to 4 carbons substituted with 1 or 2 groups selected from among phenyl, phenoxy, and hydroxyl), —NH—CO—R$^{19}$ (wherein R$^{19}$ represents hydrogen, an alkyl group of 1 to 4 carbons, a phenyl group, a naphthyl group, a benzyl group, an alkoxy group of 1 to 4 carbons or a benzyloxy group), —CO—R$^{20}$ (wherein R$^{20}$ represents hydrogen, an alkoxy group of 1 to 4 carbons, a phenoxy group, a benzyloxy group or —OR$^{21}$ (wherein R$^{21}$ represents hydrogen) and —CO—NR$^{22}$R$^{23}$ (wherein R$^{22}$ and $^{23}$ each independently represents hydrogen, an alkyl group of 1 to 4 carbons, or a benzyl group); or a salt thereof.

2. A benzofuryl-α-pyrone derivative according to claim 1 wherein R$^1$ is methyl; or a salt thereof.

3. A benzofuryl-α-pyrone derivative according to claim 1, wherein R$^2$ is hydrogen or —CO—R$^5$; or a salt thereof.

4. A benzofuryl-α-pyrone derivative according to claim 3, wherein R$^2$ is hydrogen or acetyl; or a salt thereof.

5. A benzofuryl-α-pyrone derivative according to claim 1, wherein R$^3$ is hydrogen, an alkyl group of 1 to 5 carbons, an alkenyl group of 2 to 5 carbons, an alkynyl group of 2 to 5 carbons, a 2-cycloalkylmethyl group of 4 to 8 carbons, a cycloalkylethyl group of 5 to 9 carbons, a phenyl group, a benzyl group, a phenethyl group, a methoxy group or a phenoxy group; or a salt thereof.

6. A benzofuryl-α-pyrone derivative according to claim 5, wherein R$^3$ is an alkyl group of 1 to 5 carbons; or a salt thereof.

7. A benzofuryl-α-pyrone derivative according to claim 6, wherein R$^3$ is methyl or ethyl; or a salt thereof.

8. A benzofuryl-α-pyrone derivative according to any one of claims 1, 2, 3, 4, 5, 6 or 7, wherein R$^{4c}$ is an alkyl group of 1 to 3 carbons optionally substituted with 1 to 3 substituents selected from the group consisting of —SH, —OH, alkoxy groups of 1 to 4 carbons, acyloxy groups of 1 to 4 carbons, —NR$^{40}$R$^{41}$ (wherein R$^{40}$ and R$^{41}$ each independently represents hydrogen, an alkyl group of 1 to 4 carbons, an optionally halogen-substituted alkylsulfonyl group of 1 to 4 carbons, or an alkyl group of 1 or 2 carbons substituted with 1 or 2 substituents selected from among phenyl, phenoxy, and hydroxyl), —NH—CO—R$^{42}$ (wherein R$^{42}$ represents hydrogen, phenyl, an alkyl group of 1 to 4 carbons or an alkoxy group of 1 to 4 carbons), —CO—R$^{43}$ (wherein R$^{43}$ represents hydrogen, an alkoxy group of 1 to 4 carbons or —OR$^{21}$ (wherein R$^{21}$ represents hydrogen) and —CO—NR$^{44}$R$^{45}$ (wherein R$^{44}$ and R$^{45}$ each independently represents hydrogen, or an alkyl group of 1 to 4 carbons); or a salt thereof.

9. A benzofuryl-α-pyrone derivative according to any one of claims 1, 2, 3, 4, 5, 6 or 7, wherein R$^{4c}$ is an alkyl group of 1 to 3 carbons substituted with —SH, benzoylamino, an acylamino group of 1 to 5 carbons or —NR$^{40}$R$^{41}$ (wherein R$^{40}$ and R$^{41}$ each independently represents hydrogen, an alkyl group of 1 to 4 carbons, an optionally halogen-substituted alkylsulfonyl group of 1 to 4 carbons, or an alkyl group of 1 or 2 carbons substituted with 1 or 2 substituents selected from among phenyl, or phenoxy, and hydroxyl); or a salt thereof.

10. A benzofuryl-α-pyrone derivative according to any one of claims 1, 2, 3, 4, 5, 6 or 7, wherein R$^{4b}$ is an alkoxy group of 1 to 6 carbons optionally substituted with 1 to 3 substituents selected from the group consisting of halogens, cycloalkyl groups of 3 to 7 carbons, phenyl, naphthyl, acyloxy groups of 1 to 4 carbons, —CHO, —CO$_2$H, alkoxycarbonyl groups of 2 to 5 carbons, —OR$^{46}$ (wherein R$^{46}$ represents hydrogen, an alkyl group of 1 to 4 carbons, a phenyl group, or a benzyl group) and —NR$^{47}$R$^{48}$ (wherein R$^{47}$ and R$^{48}$ each independently represents hydrogen, an alkyl group of 1 to 4 carbons, an alkoxycarbonyl group of 2 to 5 carbons, an alkylsulfonyl group of 1 to 4 carbons, a phenylsulfonyl group, an aminosulfonyl group, a methylaminosulfonyl group, a dimethylaminosulfonyl group, a diethylaminosulfonyl group, an acyl group of 1 to 5 carbons, a benzoyl group, a benzyloxycarbonyl group, or an alkyl group of 1 to 4 carbons substituted with 1 or 2 groups selected from among phenyl, phenoxy, and hydroxyl) or an unsaturated alkoxy group of 3 to 6 carbons; or a salt thereof.

11. A benzofuryl-α-pyrone derivative according to any one of claims 1, 2, 3, 4, 5, 6 or 7, wherein R$^{4b}$ is methoxy, 2-propynyloxy, 2,2-dimethylpropoxy, cyclopentylmethoxy, 2-bromoethoxy, benzyloxy, chlorobenzyloxy, fluorobenzyloxy, (trifluoromethyl)benzyloxy, dichlorobenzyloxy, dimethylbenzyloxy, methoxybenzyloxy, sulfamoylbenzyloxy, carboxybenzyloxy, (methoxycarbonyl) benzyloxy, n-butoxybenzyloxy, aminobenzyloxy, (t-butoxycarbonylamino)benzyloxy, 3-phenylpropoxy, di(methoxyphenyl)methoxy, 1-methyl-1-phenylethoxy, naphthylmethoxy, methoxymethyl, 2-(acetyloxy)ethoxy, bis (dimethylaminomethyl)methoxy, 4-(t-butoxycarbonylamino)butoxy, ethoxycarbonylmethoxy, 2-(methoxycarbonyl)ethoxy, 5-(ethoxycarbonyl)pentyloxy or 2-(benzyloxy)ethoxy; or a salt thereof.

12. A benzofuryl-α-pyrone derivative according to any one of claims 1, 2, 3, 4, 5, 6 or 7, wherein R$^{4b}$ is methoxy, 2-propynyloxy, benzyloxy, chlorobenzyloxy, fluorobenzyloxy, (trifluoromethyl)benzyloxy, dichlorobenzyloxy, dimethylbenzyloxy, methoxybenzyloxy, sulfamoylbenzyloxy, carboxybenzyloxy, (methoxycarbonyl) benzyloxy, n-butoxybenzyloxy, aminobenzyloxy, (t-butoxycarbonylamino)benzyloxy or methoxymethyl; or a salt thereof.

13. A benzofuryl-α-pyrone derivative according to any one of claims 1, 2, 3, 4, 5, 6 or 7, wherein $R^{4a}$ is hydrogen, a nitro group, a cyano group, a halogen atom, $—OR^{49}$ (wherein $R^{49}$ represents hydrogen, an optionally halogen-substituted alkylsulfonyl group of 1 to 4 carbons or a phenylsulfonyl group), $—O—CO—R^{50}$ (wherein $R^{50}$ represents hydrogen, an alkyl group of 1 to 4 carbons or phenyl), $—NR^{51}R^{52}$ (wherein $R^{51}$ and $R^{52}$ each independently represents hydrogen, an alkyl group of 1 to 4 carbons, phenyl, benzyl, $—SO_2—R^{53}$ (wherein $R^{53}$ represents phenyl, naphthyl, or an alkyl group of 1 to 3 carbons optionally substituted with 1 to 3 substituents selected from the group consisting of halogen atoms, and phenyl), or $—CO—R^{54}$ (wherein $R^{54}$ represents hydrogen, phenyl, naphthyl, an alkoxy group of 1 to 4 carbons, a phenoxy group, a naphthyloxy group, an aralkyloxy group of 7 to 11 carbons or an alkyl group of 1 to 3 carbons optionally substituted with phenyl)), $—CO—R^{55}$ (wherein $R^{55}$ represents hydrogen, $—OH$, an alkoxy group of 1 to 4 carbons or a phenoxy group), or $—CO—NR^{56}R^{57}$ (wherein $R^{56}$ and $R^{57}$ each independently represent hydrogen, an alkyl group of 1 to 4 carbons, a cycloalkyl group of 3 to 7 carbons, a phenyl group, a benzyl group, or a phenethyl group,); or a salt thereof.

14. A benzofuryl-α-pyrone derivative according to any one of claims 1, 2, 3, 4, 5, 6 or 7, wherein $R^{4a}$ is hydrogen, a nitro group, a cyano group, a halogen atom, $—R^{58}$ (wherein $R^{58}$ represents hydrogen, an optionally halogen-substituted alkylsulfonyl group of 1 to 4 carbons or a phenylsulfonyl group), $—O—CO—R^{59}$ (wherein $R^{59}$ represents an alkyl group of 1 to 4 carbons or phenyl), $—NR^{60}R^{61}$ (wherein $R^{60}$ and $R^{61}$ each independently represents hydrogen, an alkyl group of 1 to 4 carbons, phenyl, benzyl, $—SO_2—R^{62}$ (wherein $R^{62}$ represents an optionally halogen-substituted alkyl group of 1 to 3 carbons, a phenyl group, a benzyl group or a phenethyl group) or $—CO—R^{63}$ (wherein $R^{63}$ represents an alkyl group of 1 to 4 carbons, a phenyl group, an aralkyl group of 7 to 9 carbons, an alkoxy group of 1 to 4 carbons, a phenoxy group, or a benzyloxy group)), $—CO—R^{64}$ (wherein $R^{64}$ represents hydrogen, $—OH$ or an alkoxy group of 1 to 4 carbons), or $—CO—NR^{65}R^{66}$ (wherein $R^{65}$ and $R^{66}$ each independently represents hydrogen, an alkyl group of 1 to 4 carbons, a cycloalkyl group of 3 to 7 carbons, a phenyl group, a benzyl group, or a phenethyl group); or a salt thereof.

15. A benzofuryl-α-pyrone derivative according to any one of claims 1, 2, 3, 4, 5, 6 or 7, wherein $R^{4a}$ is hydrogen, nitro, cyano, bromine, hydroxyl, methanesulfonyloxy, trifluoromethanesulfonyloxy, phenylsulfonyloxy, acetyloxy, benzoyloxy, dimethylamino, dibenzylamino, phenylsulfonylamino, dimethylcarbamoyl, N-methyl-N-phenylcarbamoyl, N-benzyl-N-methylcarbamoyl, cyclohexylcarbamoyl, phenylcarbamoyl, formyl, carboxyl, methoxycarbonyl, ethoxycarbonyl, n-propoxycarbonyl, isopropoxycarbonyl, t-butoxycarbonyl, acetyl, benzoyl, or $—NR^{67}—CO—R^{68}$ (wherein $R^{67}$ represents an alkyl group of 1 to 4 carbons and $R^{68}$ represents an alkyl group of 1 to 3 carbons, a phenyl group, an aralkyl group of 7 to 9 carbons or an alkoxy group of 1 to 4 carbons); or a salt thereof.

16. A benzofuryl-α-pyrone derivative according to any one of claims 1, 2, 3, 4, 5, 6 or 7, wherein $R^{4a}$ is hydrogen, nitro, cyano, bromine, hydroxyl, trifluoromethanesulfonyloxy, phenylsulfonyloxy, acetyloxy, dimethylamino, dibenzylamino, methoxycarbonyl, isopropoxycarbonyl, or $—N(Me)—CO—R^{69}$ (wherein $R^{69}$ represents an alkyl group of 1 to 3 carbons, a phenyl group, a benzyl group or an alkoxy group of 1 to 4 carbons); or a salt thereof.

17. A benzofuryl-α-pyrone derivative represented by the following structural formula (I)

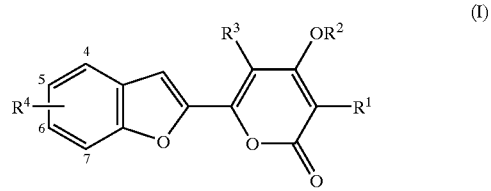

wherein
$R^1$ represents hydrogen or an alkyl group of 1 to 5 carbons;
$R^2$ represents hydrogen, $—CO—R^5$ (wherein $R^5$ represents hydrogen, an alkyl group of 1 to 5 carbons with optional substituents, a cycloalkyl group of 3 to 7 carbons, or an aryl group of 6 to 10 carbons), or $—SO_2R^6$ (wherein $R^6$ represents an optionally halogen-substituted alkyl group of 1 to 5 carbons or aryl group of 6 to 10 carbons);
$R^3$ represents hydrogen, an alkyl group of 1 to 5 carbons, an alkenyl group of 2 to 5 carbons, an alkynyl group of 2 to 5 carbons, a cycloalkyl group of 3 to 7 carbons, a cycloalkyl group of 3 to 7 carbons-alkyl group of 1 to 5 carbons, an aryl group of 6 to 10 carbons, an aralkyl group of 7 to 20 carbons, an alkoxy group of 1 to 5 carbons or an aryloxy group of 6 to 10 carbons;
$R^4$ is a substituent at the C-4 position, C-5 position, C-6 position or C-7 position of the benzofuran ring and represents:
$R^{4a}$ which represents hydrogen, a nitro group, a cyano group, a halogen atom, an alkenyl group of 2 to 5 carbons, an alkynyl group of 2 to 5 carbons, an aryl group of 6 to 10 carbons, $—OR^7$ (wherein $R^7$ represents hydrogen, a cycloalkyl group of 3 to 7 carbons, an aryl group of 6 to 10 carbons, an optionally halogen-substituted alkylsulfonyl group of 1 to 4 carbons or an arylsulfonyl group of 6 to 10 carbons), $—O—CO—R^8$ (wherein $R^8$ represents hydrogen, an alkyl group of 1 to 4 carbons, an aryl group of 6 to 10 carbons, or an aralkyl group of 7 to 20 carbons), $—NR^9R^{10}$ (wherein $R^9$ and $R^{10}$ each independently represents hydrogen, an alkyl group of 1 to 4 carbons, an aralkyl group of 7 to 20 carbons, a phenyl group, $—SO_2—R^{11}$ (wherein $R^{11}$ represents an optionally halogen-substituted alkyl group of 1 to 12 carbons, an aryl group of 6 to 10 carbons, or an aralkyl group of 7 to 20 carbons) or $—CO—R^{12}$ (wherein $R^{12}$ represents hydrogen, an alkyl group of 1 to 12 carbons, an aryl group of 6 to 10 carbons, an aralkyl group of 7 to 20 carbons, an alkoxy group of 1 to 10 carbons, an aryloxy group of 6 to 10 carbons, or an aralkyloxy group of 7 to 20 carbons)), $—CO—R^{13}$ (wherein $R^{13}$ represents hydrogen, $—OH$, an alkyl group of 1 to 4 carbons, an aryl group of 6 to 10 carbons, an alkoxy group of 1 to 4 carbons, an aryloxy group of 6 to 10 carbons or an aralkyloxy group of 7 to 20 carbons) or $—CO—$ $NR^{14}R^{15}$ (wherein $R^{14}$ and $R^{15}$ each independently represents hydrogen, an alkyl group of 1 to 4 carbons, a cycloalkyl group of 3 to 7 carbons, an aryl group of 6 to 10 carbons, or an aralkyl group of 7 to 20 carbons;

$R^{4b}$ which represents a saturated or unsaturated alkoxy group of 1 to 6 carbons optionally substituted with 1 to 3 groups selected from the group consisting of halogens, cycloalkyl groups of 3 to 7 carbons, phenyl, naphthyl, —$OR^{16}$ (wherein $R^{16}$ represents hydrogen, an alkyl group of 1 to 4 carbons, a phenyl group, a naphthyl group, or a benzyl group), —O—CO—$R^{16}$ (wherein $R^{16}$ represents hydrogen, an alkyl group of 1 to 4 carbons, a phenyl group, a naphthyl group, or a benzyl group), —$NR^{17}R^{18}$ (wherein $R^{17}$ and $R^{18}$ each independently represents hydrogen, an alkyl group of 1 to 4 carbons, or an alkyl group of 1 to 4 carbons substituted with 1 or 2 groups selected from among phenyl, phenoxy, and hydroxyl), —NH—CO—$R^{19}$ (wherein $R^{19}$ represents hydrogen, an alkyl group of 1 to 4 carbons, a phenyl group, a naphthyl group, a benzyl group, an alkoxy group of 1 to 4 carbons or a benzyloxy group), and —CO—$R^{20}$ (wherein $R^{20}$ represents hydrogen, an alkoxy group of 1 to 4 carbons, a phenoxy group, a benzyloxy group or —$OR^{21}$ (wherein $R^{21}$ represents hydrogen); or $R^{4}c$ which represents an alkyl group of 1 to 4 carbons optionally substituted with 1 to 3 groups selected from the group consisting of halogens, cycloalkyl groups of 3 to 7 carbons, phenyl, naphthyl, —SH, —$OR^{16}$ (wherein $R^{16}$ represents hydrogen, an alkyl group of 1 to 4 carbons, a phenyl group, a naphthyl group, or a benzyl group), —O—CO—$R^{16}$ (wherein $R^{16}$ represents hydrogen, an alkyl group of 1 to 4 carbons, a phenyl group, a naphthyl group, or a benzyl group), —$NR^{17}R^{18}$ (wherein $R^{17}$ and $R^{18}$ each independently represents hydrogen, an alkyl group of 1 to 4 carbons, phenoxy, and hydroxyl), —NH—CO—$R^{19}$ (wherein $R^{19}$ represents hydrogen, an alkyl group of 1 to 4 carbons, a phenyl group, a naphthyl group, a benzyl group, an alkoxy group of 1 to 4 carbons or a benzyloxy group), and —CO—$R^{20}$ (wherein 20 represents hydrogen, an alkoxy group of 1 to 4 carbons, a phenoxy group, a benzyloxy group or —$OR^{21}$ (wherein $R^{21}$ represents hydrogen); or a salt thereof.

18. A pharmaceutical composition comprising a therapeutically effective dose of a benzofuryl-α-pyrone derivative according to any one of claims 1, 2, 3, 4, 5, 6 or 7 or its salt, and a pharmaceutically acceptable carrier.

19. A composition comprising as an active ingredient a benzofuryl-α-pyrone derivative according to claim 17 or its salt, and a pharmaceutically acceptable carrier, wherein said composition is a lipid metabolism enhancer, a triglyceride biosynthesis inhibitor, a blood triglyceride lowering agent, a blood HDL elevating agent, an arteriosclerosis prophylactic agent or an arteriosclerosis treatment agent.

* * * * *